United States Patent
Ahmed et al.

(10) Patent No.: US 10,182,726 B2
(45) Date of Patent: Jan. 22, 2019

(54) DEVICE FOR PHYSIOLOGICAL MONITORING AND MEASUREMENT

(71) Applicant: Whoop, Inc., Boston, MA (US)

(72) Inventors: William Ahmed, Boston, MA (US); John Capodilupo, Boston, MA (US); Aurelian Nicolae, Brookline, MA (US)

(73) Assignee: Whoop, Inc., Boston, MA (US)

( * ) Notice: Subject to any disclaimer, the term of this patent is extended or adjusted under 35 U.S.C. 154(b) by 20 days.

(21) Appl. No.: 14/995,874

(22) Filed: Jan. 14, 2016

(65) Prior Publication Data

US 2016/0129310 A1   May 12, 2016

Related U.S. Application Data

(63) Continuation of application No. 14/326,598, filed on Jul. 9, 2014, which is a continuation of application No. 14/018,262, filed on Sep. 4, 2013.
(Continued)

(51) Int. Cl.
*A61B 5/11* (2006.01)
*A61B 5/0205* (2006.01)
(Continued)

(52) U.S. Cl.
CPC .......... *A61B 5/0205* (2013.01); *A61B 5/0004* (2013.01); *A61B 5/0022* (2013.01);
(Continued)

(58) Field of Classification Search
CPC . A61B 5/02416; A61B 5/0205; A61B 5/1118; A61B 5/02438; A61B 2562/0219; A61B 5/681; A61B 5/0002
See application file for complete search history.

(56) References Cited

U.S. PATENT DOCUMENTS

| | | | |
|---|---|---|---|
| 5,228,449 A | 7/1993 | Christ et al. | |
| 6,361,501 B1 * | 3/2002 | Amano | A61B 5/02028 600/485 |

(Continued)

FOREIGN PATENT DOCUMENTS

DE   10313837   10/2004

OTHER PUBLICATIONS

Bonnici, Timothy et al., "Testing of Wearable Monitors in a Real-World Hospital Environment. What Lessons Can Be Learnt?", 2012 Ninth International Conference on Wearable and Implantable Body Sensor Networks, IEEE, May 9, 2012, pp. 79-84.
(Continued)

*Primary Examiner* — Patricia Mallari
*Assistant Examiner* — Michael Catina
(74) *Attorney, Agent, or Firm* — Strategic Patents, P.C.

(57) ABSTRACT

Continuous monitoring of a plurality of physiological data may be used for health and fitness improvements for a user. To this end, a physiological monitoring and measurement device may include a wearable strap that receives heart rate data for a user including a time series of heart rate data, a maximum heart rate, and a resting heart rate. A processor may transform the heart rate data into a time series of heart rate reserve data that is weighted, e.g., to account for cardiovascular efficiencies at different intensity levels, to provide a weighted time series of heart rate reserve values. An intensity score that provides an indicator of cardiovascular intensity for an exercise routine may be generated from the weighted time series of heart rate reserve values and displayed to the user on the wearable strap.

16 Claims, 28 Drawing Sheets

Related U.S. Application Data

(60) Provisional application No. 61/696,525, filed on Sep. 4, 2012, provisional application No. 61/736,310, filed on Dec. 12, 2012.

(51) Int. Cl.

| | | |
|---|---|---|
| *A61B 5/024* | (2006.01) | |
| *A61B 5/00* | (2006.01) | |
| *A63B 24/00* | (2006.01) | |
| *G06F 1/16* | (2006.01) | |
| *A61B 5/0255* | (2006.01) | |
| *A61B 5/053* | (2006.01) | |
| *G06F 19/00* | (2018.01) | |

(52) U.S. Cl.
CPC .......... *A61B 5/0082* (2013.01); *A61B 5/0255* (2013.01); *A61B 5/02405* (2013.01); *A61B 5/02416* (2013.01); *A61B 5/02427* (2013.01); *A61B 5/02438* (2013.01); *A61B 5/0533* (2013.01); *A61B 5/11* (2013.01); *A61B 5/1112* (2013.01); *A61B 5/1118* (2013.01); *A61B 5/441* (2013.01); *A61B 5/4806* (2013.01); *A61B 5/4809* (2013.01); *A61B 5/4812* (2013.01); *A61B 5/4815* (2013.01); *A61B 5/681* (2013.01); *A61B 5/684* (2013.01); *A61B 5/6813* (2013.01); *A61B 5/6824* (2013.01); *A61B 5/6829* (2013.01); *A61B 5/6831* (2013.01); *A61B 5/6844* (2013.01); *A61B 5/7221* (2013.01); *A61B 5/7267* (2013.01); *A61B 5/7278* (2013.01); *A61B 5/7282* (2013.01); *A61B 5/7285* (2013.01); *A61B 5/742* (2013.01); *A61B 5/7475* (2013.01); *A63B 24/0003* (2013.01); *A63B 24/0062* (2013.01); *A63B 24/0075* (2013.01); *A63B 24/0087* (2013.01); *G06F 1/163* (2013.01); *G06F 19/3481* (2013.01); *A61B 5/4866* (2013.01); *A61B 2560/0214* (2013.01); *A61B 2560/0443* (2013.01); *A61B 2560/0475* (2013.01); *A61B 2562/0219* (2013.01); *A61B 2562/0238* (2013.01); *A61B 2562/0257* (2013.01); *A61B 2562/227* (2013.01); *A63B 2024/0065* (2013.01); *A63B 2220/803* (2013.01); *A63B 2225/50* (2013.01); *A63B 2230/06* (2013.01)

(56) References Cited

U.S. PATENT DOCUMENTS

| | | | |
|---|---|---|---|
| 6,746,370 | B1 | 6/2004 | Fleming et al. |
| 7,676,262 | B1 | 3/2010 | Xi et al. |
| 8,052,580 | B2 | 11/2011 | Saalasti et al. |
| 8,200,323 | B2 | 6/2012 | DiBenedetto et al. |
| 8,235,724 | B2 | 8/2012 | Gilley et al. |
| 8,602,988 | B2 | 12/2013 | Hunt et al. |
| 8,762,168 | B2 | 6/2014 | Tichý |
| 8,777,815 | B2 | 7/2014 | Case, Jr. et al. |
| 2004/0077462 | A1 | 4/2004 | Brown et al. |
| 2004/0102931 | A1 | 5/2004 | Ellis et al. |
| 2004/0133081 | A1 | 7/2004 | Teller et al. |
| 2005/0054940 | A1 | 3/2005 | Almen et al. |
| 2005/0202934 | A1 | 9/2005 | Olrik et al. |
| 2006/0090765 | A1 | 5/2006 | Surina |
| 2006/0136173 | A1 | 6/2006 | Case et al. |
| 2006/0228681 | A1 | 10/2006 | Clarke |
| 2007/0179350 | A1 | 8/2007 | Nadeau |
| 2007/0219059 | A1 | 9/2007 | Schwartz et al. |
| 2007/0232453 | A1 | 10/2007 | Hanoun |
| 2007/0249470 | A1 | 10/2007 | Niva et al. |
| 2007/0249949 | A1 | 10/2007 | Hadley |
| 2008/0086318 | A1 | 4/2008 | Gilley et al. |
| 2008/0109158 | A1 | 5/2008 | Huhtala et al. |
| 2008/0220940 | A1 | 9/2008 | Kasama |
| 2008/0254946 | A1 | 10/2008 | Pauws et al. |
| 2008/0261776 | A1 | 10/2008 | Skiba |
| 2008/0300498 | A1 | 12/2008 | Edwards |
| 2009/0024013 | A1* | 1/2009 | Soller ............... A61B 5/14551 600/324 |
| 2009/0069156 | A1 | 3/2009 | Kurunmäki et al. |
| 2009/0118100 | A1 | 5/2009 | Oliver et al. |
| 2009/0177097 | A1 | 7/2009 | Ma et al. |
| 2009/0216143 | A1 | 8/2009 | Tulppo et al. |
| 2009/0273478 | A1 | 11/2009 | Mei et al. |
| 2009/0275442 | A1 | 11/2009 | Nissila |
| 2009/0312658 | A1 | 12/2009 | Thieberger et al. |
| 2009/0325766 | A1* | 12/2009 | Kasama ............... A61B 5/024 482/8 |
| 2010/0076278 | A1 | 3/2010 | van der Zande et al. |
| 2011/0021319 | A1 | 1/2011 | Nissila et al. |
| 2011/0065549 | A1 | 3/2011 | Jung et al. |
| 2012/0010478 | A1 | 1/2012 | Kinnunen et al. |
| 2012/0029370 | A1 | 2/2012 | Röcker et al. |
| 2012/0035950 | A1 | 2/2012 | Tichý |
| 2012/0150047 | A1* | 6/2012 | Terumoto ........... A61B 5/02427 600/479 |
| 2012/0184829 | A1* | 7/2012 | Sekii ..................... A61B 5/021 600/323 |
| 2012/0253485 | A1 | 10/2012 | Weast et al. |
| 2014/0309542 | A1 | 10/2014 | Ahmed et al. |
| 2014/0323827 | A1 | 10/2014 | Ahmed et al. |
| 2014/0323828 | A1 | 10/2014 | Ahmed et al. |
| 2014/0323880 | A1 | 10/2014 | Ahmed et al. |
| 2014/0343372 | A1 | 11/2014 | Ahmed et al. |
| 2014/0350356 | A1 | 11/2014 | Ahmed et al. |
| 2015/0031970 | A1* | 1/2015 | Lain .................. A61B 5/14551 600/323 |

OTHER PUBLICATIONS

USPTO, "U.S. Appl. No. 14/313,537 Final Office Action dated Sep. 2, 2015", 49 pages.

USPTO, "U.S. Appl. No. 14/313,537 Non-Final Office Action dated Feb. 12, 2015", 63 pages.

International Search Authority, "PCT Application No. PCT/US13/58077 International Search Report and Written Opinion dated Feb. 18, 2014", 18 pages.

International Search Authority, "PCT Application No. PCT/US13/58077 Invitation to Pay Additional Fees with Partial Search Report dated Dec. 16, 2013", 7 Pages.

Jackowska, M. et al., "Sleep problems and heart rate variability over the working day", J. Sleep Res. Feb. 7, 2012 , pp. 434-440.

Myllymaki, Tero et al., "Effects of exercise intensity and duration on nocturnal heart rate variability and sleep quality", Eur J Appl Physiol (2012) 112. Feb. 15, 2011 , pp. 801-809.

Kageyama, T. et al., "Self-Reported Sleep Quality, Job Stress, and Daytime Autonomic Activities Assessed in Terms of Short-Term Heart Rate Variability among Male White-Collar Workers", Industrial Health 1988 , pp. 263-372.

Borg, G. A. "Psychophysical bases of perceived exertion", Medicine and Science in Sports and Exercise; vol. 14, No. 5 1982 , pp. 377-381.

USPTO, "U.S. Appl. No. 14/326,810 Non-Final Office Action dated Dec. 1, 2017", 18 pages.

ISA, "PCT Application No. PCT/US13/58077 International Search Report and Written Opinion dated Feb. 18, 2014", 20 Pages.

EPO, "EP Application No. 13766743.2 Office Action dated Jan. 24, 2017", 4 Pages.

\* cited by examiner

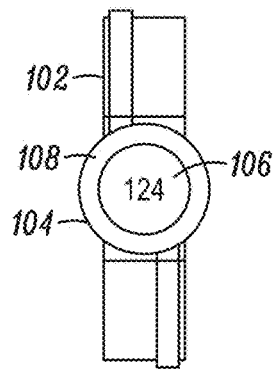
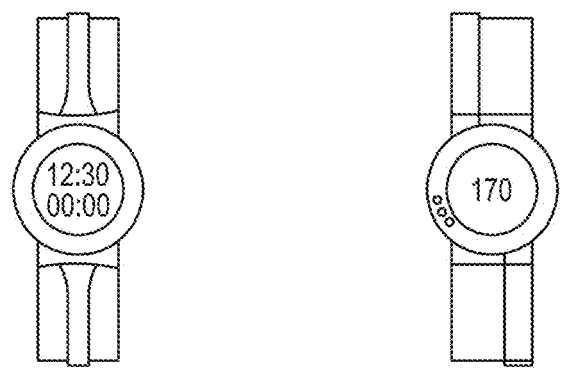
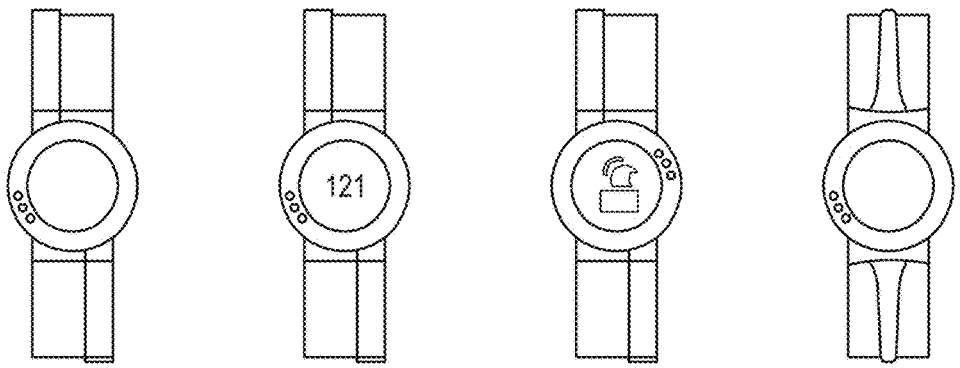
FIG. 3

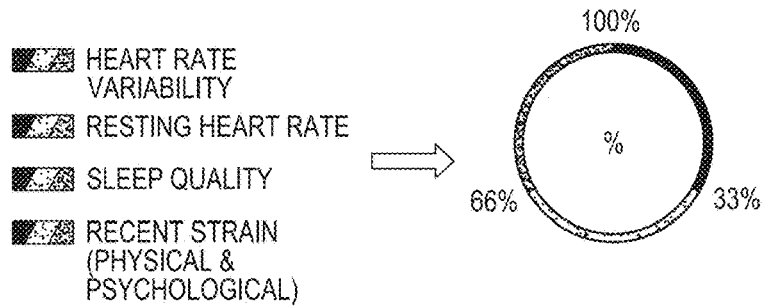
FIG. 13
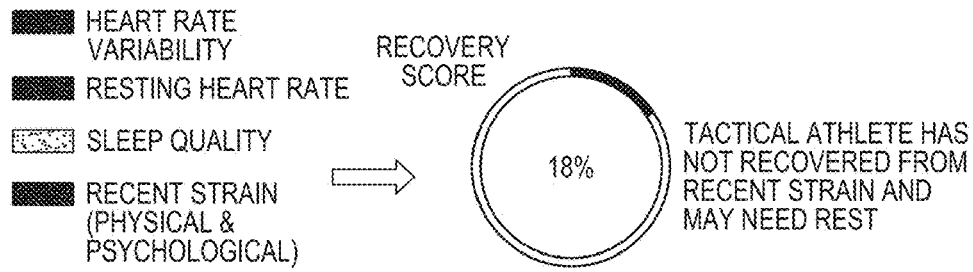
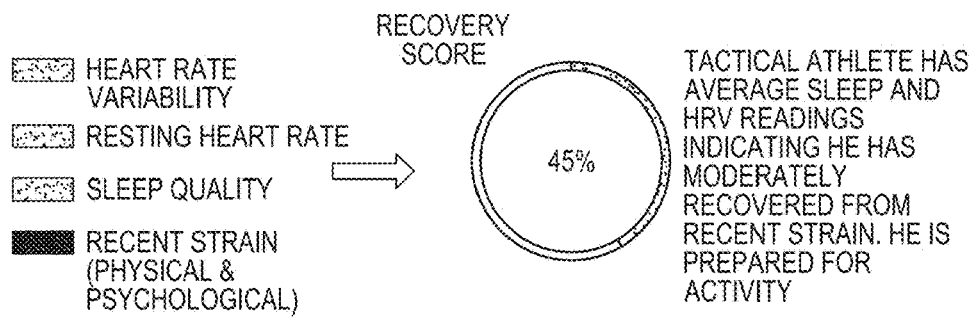
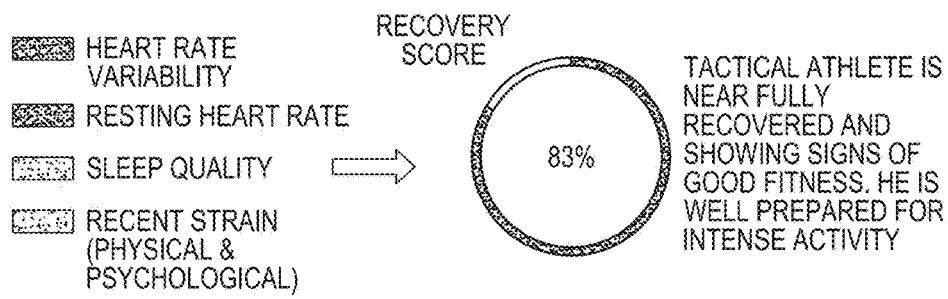
FIG. 14

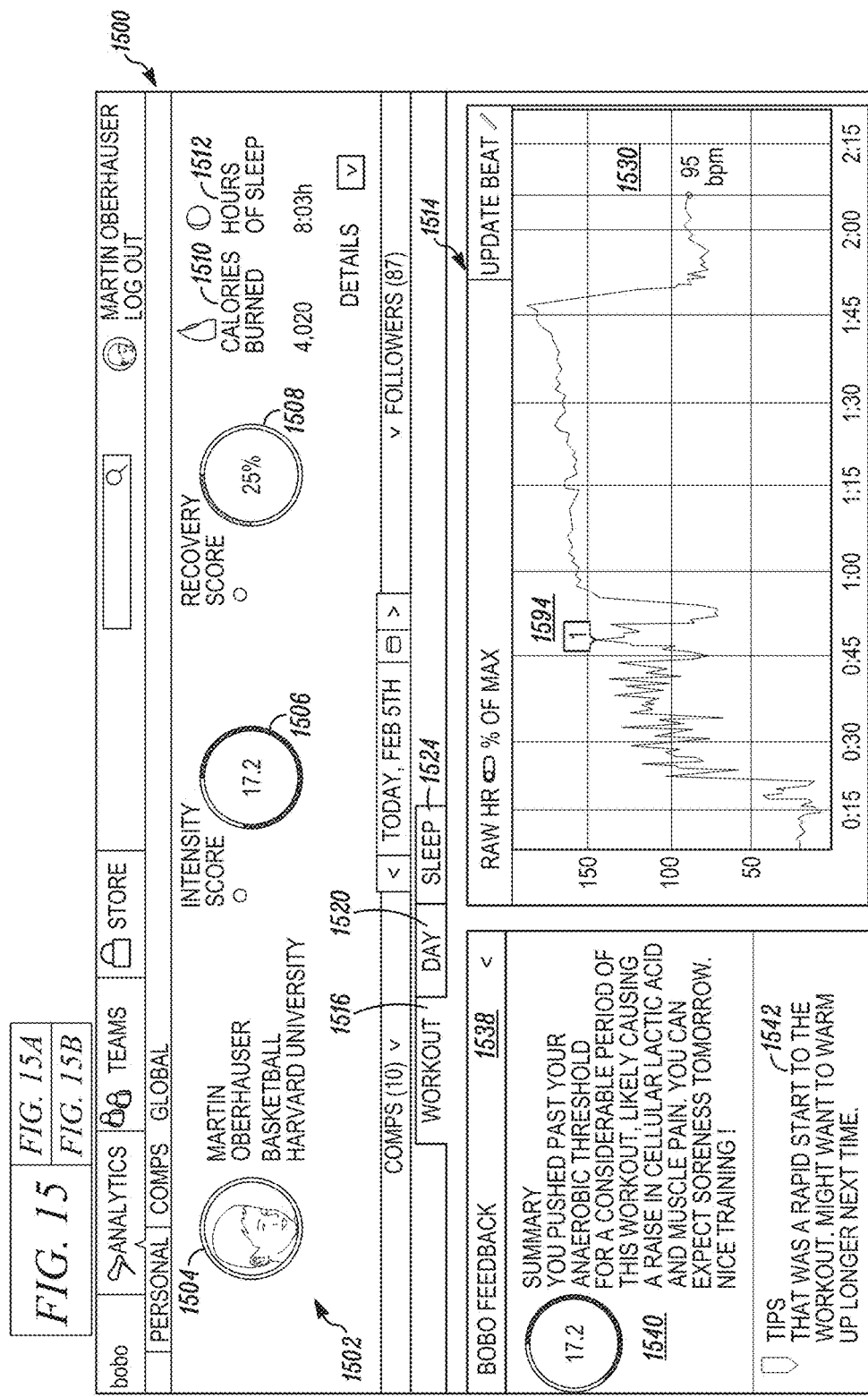

FIG. 17B

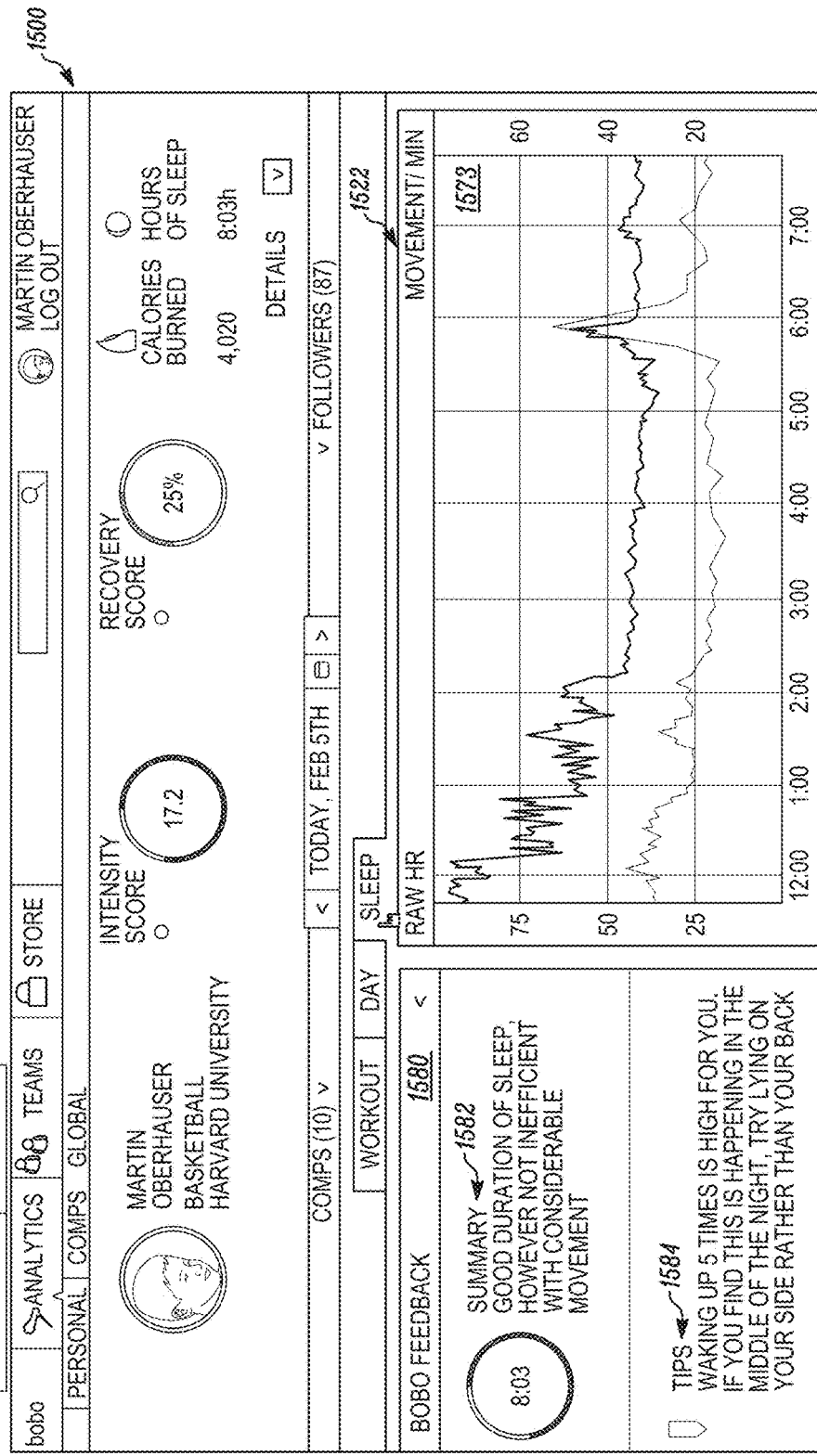

| STATS COMPARED TO LAST WEEK'S AVG *1574* | | SLEEP CYCLE | ZONE | TIME IN ZONE |
|---|---|---|---|---|
| ♡ MAX HR<br>102<br>↑7 | ♡ MIN HR<br>45<br>↑3 | | REM | 02:42h |
| | | ⌂ TOTAL<br>8:03hr | DEEP | 01:14h |
| AWAKE<br>5<br>↑1 | △ MOVEMENT<br>32/MIN<br>↓14 | *1576* | LIGHT | 04:07h |
| | | | AWAKE | 01:24h |

SLEEP DURATION    JAN 30   JAN 31   FEB 1   FEB 2   FEB 3   FEB 4   FEB 5

[8.5h TODAY] *1578*

10.0
8.0
6.0
4.0
2.0

◊ INSIGHTS ← *1586*
YOUR MAX HR IS THE HIGHEST RECORDED YET FOR SLEEP

⚠ CAUTION ← *1588*
YOUR MOVEMENTS WERE PRETTY FREQUENT LAST NIGHT, WHICH MAY BE A SIGN OF OVERTRAINING. GET A GOOD NIGHT'S SLEEP TONIGHT!

NOTES

NO COMMENTS YET

[+ ADD NOTE]

| FIG. 19A |
|----------|
| FIG. 19B |

DEVICE FOR PHYSIOLOGICAL MONITORING AND MEASUREMENT

CROSS-REFERENCE TO RELATED APPLICATIONS

This application is a continuation of U.S. patent application Ser. No. 14/326,598 filed on Jul. 9, 2014, which is a continuation of U.S. patent application Ser. No. 14/018,262 filed on Sep. 4, 2013, which claims the benefit of U.S. Provisional Patent Application No. 61/696,525 filed on Sep. 4, 2012 and U.S. Provisional Patent Application No. 61/736,310, filed on Dec. 12, 2012. The entire contents of each of the aforementioned applications are incorporated herein in their entirety by reference.

BACKGROUND

There is an increasing demand for health and fitness monitors and methods for providing health and fitness monitoring. Monitoring heart rate, for example, is important for various reasons. Monitoring heart rate is critical for athletes in understanding their fitness levels and workouts over time. Conventional techniques for monitoring heart rate have numerous drawbacks. Certain conventional heart rate monitors, for example, require the use of a chest strap or other bulky equipment that causes discomfort and prevents continuous wearing and use.

This presents a challenge to adoption and use of such monitors because the monitors are too obtrusive and/or are directed to assessing general well-being rather than continuous, around-the-clock monitoring of fitness. Certain conventional heart rate monitors do not enable continuous sensing of heart rate, thereby preventing continuous fitness monitoring and reliable analysis of physiological data. Additionally, a challenge to adoption of fitness monitors by athletes is the lack of a vibrant and interactive online community for displaying and sharing physiological data among users.

SUMMARY

Embodiments provide physiological measurement systems, devices and methods for continuous health and fitness monitoring. A wearable strap may detect reflected light from a user's skin, where data corresponding to the reflected light is used to automatically and continually determine a heart rate of the user. The wearable strap may monitor heart rate data including heart rate variability, resting heart rate, and sleep quality. The systems may include a processing module that generates an indicator of physical recovery based on the heart rate data. The recovery indicator may be used to determine strain related to an exercise routine, qualitative information on the user's health, whether to alter a user's exercise plan, and so forth.

Embodiments provide physiological measurement systems, devices and methods for continuous health and fitness monitoring. A lightweight wearable system is provided to collect various physiological data continuously from a wearer without the need for electrocardiography (ECG) equipment or a chest strap. The system also enables monitoring of one or more physiological parameters in addition to heart rate including, but not limited to, body temperature, heart rate variability, motion, sleep, stress, fitness level, recovery level, effect of a workout routine on health and fitness, caloric expenditure, global positioning system (GPS) location, altitude, and the like. Embodiments also include computer-executable instructions that, when executed, enable automatic analysis, transformation and interpretation of one or more physiological parameters to assess the cardiovascular intensity experienced by a user (embodied in an intensity score or indicator) and the user's recovery after physical exertion (embodied in a recovery score). These indicators or scores may be stored on a non-transitory computer-readable medium and displayed on a visual display device to assist a user in managing the user's health and exercise regimen.

In accordance with one exemplary embodiment, a wearable physiological measurement system is provided. The wearable physiological measurement system includes a wearable strap configured to be couplable to an appendage of a user. The strap includes one or more light emitters for emitting light toward the user's skin, one or more light detectors for receiving light reflected from the user's skin, an electronic circuit board implementing a processing module configured for analyzing data corresponding to the reflected light to automatically and continually determine a heart rate of the user, and a first set of one or more batteries for supplying electrical power to the one or more light emitters, the one or more light detectors and the electronic circuit board. The wearable physiological measurement system also includes a modular housing removably couplable to the strap. The modular housing includes a second set of one or more batteries chargeable by an external power source, the second set of batteries configured to recharge the first set of batteries in the strap. The combination of the first and second sets of batteries enables continuous monitoring of the heart rate of the user by the wearable strap.

In accordance with another exemplary embodiment, a wearable physiological measurement system is provided. The wearable physiological measurement system includes a wearable strap configured to be couplable to an appendage of a user. The strap includes one or more light emitters for emitting light toward the user's skin, one or more light detectors for receiving light reflected from the user's skin, and an electronic circuit board comprising a plurality of electronic components configured for analyzing data corresponding to the reflected light to automatically and continually determine a heart rate of the user. The circuit board includes a processing module configured to, based on one or more signals associated with the heart rate of the user, detect an identity of a portion of the user's body to which the strap is coupled, and to, based on the identity of the appendage, adjust data analysis of the reflected light to determine the heart rate of the user.

In accordance with another exemplary embodiment, a wearable physiological measurement system is provided. The wearable physiological measurement system includes a wearable strap configured to be couplable to an appendage of a user. The strap includes one or more light emitters for emitting light toward the user's skin, one or more light detectors for receiving light reflected from the user's skin, and an electronic circuit board comprising a processing module configured for analyzing data corresponding to the reflected light to automatically and continually determine a sequence of instantaneous heart rate of the user. The processing module is configured to determine the heart rate of the user by: executing one or more computer-executable instructions associated with a peak detection algorithm to process the data corresponding to the reflected light to detect a plurality of peaks associated with a plurality of beats of the user's heart, determining an R-wave-to-R-wave interval (RR interval) based on the plurality of peaks detected by the peak detection algorithm, determining a confidence level associated with the RR interval, and based on the confidence level associated with the RR interval, selecting either the peak detection algorithm or a frequency analysis algorithm to process data corresponding to the reflected light to determine the sequence of instantaneous heart rates of the user.

In accordance with another exemplary embodiment, a computer-executable method is provided for automatically and continually determining a sequence of instantaneous heart rate of the user. The method includes executing one or more computer-executable instructions associated with a peak detection algorithm to process the data corresponding to the reflected light to detect a plurality of peaks associated with a plurality of beats of the user's heart, determining an RR interval based on the plurality of peaks detected by the peak detection algorithm, determining a confidence level associated with the RR interval, and based on the confidence level associated with the RR interval, selecting either the peak detection algorithm or a frequency analysis algorithm to process data corresponding to the reflected light to determine the sequence of instantaneous heart rates of the user.

In accordance with another exemplary embodiment, one or more non-transitory computer-readable media are provided having encoded thereon computer-executable instructions for performing a method for automatically and continually determining a sequence of instantaneous heart rate of the user. The method includes executing one or more computer-executable instructions associated with a peak detection algorithm to process the data corresponding to the reflected light to detect a plurality of peaks associated with a plurality of beats of the user's heart, determining an RR interval based on the plurality of peaks detected by the peak detection algorithm, determining a confidence level associated with the RR interval, and based on the confidence level associated with the RR interval, selecting either the peak detection algorithm or a frequency analysis algorithm to process data corresponding to the reflected light to determine the sequence of instantaneous heart rates of the user.

In accordance with another exemplary embodiment, a wearable physiological measurement system is provided. The wearable physiological measurement system includes a wearable strap configured to be couplable to an appendage of a user. The strap includes one or more light emitters for emitting light toward the user's skin, one or more light detectors for receiving light reflected from the user's skin, and an electronic circuit board comprising a plurality of electronic components configured for analyzing data corresponding to the reflected light to automatically determine a heart rate of the user. The plurality of electronic components of the electronic circuit board are assembled as a multi-chip module within the strap such that a first set of the components is provided as a first electronic circuit board and a second set of the components is provided as a second electronic circuit board, and wherein one or more electrical connections are provided between the first and second electronic circuit boards.

In accordance with another exemplary embodiment, a wearable physiological measurement system is provided. The wearable physiological measurement system includes a plurality of light emitters for emitting light toward the user's skin, a plurality of light detectors for receiving light reflected from the user's skin, a motion sensor for detecting a motion of the user, and a processing module configured to determine a motion status of the user based on data received from the motion sensor, and based on the motion status of the user, automatically and selectively activate one or more of the light emitters to determine a heart rate of the user.

In accordance with another exemplary embodiment, a computer-executable method is provided for use in detecting a heart rate of a user. The method includes determining a motion status of the user based on data received from a motion sensor, and based on the motion status of the user, automatically and selectively activating one or more light emitters to determine a heart rate of the user.

In accordance with another exemplary embodiment, one or more non-transitory computer-readable media are provided having encoded thereon computer-executable instructions for performing a method. The method includes determining a motion status of the user based on data received from a motion sensor, and based on the motion status of the user, automatically and selectively activating one or more light emitters to determine a heart rate of the user.

In accordance with another exemplary embodiment, a wearable physiological measurement system is provided. The wearable physiological measurement system includes a plurality of light emitters for emitting light toward the user's skin, a plurality of light detectors for receiving light reflected from the user's skin, a motion sensor for detecting a motion of the user, and a processing module configured to determine a heart rate of the user based on light received by one or more of the light detectors, wherein the processing module is further configured to: process one or more signals generated by at least one of the sensors, and based on the one or more processed signals, automatically adjust an operational characteristic of one or more of the light emitters and/or one or more of the light detectors to minimize consumption of power by the wearable physiological measurement system.

In accordance with another exemplary embodiment, a computer-executable method is provided for use in detecting a heart rate of a user. The method includes processing one or more signals generated by at least one sensor, and based on the one or more processed signals, automatically adjusting an operational characteristic of one or more light emitters and/or one or more light detectors to minimize consumption of power by a wearable physiological measurement system collecting heart rate data.

In accordance with another exemplary embodiment, one or more non-transitory computer-readable media are provided having encoded thereon computer-executable instructions for performing a method. The method includes processing one or more signals generated by at least one sensor, and based on the one or more processed signals, automatically adjusting an operational characteristic of one or more light emitters and/or one or more light detectors to minimize consumption of power by a wearable physiological measurement system collecting heart rate data.

In accordance with another exemplary embodiment, a computer-executable method is provided for determining an indicator of cardiovascular intensity experienced by a user. The method includes programmatically receiving, using a computer system, data corresponding to heart rate of a user during an exercise routine, transforming the heart rate data to a time series of heart rate reserve data using a processing module of the computer system, weighting the heart rate reserve data according to a weighting scheme using the processing module of the computer system, programmatically generating, using the processing module of the computer system, an indicator of cardiovascular intensity based on the weighted heart rate reserve data, and displaying, on a user interface rendered on a display device of the computer system, the indicator of cardiovascular intensity.

In accordance with another exemplary embodiment, one or more non-transitory computer-readable media are provided having encoded thereon computer-executable instructions for performing a method. The method includes programmatically receiving, using a computer system, data corresponding to heart rate of a user during an exercise routine, transforming the heart rate data to a time series of heart rate reserve data using a processing module of the computer system, weighting the heart rate reserve data according to a weighting scheme using the processing module of the computer system, programmatically generating, using the processing module of the computer system, an indicator of cardiovascular intensity based on the weighted heart rate reserve data, and displaying, on a user interface rendered on a display device of the computer system, the indicator of cardiovascular intensity.

In accordance with another exemplary embodiment, a computer system is provided for determining an indicator of cardiovascular intensity experienced by a user. The computer system includes a processing module configured or programmed for programmatically receiving data corresponding to heart rate of a user during an exercise routine, transforming the heart rate data to a time series of heart rate reserve data, weighting the heart rate reserve data according to a weighting scheme, and programmatically generating an indicator of cardiovascular intensity based on the weighted heart rate reserve data. The computer system also includes a display device for rendering a user interface on which the indicator is displayed.

In accordance with another exemplary embodiment, a computer-executable method is provided for determining an indicator of physical recovery of a user. The method includes programmatically receiving a heart rate variability of a user using a computer system, programmatically receiving a resting heart rate of the user using the computer system, programmatically receiving a sleep quality indicator of the user using the computer system, programmatically generating, using a processing module of the computer system, a recovery indicator of physical recovery of the user based on the heart rate variability, the resting heart rate and the sleep quality indicator, and displaying, on a user interface rendered on a visual display device of the computer system, the recovery indicator.

In accordance with another exemplary embodiment, one or more non-transitory computer-readable media are provided having encoded thereon computer-executable instructions for performing a method. The method includes programmatically receiving a heart rate variability of a user using a computer system, programmatically receiving a resting heart rate of the user using the computer system, programmatically receiving a sleep quality indicator of the user using the computer system, programmatically generating, using a processing module of the computer system, a recovery indicator of physical recovery of the user based on the heart rate variability, the resting heart rate and the sleep quality indicator, and displaying, on a user interface rendered on a visual display device of the computer system, the recovery indicator.

In accordance with another exemplary embodiment, a computer system is provided for determining an indicator of physical recovery of a user. The computer system includes a processing module configured or programmed for programmatically receiving a heart rate variability of a user, programmatically receiving a resting heart rate of the user, programmatically receiving a sleep quality indicator of the user, and programmatically generating a recovery indicator of physical recovery of the user based on the heart rate variability, the resting heart rate and the sleep quality indicator. The computer system also includes a display device for rendering a user interface on which the indicator is displayed.

BRIEF DESCRIPTION OF THE DRAWINGS

The foregoing and other objects, aspects, features and advantages of exemplary embodiments will be more fully understood from the following description when read together with the accompanying drawings, in which:

FIGS. 2-4 illustrate various exemplary embodiments of a wearable physiological measurement system according to aspects disclosed herein.

FIG. 13 illustrates an exemplary display of a recovery score index indicated in a circular graphic component with a first threshold of 66% and a second threshold of 33% indicated.

FIGS. 14A-14C illustrate a recovery score graphic component with exemplary recovery scores and qualitative information corresponding to the recovery scores.

Figure 17B:
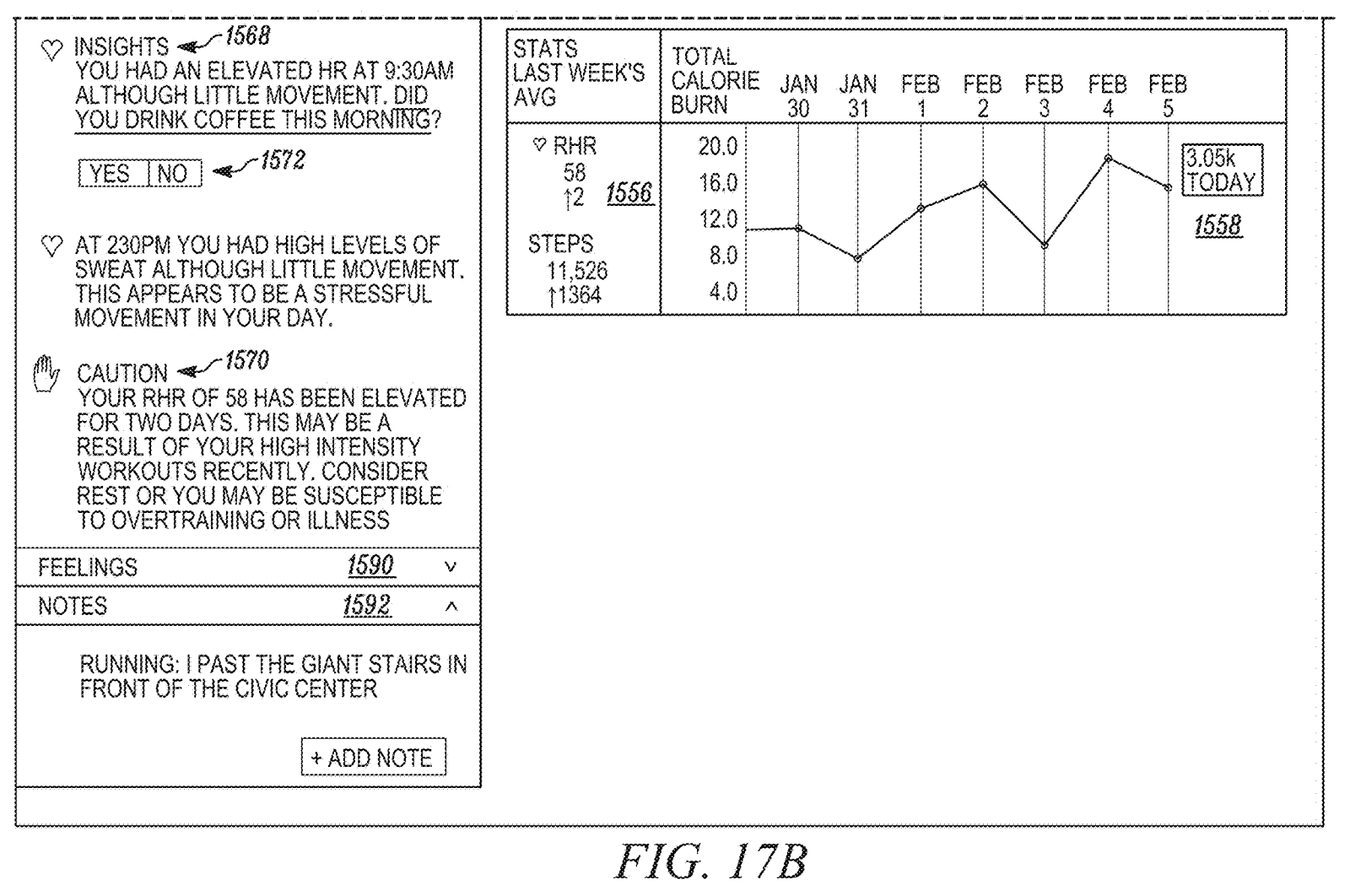

FIGS. 15A-18B illustrate exemplary user interfaces rendered on visual display device for displaying physiological data associated with a user.

FIGS. 19A and 19B illustrate an exemplary user interface rendered on a visual display device for displaying physiological data associated with a plurality of users.

FIG. 20 illustrates a user interface that may be used to independently select time periods of data for multiple users so that data from the selected periods may be displayed together.

Figure 1:
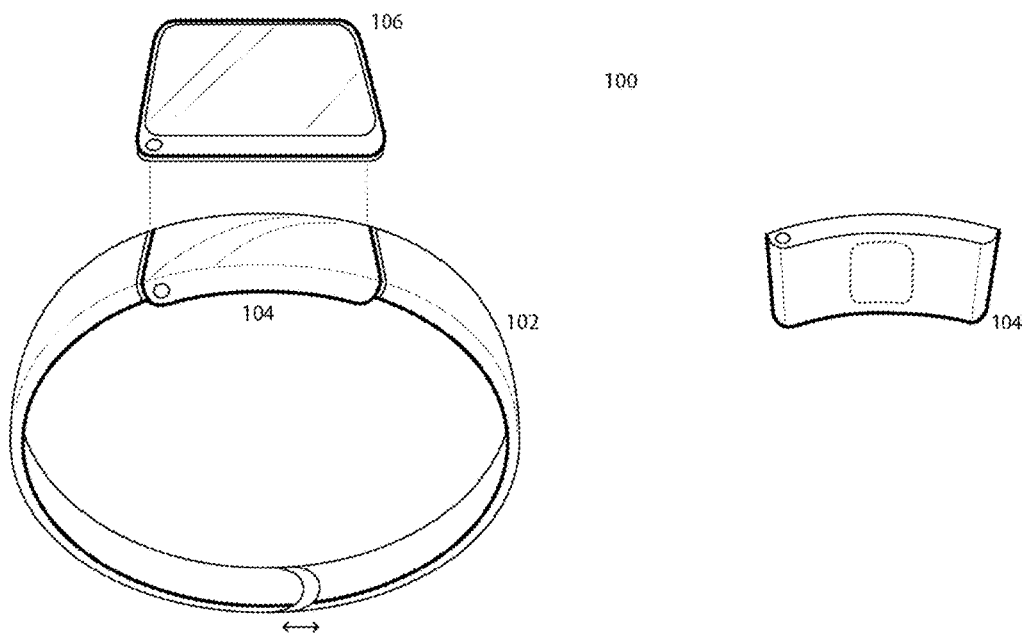
FIG. 1 illustrates a perspective view of an exemplary embodiment of a wearable physiological measurement system configured as a bracelet including a strap and a modular head portion.

The accompanying drawings are not intended to be drawn to scale.

DETAILED DESCRIPTION

Exemplary embodiments provide physiological measurement systems, devices and methods for continuous health and fitness monitoring, and provide improvements to overcome the drawbacks of conventional heart rate monitors. One aspect of the present disclosure is directed to providing a lightweight wearable system with a strap that collects various physiological data or signals from a wearer. The strap may be used to position the system on an appendage or extremity of a user, for example, wrist, ankle, and the like. Exemplary systems are wearable and enable real-time and continuous monitoring of heart rate without the need for a chest strap or other bulky equipment which could otherwise cause discomfort and prevent continuous wearing and use. The system may determine the user's heart rate without the use of electrocardiography and without the need for a chest strap. Exemplary systems can thereby be used in not only assessing general well-being but also in continuous monitoring of fitness. Exemplary systems also enable monitoring of one or more physiological parameters in addition to heart rate including, but not limited to, body temperature, heart rate variability, motion, sleep, stress, fitness level, recovery level, effect of a workout routine on health and fitness, caloric expenditure, and the like.

A health or fitness monitor that includes bulky components may hinder continuous wear. Existing fitness monitors often include the functionality of a watch, thereby making the health or fitness monitor quite bulky and inconvenient for continuous wear. Accordingly, one aspect of the present invention is directed to providing a wearable health or fitness system that does not include bulky components, thereby making the bracelet slimmer, unobtrusive and appropriate for continuous wear. The ability to continuously wear the bracelet further allows continuous collection of physiological data, as well as continuous and more reliable health or fitness monitoring. For example, embodiments of the bracelet disclosed herein allow users to monitor data at all times, not just during a fitness session. In some embodiments, the wearable system may or may not include a display screen for displaying heart rate and other information. In other embodiments, the wearable system may include one or more light emitting diodes (LEDs) to provide feedback to a user and display heart rate selectively. In some embodiments, the wearable system may include a removable or releasable modular head that may provide additional features and may display additional information. Such a modular head can be releasably installed on the wearable system when additional information display is desired, and removed to improve the comfort and appearance of the wearable system. In other embodiments, the head may be integrally formed in the wearable system.

Exemplary embodiments also include computer-executable instructions that, when executed, enable automatic interpretation of one or more physiological parameters to assess the cardiovascular intensity experienced by a user (embodied in an intensity score or indicator) and the user's recovery after physical exertion or daily stress given sleep and other forms of rest (embodied in a recovery score). These indicators or scores may be stored and displayed in a meaningful format to assist a user in managing his health and exercise regimen. Exemplary computer-executable instructions may be provided in a cloud implementation.

Exemplary embodiments also provide a vibrant and interactive online community, in the form of a website, for displaying and sharing physiological data among users. A user of the website may include an individual whose health or fitness is being monitored, such as an individual wearing a wearable system disclosed herein, an athlete, a sports team member, a personal trainer or a coach. In some embodiments, a user may pick his/her own trainer from a list to comment on their performance. Exemplary systems have the ability to stream all physiological information wirelessly, directly or through a mobile communication device application, to an online website using data transfer to a cell phone/computer. The website allows users to monitor their own fitness results, share information with their teammates and coaches, compete with other users, and win status. Both the wearable system and the website allows a user to provide feedback regarding his/her day, exercise and/or sleep, which enables recovery and performance ratings.

In an exemplary technique of data transmission, data collected by a wearable system may be transmitted directly to a cloud-based data storage, from which data may be downloaded for display and analysis on a website. In another exemplary technique of data transmission, data collected by a wearable system may be transmitted via a mobile communication device application to a cloud-based data storage, from which data may be downloaded for display and analysis on a website.

In some embodiments, the website may be a social networking site. In some embodiments, the website may be displayed using a mobile website or a mobile application. In some embodiments, the website may be configured to communicate data to other websites or applications. In some embodiments, the website may be configured to provide an interactive user interface. The website may be configured to display results based on analysis on physiological data received from one or more devices. The website may be configured to provide competitive ways to compare one user to another, and ultimately a more interactive experience for the user. For example, in some embodiments, instead of merely comparing a user's physiological data and performance relative to that user's past performances, the user may be allowed to compete with other users and the user's performance may be compared to that of other users.

I. DEFINITIONS OF TERMS

Certain terms are defined below to facilitate understanding of exemplary embodiments.

The term "user" as used herein, refers to any type of animal, human or non-human, whose physiological information may be monitored using an exemplary wearable physiological monitoring system.

The term "body," as used herein, refers to the body of a user.

The term "continuous," as used herein in connection with heart rate data collection, refers to collection of heart rate data at a sufficient frequency to enable detection of every heart beat and also refers to collection of heart rate data continuously throughout the day and night.

The term "pointing device," as used herein, refers to any suitable input interface, specifically, a human interface device, that allows a user to input spatial data to a computing system or device. In an exemplary embodiment, the pointing device may allow a user to provide input to the computer using physical gestures, for example, pointing, clicking, dragging, dropping. Exemplary pointing devices may include, but are not limited to, a mouse, a touchpad, a touchscreen, and the like.

The term "multi-chip module," as used herein, refers to an electronic package in which multiple integrated circuits (IC) are packaged with a unifying substrate, facilitating their use as a single component, i.e., as a higher processing capacity IC packaged in a much smaller volume.

The term "computer-readable medium," as used herein, refers to a non-transitory storage hardware, non-transitory storage device or non-transitory computer system memory that may be accessed by a controller, a microcontroller, a computational system or a module of a computational system to encode thereon computer-executable instructions or software programs. The "computer-readable medium" may be accessed by a computational system or a module of a computational system to retrieve and/or execute the computer-executable instructions or software programs encoded on the medium. The non-transitory computer-readable media may include, but are not limited to, one or more types of hardware memory, non-transitory tangible media (for example, one or more magnetic storage disks, one or more optical disks, one or more USB flash drives), computer system memory or random access memory, such as, dynamic random-access memory (DRAM), static random-access memory (SRAM), extended data output random-access memory (EDO RAM), and the like.

The term "distal," as used herein, refers to a portion, end or component of a physiological measurement system that is farthest from a user's body when worn by the user.

The term "proximal," as used herein, refers to a portion, end or component of a physiological measurement system that is closest to a user's body when worn by the user.

The term "equal," as used herein, refers, in a broad lay sense, to exact equality or approximate equality within some tolerance.

II. EXEMPLARY WEARABLE PHYSIOLOGICAL MEASUREMENT SYSTEMS

Exemplary embodiments provide wearable physiological measurements systems that are configured to provide continuous measurement of heart rate. Exemplary systems are configured to be continuously wearable on an appendage, for example, wrist or ankle, and do not rely on electrocardiography or chest straps in detection of heart rate. The exemplary system includes one or more light emitters for emitting light at one or more desired frequencies toward the user's skin, and one or more light detectors for received light reflected from the user's skin. The light detectors may include a photo-resistor, a photo-transistor, a photo-diode, and the like. As light from the light emitters (for example, green light) pierces through the skin of the user, the blood's natural absorbance or transmittance for the light provides fluctuations in the photo-resistor readouts. These waves have the same frequency as the user's pulse since increased absorbance or transmittance occurs only when the blood flow has increased after a heartbeat. The system includes a processing module implemented in software, hardware or a combination thereof for processing the optical data received at the light detectors and continuously determining the heart rate based on the optical data. The optical data may be combined with data from one or more motion sensors, e.g., accelerometers and/or gyroscopes, to minimize or eliminate noise in the heart rate signal caused by motion or other artifacts.

Figure 2:
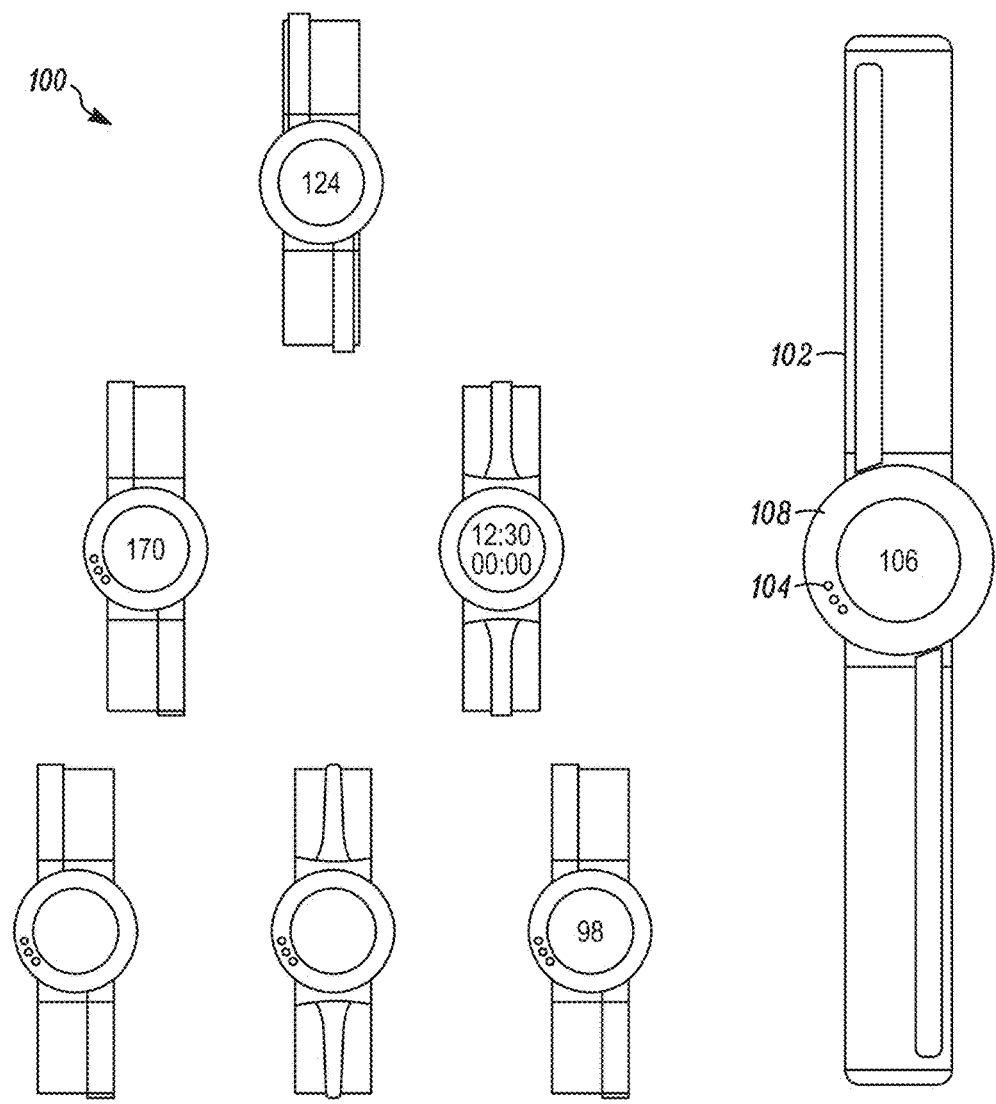
Figure 4:
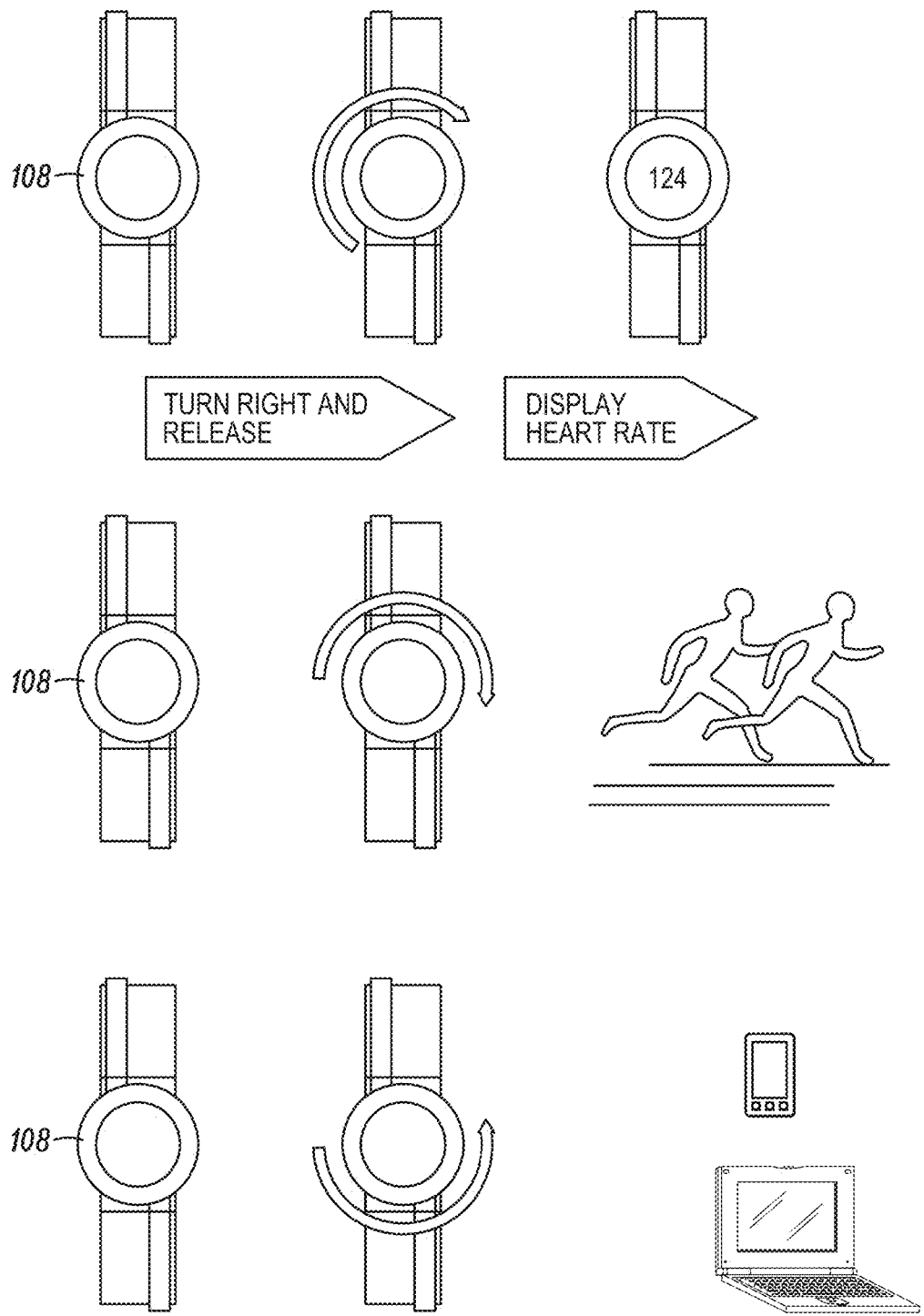

FIG. 1 illustrates front and back perspective views of one embodiment of a wearable system configured as a bracelet 100 including one or more straps 102. FIGS. 2 and 3 show various exemplary embodiments of a bracelet according to aspects disclosed herein. FIG. 4 illustrates an exemplary user interface of a bracelet. The bracelet is sleek and lightweight, thereby making it appropriate for continuous wear. The bracelet may or may not include a display screen, e.g., a screen 106 such as a light emitting diode (LED) display for displaying any desired data (e.g., instantaneous heart rate), as shown and described below with reference to the exemplary embodiments in FIGS. 2-4.

Figure 5:
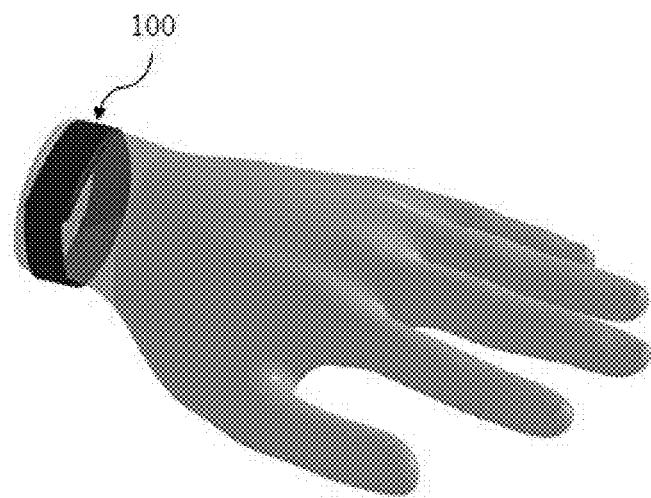
FIG. 5 illustrates placement of an exemplary wearable physiological measurement system configured as a bracelet on a user's wrist.

As shown in the non-limiting embodiment in FIG. 1, the strap 102 of the bracelet may have a wider side and a narrower side. In one embodiment, a user may simply insert the narrower side into the thicker side and squeeze the two together until the strap is tight around the wrist, as shown in FIG. 5. To remove the strap, a user may push the strap further inwards, which unlocks the strap and allows it to be released from the wrist. In other embodiments, various other fastening means may be provided. In some embodiments, the strap of the bracelet may be a slim elastic band formed of any suitable elastic material, for example, rubber. Certain embodiments of the wearable system may be configured to have one size that fits all. Other embodiments may provide the ability to adjust for different wrist sizes.

As shown in FIG. 1, the wearable system may include components configured to provide various functions such as data collection and streaming functions of the bracelet. In some embodiments, the wearable system may include a button underneath the wearable system. In some embodiments, the button may be configured such that, when the wearable system is properly tightened to one's wrist as shown in FIG. 3A, the button may press down and activate the bracelet to begin storing information. In other embodiments, the button may be disposed and configured such that it may be pressed manually at the discretion of a user to begin storing information or otherwise to mark the start or end of an activity period. In some embodiments, the button may be held to initiate a time-stamp and held again to end a time-stamp, which may be transmitted, directly or through a mobile communication device application, to a website as a time-stamp. Time-stamp information may be used, for example, as a privacy setting to indicate periods of activity during which physiological data may not be shared with other users. In some embodiments, the wearable system may be waterproof so that users never need to remove it, thereby allowing for continuous wear.

The wearable system includes a heart rate monitor. In one example, the heart rate may be detected from the radial artery, in the exemplary positioning shown in FIG. 5. See, Certified Nursing Association, "Regular monitoring of your patient's radial pulse can help you detect changes in their condition and assist in providing potentially life-saving care." See, http://cnatraininghelp.com/cna-skills/counting-and-recording-a-radial-pulse, the entire contents of which are incorporated herein by reference. Thus, the wearable system may include a pulse sensor. In one embodiment, the wearable system may be configured such that, when a user wears it around their wrist and tightens it, the sensor portion of the wearable system is secured over the user's radial artery or other blood vessel. Secure connection and placement of the pulse sensor over the radial artery or other blood vessel allow measurement of heart rate and pulse.

In some embodiments, the pulse or heart rate may be taken using an optical sensor coupled with one or more light emitting diodes (LEDs), all directly in contact with the user's wrist. The LEDs are provided in a suitable position from which light can be emitted into the user's skin. In one example, the LEDs mounted on a side or top surface of a circuit board in the system to prevent heat buildup on the LEDs and to prevent burns on the skin. Cleverly designed elastic wrist straps can ensure that the sensors are always in contact with the skin and that there is a minimal amount of outside light seeping into the sensors.

In some embodiments, the wearable system may be configured to record other physiological parameters including, but not limited to, skin temperature (using a thermometer), galvanic skin response (using a galvanic skin response sensor), motion (using one or more multi-axes accelerometers and/or gyroscope), and the like, and environmental or contextual parameters, e.g., ambient temperature, humidity, time of day, and the like.

In some embodiments, the wearable system may further be configured such that a button underneath the system may be pressed against the user's wrist, thus triggering the system to begin one or more of collecting data, calculating metrics and communicating the information to a network. In some embodiments, the same sensor used for measuring heart rate may be used to indicate whether the user is wearing the wearable system or not. In some embodiments, power to the one or more LEDs may be cut off as soon as this situation is detected, and reset once the user has put the wearable system back on their wrist.

The wearable system may include one, two or more sources of battery life. In some embodiments, it may have a battery that can slip in and out of the head of the wearable system and can be recharged using an included accessory. Additionally, the wearable system may have a built-in battery that is less powerful. When the more powerful battery is being charged, the user does not need to remove the wearable system and can still record data (during sleep, for example).

In some embodiments, the an application associated with data from an exemplary wearable system (e.g., a mobile communication device application) may include a user input component for enabling the user to indicate his/her feelings. When the data is uploaded from the wearable system directly or indirectly to a website, the website may record a user's "Vibes" alongside their duration of exercise and sleep.

In exemplary embodiments, the wearable system is enabled to automatically detect when the user is asleep, awake but at rest and exercising based on physiological data collected by the system.

As shown in the exemplary embodiment of FIG. 4, a rotatable wheel 108 may be provided at the center of the wearable system to control whether the system is displaying the heart rate. For example, when the wheel is turned to the right however, the system continuously shows heart rate, and turns off the heart rate display when the wheel is turned to the right again. In one example, turning the wheel to the right and holding it there creates a time-stamp to indicate the duration of exercise. Turning the wheel to the left and holding it there forces data transmission to a cell phone, external computer or the Internet. In other embodiments, the wheel 108 may be absent in the wearable system. In some embodiments, the functionality of a rotatable wheel described herein may be provided in an application of a mobile communication device that is associated with physiological data collected from a wearable system.

Figure 6:
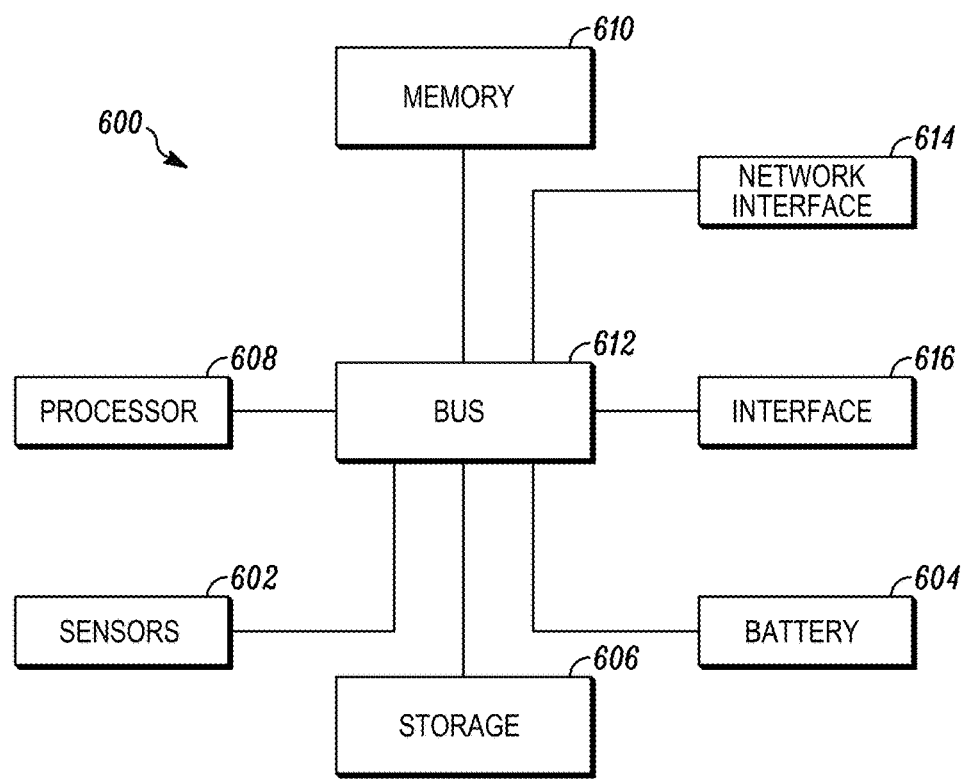
FIG. 6 shows a block diagram illustrating exemplary components of a wearable physiological measurement system configured to provide continuous collection and monitoring of physiological data.

FIG. 6 shows a block diagram illustrating exemplary components of a wearable physiological measurement system 600 configured to provide continuous collection and monitoring of physiological data. The wearable system 600 includes one or more sensors 602. As discussed above, the sensors 602 may include a heart rate monitor. In some embodiments, the wearable system 600 may further include one or more of sensors for detecting calorie burn, distance and activity. Calorie burn may be based on a user's heart rate, and a calorie burn measurement may be improved if a user chooses to provide his or her weight and/or other physical parameters. In some embodiments, manual entering of data is not required in order to derive calorie burn; however, data entry may be used to improve the accuracy of the results. In some embodiments, if a user has forgotten to enter a new weight, he/she can enter it for past weeks and the calorie burn may be updated accordingly.

The sensors 602 may include one or more sensors for activity measurement. In some embodiments, the system may include one or more multi-axes accelerometers and/or gyroscope to provide a measurement of activity. In some embodiments, the accelerometer may further be used to filter a signal from the optical sensor for measuring heart rate and to provide a more accurate measurement of the heart rate. In some embodiments, the wearable system may include a multi-axis accelerometer to measure motion and calculate distance, whether it be in real terms as steps or miles or as a converted number. Activity sensors may be used, for example, to classify or categorize activity, such as walking, running, performing another sport, standing, sitting or lying down. In some embodiments, one or more of collected physiological data may be aggregated to generate an aggregate activity level. For example, heart rate, calorie burn, and distance may be used to derive an aggregate activity level. The aggregate level may be compared with or evaluated relative to previous recordings of the user's aggregate activity level, as well as the aggregate activity levels of other users.

The sensors 602 may include a thermometer for monitoring the user's body or skin temperature. In one embodiment, the sensors may be used to recognize sleep based on a temperature drop, lack of activity according to data collected by the accelerometer, and reduced heart rate as measured by the heart rate monitor. The body temperature, in conjunction with heart rate monitoring and motion, may be used to interpret whether a user is sleeping or just resting, as body temperature drops significantly when an individual is about to fall asleep), and how well an individual is sleeping as motion indicates a lower quality of sleep. The body temperature may also be used to determine whether the user is exercising and to categorize and/or analyze activities.

The system 600 includes one or more batteries 604. According to one embodiment, the one or more batteries may be configured to allow continuous wear and usage of the wearable system. In one embodiment, the wearable system may include two or more batteries. The system may include a removable battery that may be recharged using a charger. In one example, the removable battery may be configured to slip in and out of a head portion of the system. In one example, the removable battery may be able to power the system for around a week. Additionally, the system may include a built-in battery. The built-in battery may be recharged by the removable battery. The built-in battery may be configured to power the bracelet for around a day on its own. When the more removable battery is being charged, the user does not need to remove the system and may continue collecting data using the built-in battery. In other embodiments, the two batteries may both be removable and rechargeable.

In some embodiments, the system 600 may include a battery that is a wireless rechargeable battery. For example, the battery may be recharged by placing the system or the battery on a rechargeable mat. In other example, the battery may be a long range wireless rechargeable battery. In other embodiments, the battery may be a rechargeable via motion. In yet other embodiments, the battery may be rechargeable using a solar energy source.

The wearable system 600 includes one or more non-transitory computer-readable media 606 for storing raw data detected by the sensors of the system and processed data calculated by a processing module of the system.

The system 600 includes a processor 608, a memory 610, a bus 612, a network interface 614 and an interface 616. The network interface 614 is configured to wirelessly communicate data to an external network. Some embodiments of the wearable system may be configured to stream information wirelessly to a social network. In some embodiments, data streamed from a user's wearable system to an external network may be accessed by the user via a website. The network interface may be configured such that data collected by the system may be streamed wirelessly. In some embodiments, data may be transmitted automatically, without the need to manually press any buttons. In some embodiments, the system may include a cellular chip built into the system. In one example, the network interface may be configured to stream data using Bluetooth technology. In another example, the network interface may be configured to stream data using a cellular data service, such as via a 3G or 4G cellular network.

Figure 7A:
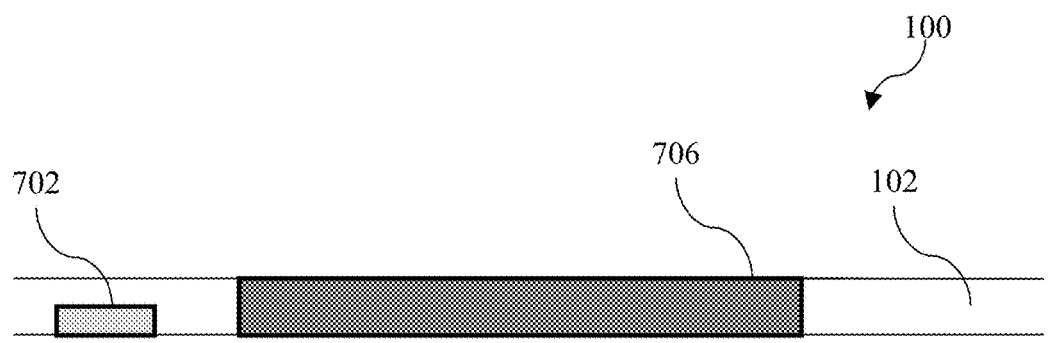
FIG. 7A illustrates a sectional side view of an exemplary physiological measurement system including a strap that is not coupled to a modular head portion.
Figure 7B:
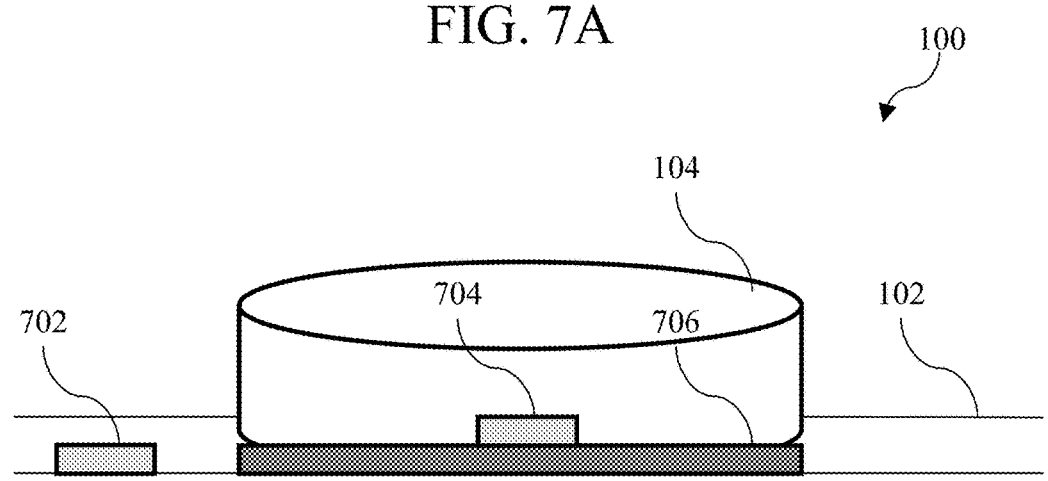
FIG. 7B illustrates a sectional side view of the system of FIG. 7A in which a modular head portion is removably coupled to the strap.

In some embodiments, a physiological measurement system may be configured in a modular design to enable continuous operation of the system in monitoring physiological information of a user wearing the system. The module design may include a strap and a separate modular head portion or housing that is removably couplable to the strap. FIG. 7A illustrates a side view of an exemplary physiological measurement system 100 including a strap 102 that is not coupled to a modular head portion or housing 104. FIG. 7B illustrates a side view of the system 100 in which the modular head portion 104 is removably coupled to the strap 102.

In the non-limiting illustrative module design, the strap 102 of a physiological measurement system may be provided with a set of components that enables continuous monitoring of at least a heart rate of the user so that it is independent and fully self-sufficient in continuously monitoring the heart rate without requiring the modular head portion 104. In one embodiment, the strap includes a plurality of light emitters for emitting light toward the user's skin, a plurality of light detectors for receiving light reflected from the user's skin, an electronic circuit board comprising a plurality of electronic components configured for analyzing data corresponding to the reflected light to automatically and continually determine a heart rate of the user, and a first set of one or more batteries for supplying electrical power to the light emitters, the light detectors and the electronic circuit board. In some embodiments, the strap may also detect one or more other physiological characteristics of the user including, but not limited to, temperature, galvanic skin response, and the like. The strap may include one or more slots for permanently or removably coupling batteries 702 to the strap 102.

The strap 102 may include an attachment mechanism 706, e.g., a press-fit mechanism, for coupling the modular head portion 104 to the strap 102. The modular head portion 104 may be coupled to the strap 102 at any desired time by the user to impart additional functionality to the system 100. In one embodiment, the modular head portion 104 includes a second set of one or more batteries 704 chargeable by an external power source so that the second set of batteries can be used to charge or recharge the first set of batteries 702 in the strap 102. The combination of the first and second sets of batteries enables the user to continuously monitor his/her physiological information without having to remove the strap for recharging. In some embodiments, the module head portion may include one or more additional components including, but not limited to, an interface 616 including visual display device configured to render a user interface for displaying physiological information of the user, a global positioning system (GPS) sensor, an electronic circuit board (e.g., to process GPS signals), and the like.

Certain exemplary systems may be configured to be coupled to any desired part of a user's body so that the system may be moved from one portion of the body (e.g., wrist) to another portion of the body (e.g., ankle) without affecting its function and operation. An exemplary system may include an electronic circuit board comprising a plurality of electronic components configured for analyzing data corresponding to the reflected light to automatically and continually determine a heart rate of the user. The electronic circuit board implements a processing module configured to detect an identity of a portion of the user's body, for example, an appendage like wrist, ankle, to which the strap is coupled based on one or more signals associated with the heart rate of the user, and, based on the identity of the appendage, adjust data analysis of the reflected light to determine the heart rate of the user.

In one embodiment, the identity of the portion of the user's body to which the wearable system is attached may be determined based on one or more parameters including, but not limited to, absorbance level of light as returned from the user's skin, reflectance level of light as returned from the user's skin, motion sensor data (e.g., accelerometer and/or gyroscope), altitude of the wearable system, and the like.

In some embodiments, the processing module is configured to determine that the wearable system is taken off from the user's body. In one example, the processing module may determine that the wearable system has been taken off if data from the galvanic skin response sensor indicates data atypical of a user's skin. If the wearable system is determined to be taken off from the user's body, the processing module is configured to deactivate the light emitters and the light detectors and cease monitoring of the heart rate of the user to conserve power.

In some exemplary embodiments, the electronic components of the physiological measurement system may be provided in the form of a multi-chip module in which a plurality of electrically-coupled electronic circuit boards are provided separately within the system. In one non-limiting example, the processor and random-access memory (RAM) may be provided on a first circuit board, wireless communication components may be provided on a second circuit board, and sensors may be provided on a third circuit board. The separate electronic circuit boards may be provided in a modular head of the system and/or along a strap of the system. The term "multi-chip module," as used herein, refers to an electronic package in which multiple integrated circuits (IC) are packaged with a unifying substrate, facilitating their use as a single component, i.e., as a higher processing capacity IC packaged in a much smaller volume. Each IC can comprise a circuit fabricated in a thinned semiconductor wafer. Any suitable set of one or more electronic components may be provided in the circuit boards of a multi-chip module. Exemplary embodiments also provide methods for fabricating and assembling multi-chip modules as taught herein.

Exemplary numbers of chips integrated in a multi-chip module may include, but are not limited to, two, three, four, five, six, seven, eight, and the like. In one embodiment of a physiological measurement system, a single multi-chip module is provided on a circuit board that performs operations to generate physiological information associated with a user of the system. In other embodiments, a plurality of multi-chip modules are provided on a circuit board of the physiological measurement system. The plurality of multi-chip modules may be stacked vertically on top of one another on the circuit board to further minimize the packaging size and the footprint of the circuit board.

In one multi-chip embodiment, two or more electrically-coupled circuit boards of a multi-chip module may be provided in a physiological measurement system in a vertically stacked manner to minimize the packaging size and the footprint of the circuit board. Vertically stacking the components on a circuit board minimizes the packaging size (e.g., the length and width) and the footprint occupied by the chips on the circuit board. In certain non-limiting embodiments, a circuit board including one or more physiological sensors may be placed closest to, proximal to or in contact with the user's skin, while one or more circuit boards including one or more processors, storage devices, communication components and non-physiological sensors may be provided in vertical layers that are distal to the user's skin.

Figure 8A:
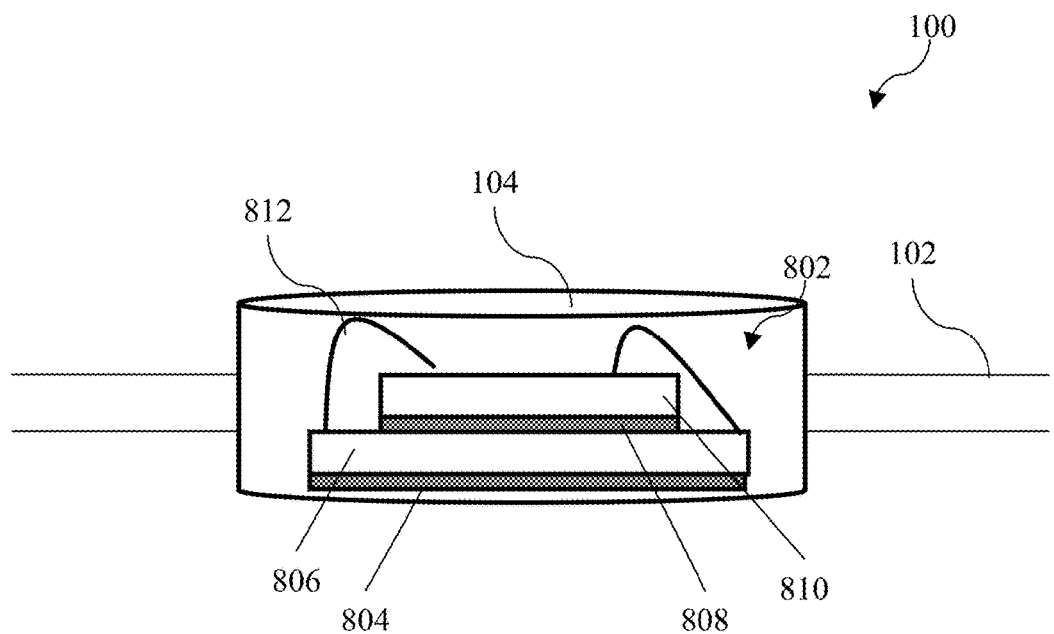
FIG. 8A depicts a sectional side view of an exemplary wearable physiological measurement system including a vertically-configured multi-chip module.
Figure 8B:
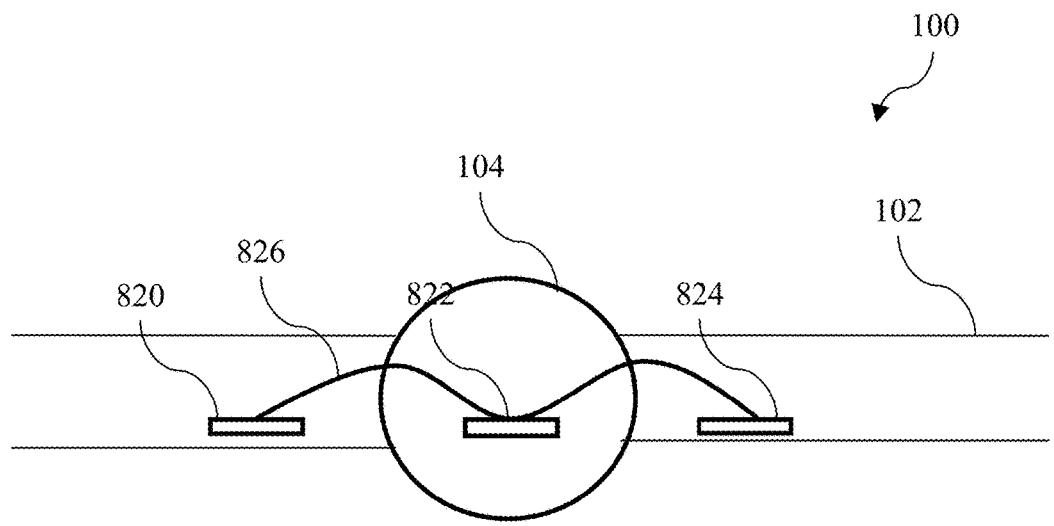
FIG. 8B depicts a sectional top view of an exemplary wearable physiological measurement system including a horizontally-configured multi-chip module.

FIGS. 8A and 8B depict a schematic side view and top view, respectively, of an exemplary physiological measurement system 100 including a head portion 104, a strap 102 and a multi-chip module. The head portion and/or the strap may include a circuit board 802 including a multi-chip module assembled in a vertically stacked configuration. Two or more layers of active electronic integrated circuit (IC) components are integrated vertically into a single circuit in the circuit board. The IC layers are oriented in spaced planes that extend substantially parallel to one another in a vertically stacked configuration. As illustrated in FIG. 8A, the circuit board 802 includes a substrate 804 for supporting the multi-chip module. A first integrated circuit chip 806 is coupled to the substrate 804 using any suitable coupling mechanism, for example, epoxy application and curing. A first spacer layer 808 is coupled to the surface of the first integrated circuit chip 806 opposite to the substrate 804 using, for example, epoxy application and curing. A second integrated circuit chip 810 is coupled to the surface of the first spacer layer 808 opposite to the first integrated circuit chip 806 using, for example, epoxy application and curing. The first and second integrated circuit chips 806 and 810 are electrically coupled using wiring 812.

In some embodiments, a metal frame may be provided for mechanical and/or electrical connection among the integrated circuit chips. An exemplary metal frame may take the form of a leadframe. The first and second integrated circuit chips may be coupled to the metal frame using wiring. A packaging may be provided to encapsulate the multi-chip module assembly and to maintain the multiple integrated circuit chips in substantially parallel arrangement with respect to one another.

As illustrated in FIG. 8A, the vertical three-dimensional stacking of the first integrated circuit chip 806 and the second integrated circuit chip 810 provides high-density functionality on the circuit board while minimizing overall packaging size and footprint (as compared to a circuit board that does not employ a vertically stacked multi-chip module). One of ordinary skill in the art will recognize that an exemplary multi-chip module is not limited to two stacked integrated circuit chips. Exemplary numbers of chips vertically integrated in a multi-chip module may include, but are not limited to, two, three, four, five, six, seven, eight, and the like.

In one embodiment, a single multi-chip module is provided. In other embodiments, a plurality of multi-chip modules as illustrated in FIG. 8A is provided. In an exemplary embodiment, a plurality of multi-chip modules (for example, two multi-chip modules) may be stacked vertically on top of one another on a circuit board of a physiological measurement system to further minimize the packaging size and footprint of the circuit board.

In addition to the need for reducing the footprint, there is also a need for decreasing the overall package height in multi-chip modules. Exemplary embodiments may employ wafer thinning to sub-hundreds micron to reduce the package height in multi-chip modules. Any suitable technique can be used to assemble a multi-chip module on a substrate. Exemplary assembly techniques include, but are not limited to, laminated MCM (MCM-L) in which the substrate is a multi-layer laminated printed circuit board, deposited MCM (MCM-D) in which the multi-chip modules are deposited on the base substrate using thin film technology, and ceramic substrate MCM (MCM-C) in which several conductive layers are deposited on a ceramic substrate and embedded in glass layers that layers are co-fired at high temperatures (HTCC) or low temperatures (LTCC).

In another multi-chip embodiment illustrated in FIG. 8B, two or more electrically-coupled circuit boards of a multi-chip module may be provided in a physiological measurement system in a horizontally spaced manner to minimize the height of the circuit board. Providing the components on a circuit board in a horizontally spaced manner minimizes the packaging height occupied by the chips on the circuit board. In certain non-limiting embodiments, a circuit board including one or more physiological sensors may be placed close to or in contact with the user's skin so that physiological signals are detected reliably, while one or more circuit boards including one or more processors, storage devices, communication components and non-physiological sensors may be provided may be distributed throughout the wearable system to provide improved flexibility, wearability, comfort and durability of the system.

FIG. 8B depicts a schematic top view of an exemplary physiological measurement system 100 including a head portion 104 and a strap 102. The head portion 104 and/or the strap 102 may include a circuit board including a plurality of integrated circuit boards or chips 820, 822, 824 forming a multi-chip module assembled in a horizontally spaced configuration. The integrated circuit chips are electrically coupled to one another using wiring 826. The circuit chips may be distributed through the head portion and/or the strap of the system. In the non-limiting illustrative embodiment, for example, one chip is provided in the head portion and two chips are provided in the strap.

Exemplary systems include a processing module configured to filter the raw photoplethysmography data received from the light detectors to minimize contributions due to motion, and subsequently process the filtered data to detect peaks in the data that correspond with heart beats of a user. The overall algorithm for detecting heart beats takes as input the analog signals from optical sensors (mV) and accelerometer, and outputs an implied beats per minute (heart rate) of the signal accurate within a few beats per minute as that determined by an electrocardiography machine even during motion.

Figure 9:
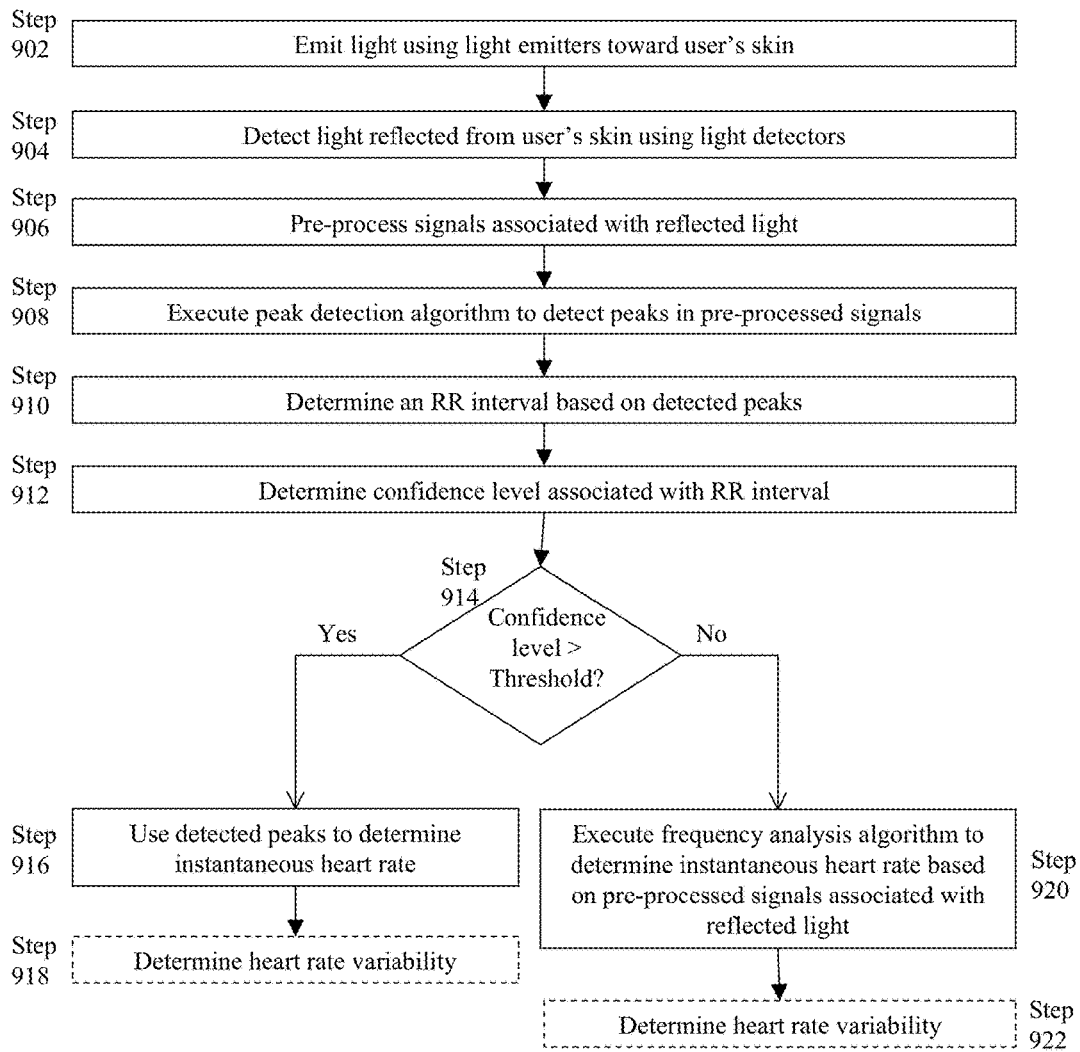
FIG. 9 is a flowchart illustrating an exemplary signal processing algorithm for generating a sequence of heart rates for every detected heart beat, the algorithm embodied in computer-executable instructions stored on one or more non-transitory computer-readable media.

FIG. 9 is a flowchart illustrating an exemplary signal processing algorithm for generating a sequence of heart rates for every detected heart beat, that is embodied in computer-executable instructions stored on one or more non-transitory computer-readable media. In step 902, light emitters of a wearable physiological measurement system emit light toward a user's skin. In step 904, light reflected from the user's skin is detected at the light detectors in the system. In step 906, signals or data associated with the reflected light are pre-processed using any suitable technique to facilitate detection of heart beats. In step 908, a processing module of the system executes one or more computer-executable instructions associated with a peak detection algorithm to process data corresponding to the reflected light to detect a plurality of peaks associated with a plurality of beats of the user's heart. In step 910, the processing module determines an R-wave-to-R-wave interval (RR interval) based on the plurality of peaks detected by the peak detection algorithm. In step 912, the processing module determines a confidence level associated with the RR interval estimate.

Based on the confidence level associated with the RR interval estimate, the processing module selects either the peak detection algorithm or a frequency analysis algorithm to process data corresponding to the reflected light to determine the sequence of instantaneous heart rates of the user. The frequency analysis algorithm may process the data corresponding to the reflected light based on the motion of the user detected using, for example, an accelerometer and/or a gyroscope. The processing module may select the peak detection algorithm or the frequency analysis algorithm regardless of a motion status of the user. It is advantageous to use the confidence in the estimate in deciding whether to switch to frequency-based methods as certain frequency-based approaches are unable to obtain accurate RR intervals for heart rate variability analysis. Therefore, the present invention maintains the ability to obtain the RR intervals for as long as possible, even in the case of motion, thereby maximizing the information that can be extracted.

For example, in step 914, it is determined whether the confidence level associated with the RR interval estimate is above (or equal to or above) a threshold. In certain embodiments, the threshold may be predefined, for example, about 50%-90% in some embodiments and about 80% in one non-limiting embodiment. In other embodiments, the threshold may be adaptive, i.e., the threshold may be dynamically and automatically determined based on previous confidence levels. For example, if one or more previous confidence levels were high (i.e., above a certain level), the system may determine that a present confidence level that is relatively low compared to the previous levels is indicative of a less reliable signal. In this case, the threshold may be dynamically adjusted to be higher so that a frequency-based analysis method may be selected to process the less reliable signal.

If the confidence level is above (or equal to or above) the threshold, in step 916, the processing module may use the plurality of peaks to determine an instantaneous heart rate of the user. On the other hand, in step 920, based on a determination that the confidence level associated with the RR interval is below (or equal to or below) the threshold, the processing module may execute one or more computer-executable instructions associated with the frequency analysis algorithm to determine an instantaneous heart rate of the user.

In some embodiments, in steps 918 or 922, the processing module determines a heart rate variability of the user based on the sequence of the instantaneous heart rates.

The wearable system may include or be coupled to (in a wired manner or wirelessly) a display device configured to render a user interface for displaying the sequence of the instantaneous heart rates of the user, the RR intervals and/or the heart rate variability determined by the processing module. The system may include or be coupled to a storage device configured to store the sequence of the instantaneous heart rates, the RR intervals and/or the heart rate variability determined by the processing module.

An exemplary peak detection algorithm uses a probabilistic peak detection algorithm. A discrete probabilistic step is set. The likelihood function is a mixture of a Gaussian random variable and a uniform. The heart of the likelihood function encodes the assumption that with probability (p) the peak detection algorithm has produced a reasonable initial estimate, but with probability (1-p) it has not. In a subsequent step, Bayes' rule is applied to determine the posterior density on the parameter space, of which the maximum is taken, i.e., the argument (parameter) that maximizes the posterior distribution. This value is the estimate for the heart rate. In a subsequent step, the previous two steps are reapplied for the rest of the sample. There is some variance in the signal due to process noise, which is dependent on the length of the interval. This process noise becomes the variance in the Gaussians used for the likelihood function. Then, the estimate is obtained as the maximum a posteriori on the new posterior distribution. A confidence value is recorded for the estimate for which, for some precision measurement, the posterior value is summed at points in the parameter space centered at the estimate plus or minus the precision.

The beats per minute (BPM) parameter space, $\theta$, may range between about 20 and about 240, corresponding to the empirical bounds on human heart rates. In an exemplary method, a probability distribution is calculated over this parameter space, at each step declaring the mode of the distribution to be the heart rate estimate. A discrete uniform prior may be set:

$$\pi_1 \sim \text{DiscUnif}(\theta)$$

The un-normalized, univariate likelihood is defined by a mixture of a Gaussian function and a uniform:

$$l_1 \sim IG + (1-I)U, G \sim N(\gamma_1 \sigma^2), I \sim Ber(p)$$

where $$U \sim \text{DiscUnif}(\theta)$$

and where $\sigma$ and p are predetermined constants.

Bayes' rule is applied to determine the posterior density on $\theta$, for example, by component-wise multiplying the prior density vector $(\pi_1(\theta))_{\theta \in \theta}$ with the likelihood vector $(l_1(\theta))_{\theta \in \theta}$ to obtain the posterior distribution $\eta_1$. Then, the following is set:

$$\beta_1 = \text{argmax}_{\theta \in \theta} \eta_1(\theta)$$

For k≥2, the variance in signal S(t) due to process noise is determined. Then, the following variable is set to imbue temporally long RR intervals with more process/interpeak noise and set the post-normalization convolution:

$$\pi_k = \eta_{k-1} * f_{N(o,\lambda_k^2)|\theta}$$

where $f$ is a density function of the following:

$$Z \sim N(o, \lambda_k^2)$$

Then, the following expressions are calculated:

$$l_k \sim pG_k + (1-p)U, G_k \sim N(\lambda k, \sigma^2)$$

The expression is then normalized and recorded:

$$\beta_k = \mathrm{argmax}_{\theta \in \Theta} \eta_k(\theta)$$

Finally, the confidence level of the above expression for a particular precision threshold is determined:

$$C_k = \sum_{\theta \in [\beta_k - e_1, \beta_k + e] \cap \theta} \eta_k.$$

An exemplary frequency analysis algorithm used in the present invention isolates the highest frequency components of the optical heart rate data, checks for harmonics common in both the accelerometer data and the optical data, and performs filtering of the optical data. The algorithm takes as input raw analog signals from the accelerometer (3-axis) and pulse sensors, and outputs heart rate values or beats per minute (BPM) for a given period of time related to the window of the spectrogram.

The isolation of the highest frequency components is performed in a plurality of stages, gradually winnowing the window-sizes of consideration, thereby narrowing the range of errors. In one implementation, a spectrogram of 2^15 samples with overlap 2^13 samples of the optical data is generated. The spectrogram is restricted to frequencies in which heart rate can lie. These restriction boundaries may be updated when smaller window sizes are considered. The frequency estimate is extracted from the spectrogram by identifying the most prominent frequency component of the spectrogram for the optical data. The frequency may be extracted using the following exemplary steps. The most prominent frequency of the spectrogram is identified in the signal. It is determined if the frequency estimate is a harmonic of the true frequency. The frequency estimate is replaced with the true frequency if the estimate is a harmonic of the true frequency. It is determined if the current frequency estimate is a harmonic of the motion sensor data. The frequency estimate is replaced with a previous temporal estimate if it is a harmonic of the motion sensor data. The upper and lower bounds on the frequency obtained are saved. A constant value may be added or subtracted in some cases. In subsequent steps, the constant added or subtracted may be reduced to provide narrower searches. A number of the previous steps are repeated one or more times, e.g., three times, except taking 2^{15-i} samples for the window size and 2^{13-i} for the overlap in the spectrogram where i is the current number of iteration. The final output is the average of the final symmetric endpoints of the frequency estimation.

The table below demonstrates the performance of the algorithm disclosed herein. To arrive at the results below, experiments were conducted in which a subject wore an exemplary wearable physiological measurement system and a 3-lead electrocardiography (ECG) system, which were both wired to the same microcontroller (e.g., Arduino) in order to provide time-synced data. Approximately 50 data sets were analyzed which included the subject standing still, walking, and running on a treadmill.

TABLE 1

Performance of signal processing algorithm disclosed herein

|  | Clean data error (mean, std. dev.) in BPM | Noisy data error (mean, std. dev.) in BPM |
| --- | --- | --- |
| 4-level spectrogram (80 second blocks) | 0.2, 2.3 | 0.8, 5.1 |

The algorithm's performance comes from a combination of a probabilistic and frequency based approach. The three difficulties in creating algorithms for heart rate calculations from the PPG data are 1) false detections of beats, 2) missed detections of real beats, and 3) errors in the precise timing of the beat detection. The algorithm disclosed herein provides improvements in these three sources of error and, in some cases, the error is bound to within 2 BPM of ECG values at all times even during the most motion-intense activities.

The exemplary wearable system computes heart rate variability (HRV) to obtain an understanding of the recovery status of the body. These values are captured right before a user awakes or when the user is not moving, in both cases photoplethysmography (PPG) variability yielding equivalence to the ECG HRV. HRV is traditionally measured using an ECG machine and by obtaining a time series of R-R intervals. Because an exemplary wearable system utilizes photoplethysmography (PPG), it does not obtain the electric signature from the heart beats; instead, the peaks in the obtained signal correspond to arterial blood volume. At rest, these peaks are directly correlated with cardiac cycles which enables the calculation of HRV via analyzing peak-to-peak intervals (the PPG analog of RR intervals). It has been demonstrated in the medical literature that these peak-to-peak intervals, the "PPG variability," is identical to ECG HRV while at rest. See, Charlot K, et. al. "Interchangeability between heart rate and photoplehysmography variabilities during sympathetic stimulations." *Physiological Measurement*. 2009 December; 30(12): 1357-69. doi: 10.1088/0967-3334/30/12/005. URL: http://www.ncbi.nlm.nih.gov/pubmed/19864707; and Lu, S, et. al. "Can photoplethysmography variability serve as an alternative approach to obtain heart rate variability information?" *Journal of Clinical Monitoring and Computing*. 2008 February; 22(1):23-9. URL: http://www.ncbi.nlm.nih.gov/pubmed/17987395, the entire contents of which are incorporated herein by reference.

Exemplary physiological measurement systems are configured to minimize power consumption so that the systems may be worn continuously without requiring power recharging at frequent intervals. The majority of current draw in an exemplary system is allocated to power the light emitters, e.g., LEDs, the wireless transceiver, the microcontroller and peripherals. In one embodiment, the circuit board of the system may include a boost converter that runs a current of about 10 mA through each of the light emitters with an efficiency of about 80% and may draw power directly from the batteries at substantially constant power. With exemplary batteries at about 3.7 V, the current draw from the battery may be about 40 mW. In some embodiments, the wireless transceiver may draw about 10-20 mA of current when it is actively transferring data. In some embodiments, the microcontroller and peripherals may draw about 5 mA of current.

An exemplary system may include a processing module that is configured to automatically adjust one or more operational characteristics of the light emitters and/or the light detectors to minimize power consumption while ensuring that all heart beats of the user are reliably and continuously detected. The operational characteristics may include, but are not limited to, a frequency of light emitted by the light emitters, the number of light emitters activated, a duty cycle of the light emitters, a brightness of the light emitters, a sampling rate of the light detectors, and the like.

The processing module may adjust the operational characteristics based on one or more signals or indicators obtained or derived from one or more sensors in the system including, but not limited to, a motion status of the user, a sleep status of the user, historical information on the user's physiological and/or habits, an environmental or contextual condition (e.g., ambient light conditions), a physical characteristic of the user (e.g., the optical characteristics of the user's skin), and the like.

In one embodiment, the processing module may receive data on the motion of the user using, for example, an accelerometer. The processing module may process the motion data to determine a motion status of the user which indicates the level of motion of the user, for example, exercise, light motion (e.g., walking), no motion or rest, sleep, and the like. The processing module may adjust the duty cycle of one or more light emitters and the corresponding sampling rate of the one or more light detectors based on the motion status. For example, upon determining that the motion status indicates that the user is at a first higher level of motion, the processing module may activate the light emitters at a first higher duty cycle and sample the reflected light using light detectors sampling at a first higher sampling rate. Upon determining that the motion status indicates that the user is at a second lower level of motion, the processing module may activate the light emitters at a second lower duty cycle and sample the reflected light using light detectors sampling at a second lower sampling rate. That is, the duty cycle of the light emitters and the corresponding sampling rate of the light detectors may be adjusted in a graduated or continuous manner based on the motion status or level of motion of the user. This adjustment ensures that heart rate data is detected at a sufficiently high frequency during motion to reliably detect all of the heart beats of the user.

In non-limiting examples, the light emitters may be activated at a duty cycle ranging from about 1% to about 100%. In another example, the light emitters may be activated at a duty cycle ranging from about 20% to about 50% to minimize power consumption. Certain exemplary sampling rates of the light detectors may range from about 50 Hz to about 1000 Hz, but are not limited to these exemplary rates. Certain non-limiting sampling rates are, for example, about 100 Hz, 200 Hz, 500 Hz, and the like.

In one non-limiting example, the light detectors may sample continuously when the user is performing an exercise routine so that the error standard deviation is kept within 5 beats per minute (BPM). When the user is at rest, the light detectors may be activated for about a 1% duty cycle—10 milliseconds each second (i.e., 1% of the time) so that the error standard deviation is kept within 5 BPM (including an error standard deviation in the heart rate measurement of 2 BPM and an error standard deviation in the heart rate changes between measurement of 3 BPM). When the user is in light motion (e.g., walking), the light detectors may be activated for about a 10% duty cycle—100 milliseconds each second (i.e., 10% of the time) so that the error standard deviation is kept within 6 BPM (including an error standard deviation in the heart rate measurement of 2 BPM and an error standard deviation in the heart rate changes between measurement of 4 BPM).

The processing module may adjust the brightness of one or more light emitters by adjusting the current supplied to the light emitters. For example, a first level of brightness may be set by current ranging between about 1 mA to about 10 mA, but is not limited to this exemplary range. A second higher level of brightness may be set by current ranging from about 11 mA to about 30 mA, but is not limited to this exemplary range. A third higher level of brightness may be set by current ranging from about 80 mA to about 120 mA, but is not limited to this exemplary range. In one non-limiting example, first, second and third levels of brightness may be set by current of about 5 mA, about 20 mA and about 100 mA, respectively.

In some embodiments, the processing module may detect an environmental or contextual condition (e.g., level of ambient light) and adjust the brightness of the light emitters accordingly to ensure that the light detectors reliably detect light reflected from the user's skin while minimizing power consumption. For example, if it is determined that the ambient light is at a first higher level, the brightness of the light emitters may be set at a first higher level. If it is determined that the ambient light is at a second lower level, the brightness of the light emitters may be set at a second lower level. The brightness may be adjusted in a graduated or continuous manner based on the detected environment conditions.

In some embodiments, the processing module may detect a physiological condition of the user (e.g., an optical characteristic of the user's skin) and adjust the brightness of the light emitters accordingly to ensure that the light detectors reliably detect light reflected from the user's skin while minimizing power consumption. For example, if it is determined that the user's skin is highly reflective, the brightness of the light emitters may be set at a first lower level. If it is determined that the user's skin is not very reflective, the brightness of the light emitters may be set at a second higher level.

Shorter-wavelength LEDs require more power than that required by longer-wavelength LEDs. Therefore, an exemplary wearable system may provide and use light emitted at two or more different frequencies based on the level of motion detected in order to save battery life. For example, upon determining that the motion status indicates that the user is at a first higher level of motion (e.g., exercising), one or more light emitters may be activated to emit light at a first wavelength. Upon determining that the motion status indicates that the user is at a second lower level of motion (e.g., at rest), one or more light emitters may be activated to emit light at a second wavelength that is longer than the first wavelength. Upon determining that the motion status indicates that the user is at a third lower level of motion (e.g., sleeping), one or more light emitters may be activated to emit light at a third wavelength that is longer than the first and second wavelengths. Other levels of motion may be predetermined and corresponding wavelengths of emitted light may be selected. The wavelength may be adjusted in a graduated or continuous manner. The threshold levels of motion that trigger adjustment of the light wavelength may be based on one or more factors including, but are not limited to, skin properties, ambient light conditions, and the like. Any suitable combination of light wavelengths may be selected, for example, green (for a higher level of motion)/red (for a lower level of motion); red (for a higher level of motion)/infrared (for a lower level of motion); blue (for a higher level of motion)/green (for a lower level of motion); and the like.

Shorter-wavelength LEDs require more power than is required by other types of heart rate sensors, such as, a piezo-sensor or an infrared sensor. Therefore, an exemplary wearable system may provide and use a unique combination of sensors—one or more light detectors for periods where motion is expected and one or more piezo and/or infrared sensors for low motion periods (e.g., sleep)—to save battery life. Certain other embodiments of a wearable system may exclude piezo-sensors and/or infrared sensors.

For example, upon determining that the motion status indicates that the user is at a first higher level of motion (e.g., exercising), one or more light emitters may be activated to emit light at a first wavelength. Upon determining that the motion status indicates that the user is at a second lower level of motion (e.g., at rest), non-light based sensors may be activated. The threshold levels of motion that trigger adjustment of the type of sensor may be based on one or more factors including, but are not limited to, skin properties, ambient light conditions, and the like.

The system may determine the type of sensor to use at a given time based on the level of motion (e.g., via an accelerometer) and whether the user is asleep (e.g., based on movement input, skin temperature and heart rate). Based on a combination of these factors the system selectively chooses which type of sensor to use in monitoring the heart rate of the user. Common symptoms of being asleep are periods of no movement or small bursts of movement (such as shifting in bed), lower skin temperature (although it is not a dramatic drop from normal), and heart rate that is below the typical resting heart rate when the user is awake. These variables depend on the physiology of a person and thus a machine learning algorithm is trained with user-specific input to determine when he/she is awake/asleep and determine from that the exact parameters that cause the algorithm to deem someone asleep.

In an exemplary configuration, the light detectors may be positioned on the underside of the wearable system and all of the heart rate sensors may be positioned adjacent to each other. For example, the low power sensor(s) may be adjacent to the high power sensor(s) as the sensors may be chosen and placed where the strongest signal occurs. In one example configuration, a 3-axis accelerometer may be used that is located on the top part of the wearable system.

In some embodiments, the processing module may be configured to automatically adjust a rate at which data is transmitted by the wireless transmitter to minimize power consumption while ensuring that raw and processed data generated by the system is reliably transmitted to external computing devices. In one embodiment, the processing module determines an amount of data to be transmitted (e.g., based on the amount of data generated since the time of the last data transmission), and may select the next data transmission time based on the amount of data to be transmitted. For example, if it is determined that the amount of data exceeds (or is equal to or greater than) a threshold level, the processing module may transmit the data or may schedule a time for transmitting the data. On the other hand, if it is determined that the amount of data does not exceed (or is equal to or lower than) the threshold level, the processing module may postpone data transmission to minimize power consumption by the transmitter. In one non-limiting example, the threshold may be set to the amount of data that may be sent in two seconds under current conditions. Exemplary data transmission rates may range from about 50 kbytes per second to about 1 Mbyte per second, but are not limiting to this exemplary range.

In some embodiments, an operational characteristic of the microprocessor may be automatically adjusted to minimize power consumption. This adjustment may be based on a level of motion of the user's body.

III. EXEMPLARY PHYSIOLOGICAL ANALYTICS SYSTEM

Exemplary embodiments provide an analytics system for enabling qualitative and quantitative monitoring and interpretation regarding a user's body, health and physical training. The analytics system is implemented in computer-executable instructions encoded on one or more non-transitory computer-readable media. The analytics system relies on and uses continuous or discontinuous data on one or more physiological parameters including, but not limited to, heart rate. The data used by the analytics system may be obtained or derived from an exemplary physiological measurement system disclosed herein, or may be obtained or derived from a derived source or system, for example, a database of physiological data. In some embodiments, the analytics system computes, stores and displays one or more indicators or scores relating to the user's body, health and physical training including, but not limited to, an intensity score and a recovery score. The scores may be updated in real-time and continuously or at specific time periods, for example, the recovery score may be determined every morning upon waking up, the intensity score may be determined in real-time or after a workout routine or for an entire day.

In certain exemplary embodiments, a fitness score may be automatically determined based on the physiological data of two or more users of exemplary wearable systems.

An intensity score or indicator provides an accurate indication of the cardiovascular intensities experienced by the user during a portion of a day, during the entire day or during any desired period of time (e.g., during a week or month). The intensity score is customized and adapted for the unique physiological properties of the user and takes into account, for example, the user's age, gender, anaerobic threshold, resting heart rate, maximum heart rate, and the like. If determined for an exercise routine, the intensity score provides an indication of the cardiovascular intensities experienced by the user continuously throughout the routine. If determined for a period of including and beyond an exercise routine, the intensity score provides an indication of the cardiovascular intensities experienced by the user during the routine and also the activities the user performed after the routine (e.g., resting on the couch, active day of shopping) that may affect their recovery or exercise readiness.

Figure 10:
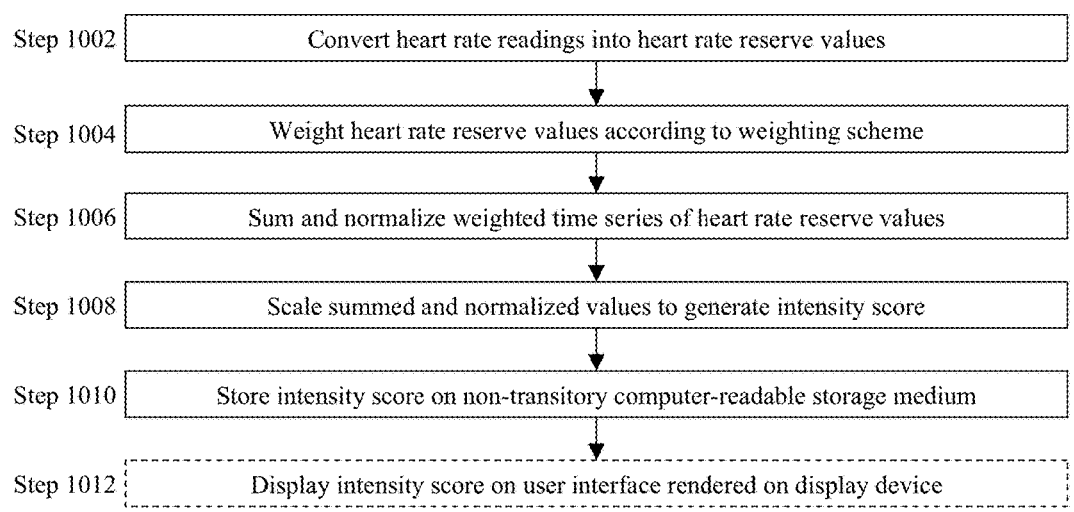
FIG. 10 is a flowchart illustrating an exemplary method of determining an intensity score, the method embodied in computer-executable instructions stored on one or more non-transitory computer-readable media.

In exemplary embodiments, the intensity score is calculated based on the user's heart rate reserve (HRR) as detected continuously throughout the desired time period, for example, throughout the entire day. In one embodiment, the intensity score is an integral sum of the weighted HRR detected continuously throughout the desired time period. FIG. 10 is a flowchart illustrating an exemplary method of determining an intensity score.

In step 1002, continuous heart rate readings are transformed or converted to HRR values. A time series of heart rate data used in step 1002 may be denoted as:

$H \in T$

A time series of HRR measurements, v(t), may be defined in the following expression in which MHR is the maximum heart rate and RHR is the resting heart rate of the user:

$$v(t) = \frac{H(t) - RHR}{MHR - RHR}$$

In step 1004, the HRR values are weighted according to a suitable weighting scheme. Cardiovascular intensity, indicated by an intensity score, is defined in the following expression in which w is a weighting function of the HRR measurements:

$$I(t_0, t_1) = \int_{t_0}^{t_1} w(v(t)) dt$$

In step 1006, the weighted time series of HRR values is summed and normalized.

$$I_T = \int_T w(v(t)) dt \leq w(1) |T|$$

Thus, the weighted sum is normalized to the unit interval, i.e., [0, 1]:

$$N_T = \frac{I_T}{w(1) \cdot 24 \, \text{hr}}$$

In step 1008, the summed and normalized values are scaled to generate user-friendly intensity score values. That is, the unit interval is transformed to have any desired distribution in a scale (e.g., a scale including 21 points from 0 to 21), for example, arctangent, sigmoid, sinusoidal, and the like. In certain distributions, the intensity values increase at a linear rate along the scale, and in others, at the highest ranges the intensity values increase at more than a linear rate to indicate that it is more difficult to climb in the scale toward the extreme end of the scale. In some embodiments, the raw intensity scores are scaled by fitting a curve to a selected group of "canonical" exercise routines that are predefined to have particular intensity scores.

In one embodiment, monotonic transformations of the unit interval are achieved to transform the raw HRR values to user-friendly intensity scores. An exemplary scaling scheme, expressed as $f: [0, 1] \rightarrow [0, 1]$, is performed using the following function:

$$(x, N, p) = 0.5 \left( \frac{\arctan(N(x - p))}{\pi / 2} + 1 \right)$$

To generate an intensity score, the resulting value may be multiplied by a number based on the desired scale of the intensity score. For example, if the intensity score is graduated from zero to 21, then the value may be multiplied by 21.

In step 1010, the intensity score values are stored on a non-transitory storage medium for retrieval, display and usage. In step 1012, the intensity score values are, in some embodiments, displayed on a user interface rendered on a visual display device. The intensity score values may be displayed as numbers and/or with the aid of graphical tools, e.g., a graphical display of the scale of intensity scores with current score, and the like. In some embodiments, the intensity score may be indicated by audio. In step 1012, the intensity score values are, in some embodiments, displayed along with one or more quantitative or qualitative pieces of information on the user including, but not limited to, whether the user has exceeded his/her anaerobic threshold, the heart rate zones experienced by the user during an exercise routine, how difficult an exercise routine was in the context of the user's training, the user's perceived exertion during an exercise routine, whether the exercise regimen of the user should be automatically adjusted (e.g., made easier if the intensity scores are consistently high), whether the user is likely to experience soreness the next day and the level of expected soreness, characteristics of the exercise routine (e.g., how difficult it was for the user, whether the exercise was in bursts or activity, whether the exercise was tapering, etc.), and the like. In one embodiment, the analytics system may automatically generate, store and display an exercise regimen customized based on the intensity scores of the user.

Step 1004 may use any of a number of exemplary static or dynamic weighting schemes that enable the intensity score to be customized and adapted for the unique physiological properties of the user. In one exemplary static weighting scheme, the weights applied to the HRR values are based on static models of a physiological process. The human body employs different sources of energy with varying efficiencies and advantages at different HRR levels. For example, at the anaerobic threshold (AT), the body shifts to anaerobic respiration in which the cells produce two adenosine triphosphate (ATP) molecules per glucose molecule, as opposed to 36 at lower HRR levels. At even higher HRR levels, there is a further subsequent threshold (CPT) at which creatine triphosphate (CTP) is employed for respiration with even less efficiency.

In order to account for the differing levels of cardiovascular exertion and efficiency at the different HRR levels, in one embodiment, the possible values of HRR are divided into a plurality of categories, sections or levels (e.g., three) dependent on the efficiency of cellular respiration at the respective categories. The HRR parameter range may be divided in any suitable manner, such as, piecewise, including piecewise-linear, piecewise-exponential, and the like. An exemplary piecewise-linear division of the HRR parameter range enables weighting each category with strictly increasing values. This scheme captures an accurate indication of the cardiovascular intensity experienced by the user because it is more difficult to spend time at higher HRR values, which suggests that the weighting function should increase at the increasing weight categories.

In one non-limiting example, the HRR parameter range may be considered a range from zero (0) to one (1) and divided into categories with strictly increasing weights. In one example, the HRR parameter range may be divided into a first category of a zero HRR value and may assign this category a weight of zero; a second category of HRR values falling between zero (0) and the user's anaerobic threshold (AT) and may assign this category a weight of one (1); a third category of HRR values falling between the user's anaerobic threshold (AT) and a threshold (CPT) at which the user's body employs creatine triphosphate for respiration and may assign this category a weight of 18; and a fourth category of HRR values falling between the creatine triphosphate threshold (CPT) and one (1) and may assign this category a weight of 42, although other numbers of HRR categories and different weight values are possible. That is, in this example, the weights are defined as:

$$w(v) = \begin{cases} 0 & : v = 0 \\ 1 & : v \in (0, AT] \\ 18 & : v \in (AT, CPT] \\ 42 & : v \in (CPT, 1] \end{cases}$$

In another exemplary embodiment of the weighting scheme, the HRR time series is weighted iteratively based on the intensity scores determined thus far (e.g., the intensity score accrued thus far) and the path taken by the HRR values to get to the present intensity score. The path may be detected automatically based on the historical HRR values and may indicate, for example, whether the user is performing high intensity interval training (during which the intensity scores are rapidly rising and falling), whether the user is taking long breaks between bursts of exercise (during which the intensity scores are rising after longer periods), and the like. The path may be used to dynamically determine and adjust the weights applied to the HRR values. For example, in the case of high intensity interval training, the weights applied may be higher than in the case of a more traditional exercise routine.

In another exemplary embodiment of the weighting scheme, a predictive approach is used by modeling the weights or coefficients to be the coefficient estimates of a logistic regression model. In this scheme, a training data set is obtained by continuously detecting the heart rate time series and other personal parameters of a group of individuals. The training data set is used to train a machine learning system to predict the cardiovascular intensities experienced by the individuals based on the heart rate and other personal data. The trained system models a regression in which the coefficient estimates correspond to the weights or coefficients of the weighting scheme. In the training phase, user input on perceived exertion and the intensity scores are compared. The learning algorithm also alters the weighs based on the improving or declining health of a user as well as their qualitative feedback. This yields a unique algorithm that incorporates physiology, qualitative feedback, and quantitative data. In determining a weighting scheme for a specific user, the trained machine learning system is run by executing computer-executable instructions encoded on one or more non-transitory computer-readable media, and generates the coefficient estimates which are then used to weight the user's HRR time series.

One of ordinary skill in the art will recognize that two or more aspects of any of the disclosed weighting schemes may be applied separately or in combination in an exemplary method for determining an intensity score.

A recovery score or indicator provides an accurate indication of the level of recovery of a user's body and health after a period of physical exertion. The human autonomic nervous system controls the involuntary aspects of the body's physiology and is typically subdivided into two branches: parasympathetic (deactivating) and sympathetic (activating). Heart rate variability (HRV), i.e., the fluctuation in inter-heartbeat interval time, is a commonly studied result of the interplay between these two competing branches. Parasympathetic activation reflects inputs from internal organs, causing a decrease in heart rate. Sympathetic activation increases in response to stress, exercise and disease, causing an increase in heart rate. For example, when high intensity exercise takes place, the sympathetic response to the exercise persists long after the completion of the exercise. When high intensity exercise is followed by insufficient recovery, this imbalance lasts typically until the next morning, resulting in a low morning HRV. This result should be taken as a warning sign as it indicates that the parasympathetic system was suppressed throughout the night. While suppressed, normal repair and maintenance processes that ordinarily would occur during sleep were suppressed as well. Suppression of the normal repair and maintenance processes results in an unprepared state for the next day, making subsequent exercise attempts more challenging.

The recovery score is customized and adapted for the unique physiological properties of the user and takes into account, for example, the user's heart rate variability (HRV), resting heart rate, sleep quality and recent physiological strain (indicated, in one example, by the intensity score of the user). In one exemplary embodiment, the recovery score is a weighted combination of the user's heart rate variability (HRV), resting heart rate, sleep quality indicated by a sleep score, and recent strain (indicated, in one example, by the intensity score of the user). In an exemplar, the sleep score combined with performance readiness measures (such as, morning heart rate and morning heart rate variability) provides a complete overview of recovery to the user. By considering sleep and HRV alone or in combination, the user can understand how exercise-ready he/she is each day and to understand how he/she arrived at the exercise-readiness score each day, for example, whether a low exercise-readiness score is a predictor of poor recovery habits or an inappropriate training schedule. This insight aids the user in adjusting his/her daily activities, exercise regimen and sleeping schedule therefore obtain the most out of his/her training.

In some cases, the recovery score may take into account perceived psychological strain experienced by the user. In some cases, perceived psychological strain may be detected from user input via, for example, a questionnaire on a mobile device or web application. In other cases, psychological strain may be determined automatically by detecting changes in sympathetic activation based on one or more parameters including, but not limited to, heart rate variability, heart rate, galvanic skin response, and the like.

With regard to the user's HRV used in determining the recovery score, suitable techniques for analyzing HRV include, but are not limited to, time-domain methods, frequency-domain methods, geometric methods and non-linear methods. In one embodiment, the HRV metric of the root-mean-square of successive differences of RR intervals (RMSSD) is used. The analytics system may consider the magnitude of the differences between 7-day moving averages and 3-day moving averages of these readings for a given day. Other embodiments may use Poincaré Plot analysis or other suitable metrics of HRV.

With regard to the user's resting heart rate, moving averages of the resting heart rate are analyzed to determine significant deviations. Consideration of the moving averages is important since day-to-day physiological variation is quite large even in healthy individuals. Therefore, the analytics system may perform a smoothing operation to distinguish changes from normal fluctuations.

Although an inactive condition, sleep is a highly active recovery state during which a major portion of the physiological recovery process takes place. Nonetheless, a small, yet significant, amount of recovery can occur throughout the day by rehydration, macronutrient replacement, lactic acid removal, glycogen re-synthesis, growth hormone production and a limited amount of musculoskeletal repair. In assessing the user's sleep quality, the analytics system generates a sleep score using continuous data collected by an exemplary physiological measurement system regarding the user's heart rate, skin conductivity, ambient temperature and accelerometer/gyroscope data throughout the user's sleep. Collection and use of these four streams of data enable an understanding of sleep previously only accessible through invasive and disruptive over-night laboratory testing. For example, an increase in skin conductivity when ambient temperature is not increasing, the wearer's heart rate is low, and the accelerometer/gyroscope shows little motion, may indicate that the wearer has fallen asleep. The sleep score indicates and is a measure of sleep efficiency (how good the user's sleep was) and sleep duration (if the user had sufficient sleep). Each of these measures is determined by a combination of physiological parameters, personal habits and daily stress/strain (intensity) inputs. The actual data measuring the time spent in various stages of sleep may be combined with the wearer's recent daily history and a longer-term data set describing the wearer's personal habits to assess the level of sleep sufficiency achieved by the user. The sleep score is designed to model sleep quality in the context of sleep duration and history. It thus takes advantage of the continuous monitoring nature of the exemplary physiological measurement systems disclosed herein by considering each sleep period in the context of biologically-determined sleep needs, pattern-determined sleep needs and historically-determined sleep debt.

The recovery and sleep score values are stored on a non-transitory storage medium for retrieval, display and usage. The recovery and/or sleep score values are, in some embodiments, displayed on a user interface rendered on a visual display device. The recovery and/or sleep score values may be displayed as numbers and/or with the aid of graphical tools, e.g., a graphical display of the scale of recovery scores with current score, and the like. In some embodiments, the recovery and/or sleep score may be indicated by audio. The recovery score values are, in some embodiments, displayed along with one or more quantitative or qualitative pieces of information on the user including, but not limited to, whether the user has recovered sufficiently, what level of activity the user is prepared to perform, whether the user is prepared to perform an exercise routine a particular desired intensity, whether the user should rest and the duration of recommended rest, whether the exercise regimen of the user should be automatically adjusted (e.g., made easier if the recovery score is low), and the like. In one embodiment, the analytics system may automatically generate, store and display an exercise regimen customized based on the recovery scores of the user alone or in combination with the intensity scores.

Figure 11:
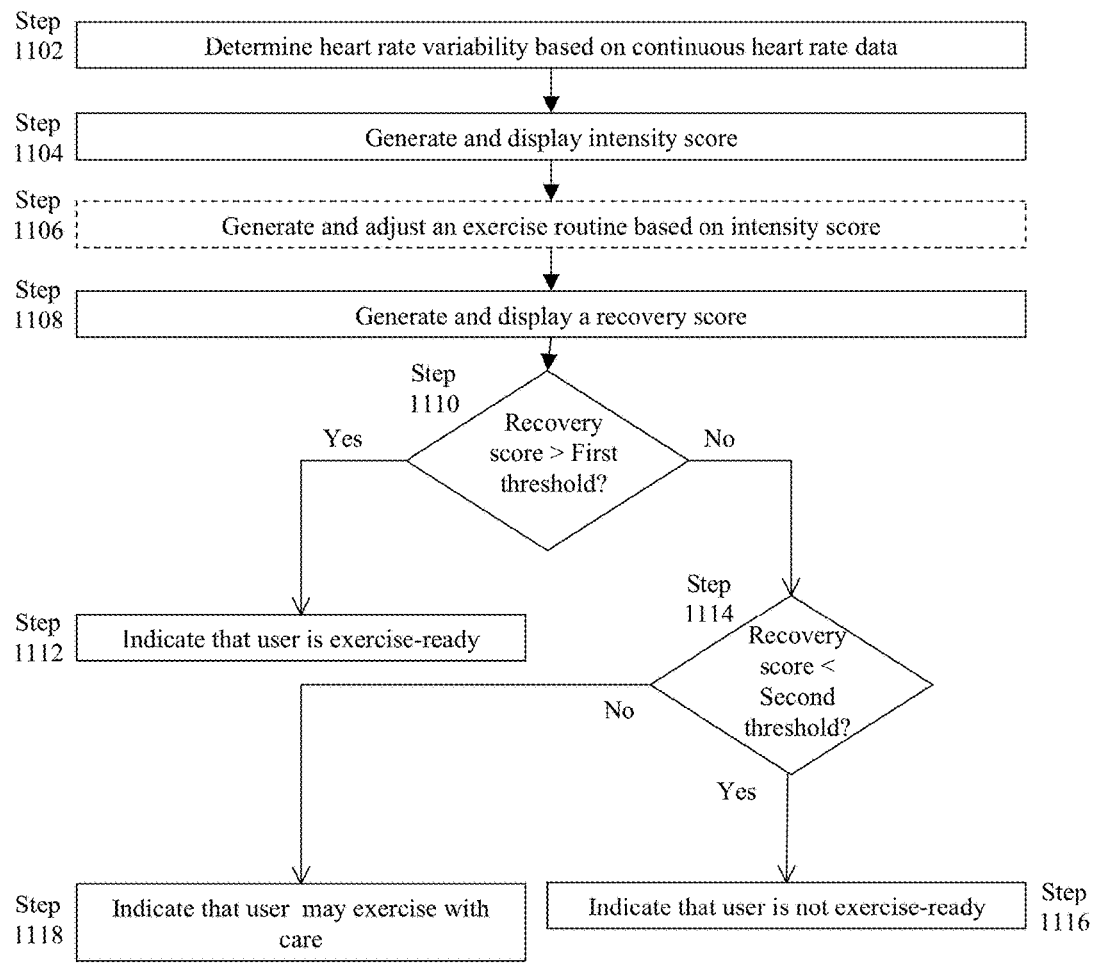
FIG. 11 is a flowchart illustrating an exemplary method by which a user may use intensity and recovery scores, the method embodied in computer-executable instructions stored on one or more non-transitory computer-readable media.
Figure 12:
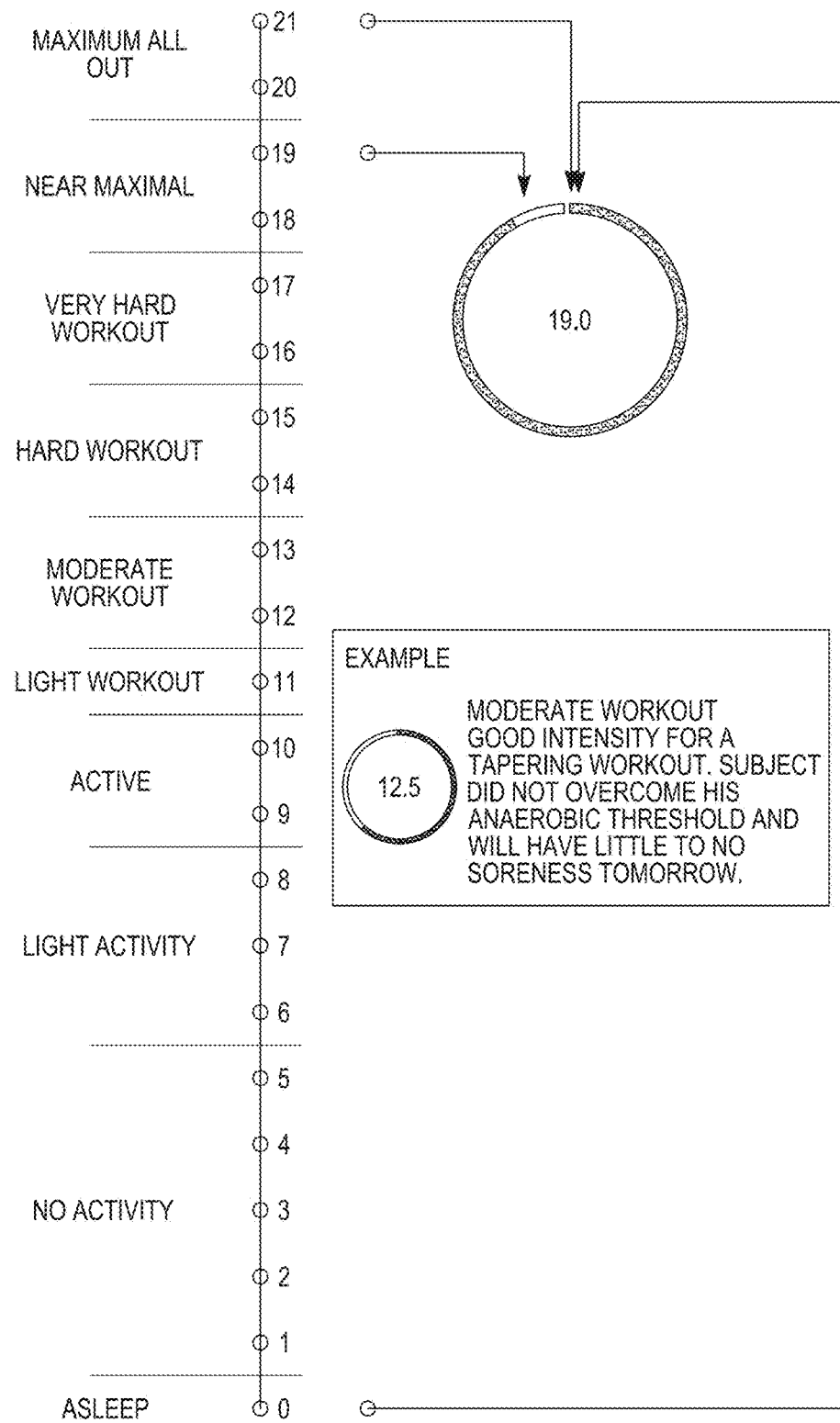
FIG. 12 illustrates an exemplary display of an intensity score index indicated in a circular graphic component with an exemplary current score of 19.0 indicated.
Figure 15B:
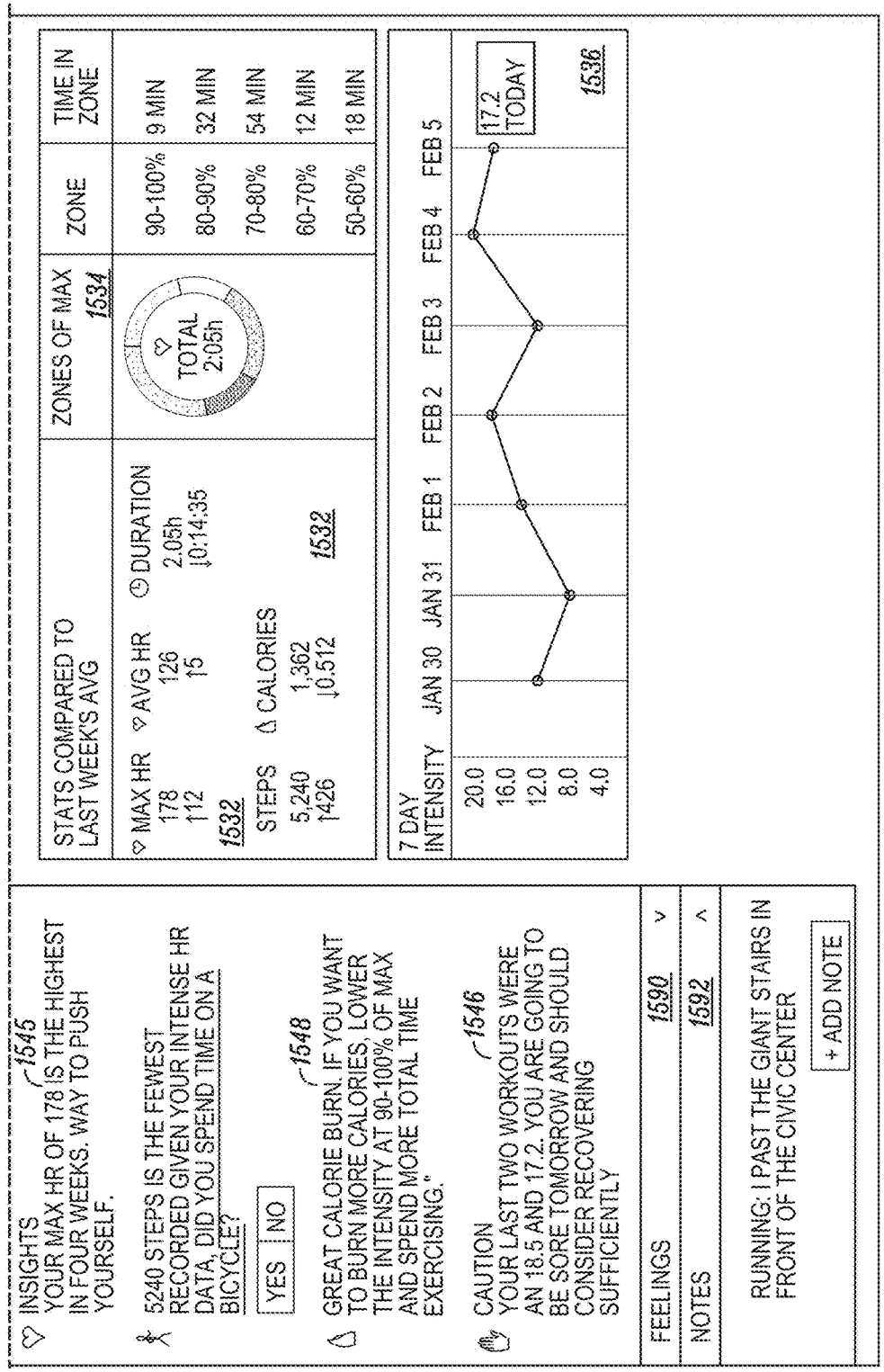
Figure 16A:
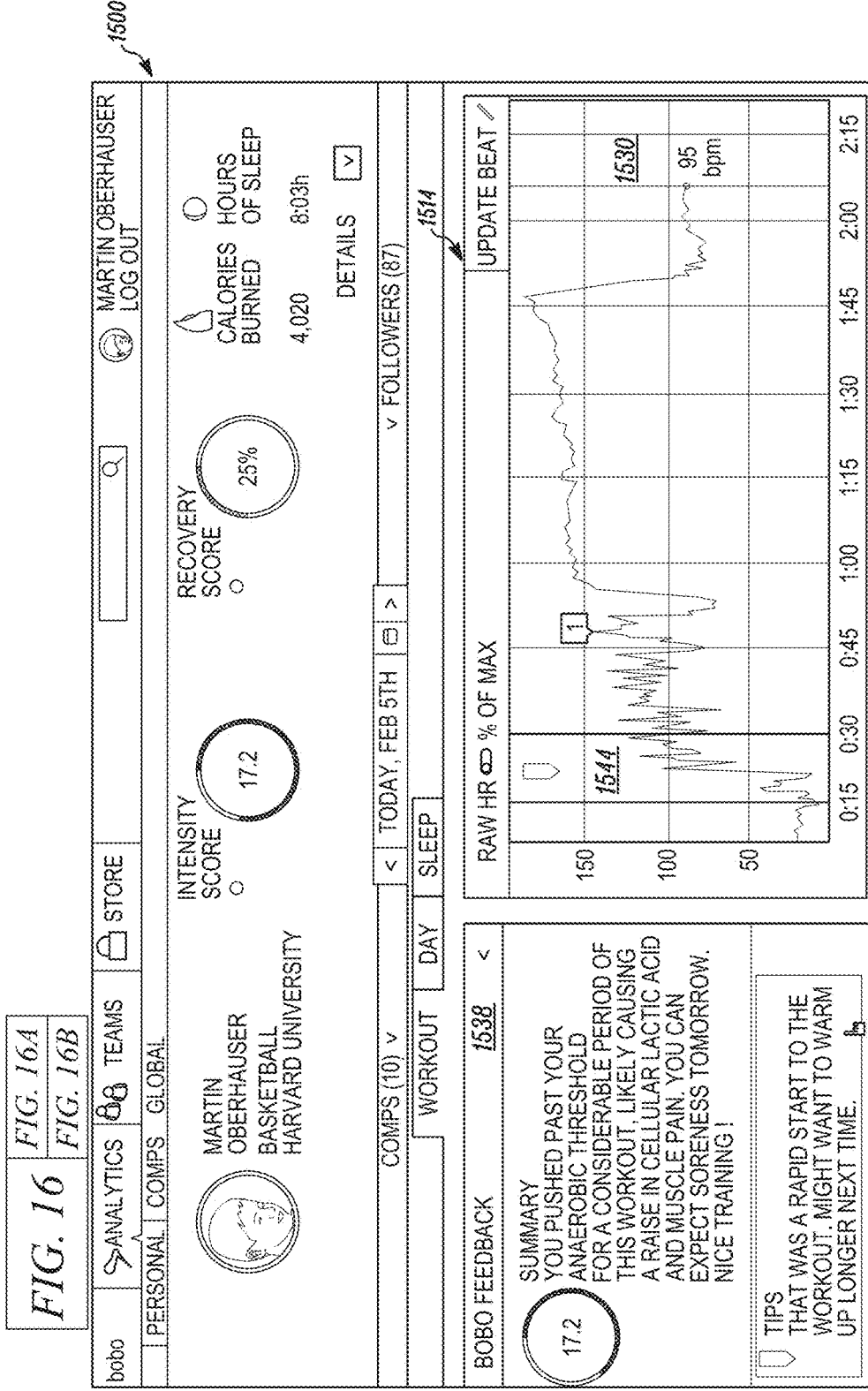
Figure 16B:
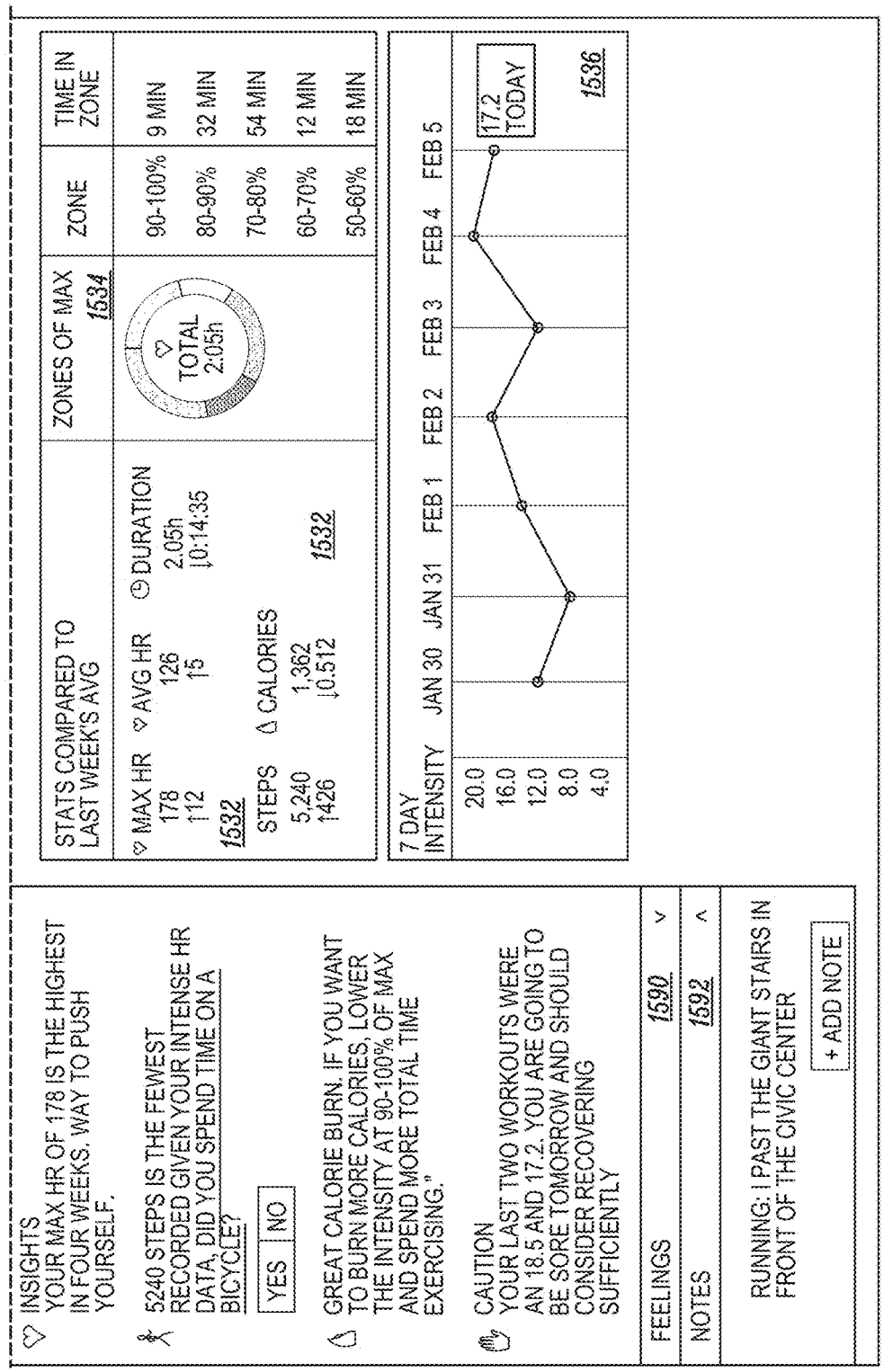
Figure 17A:
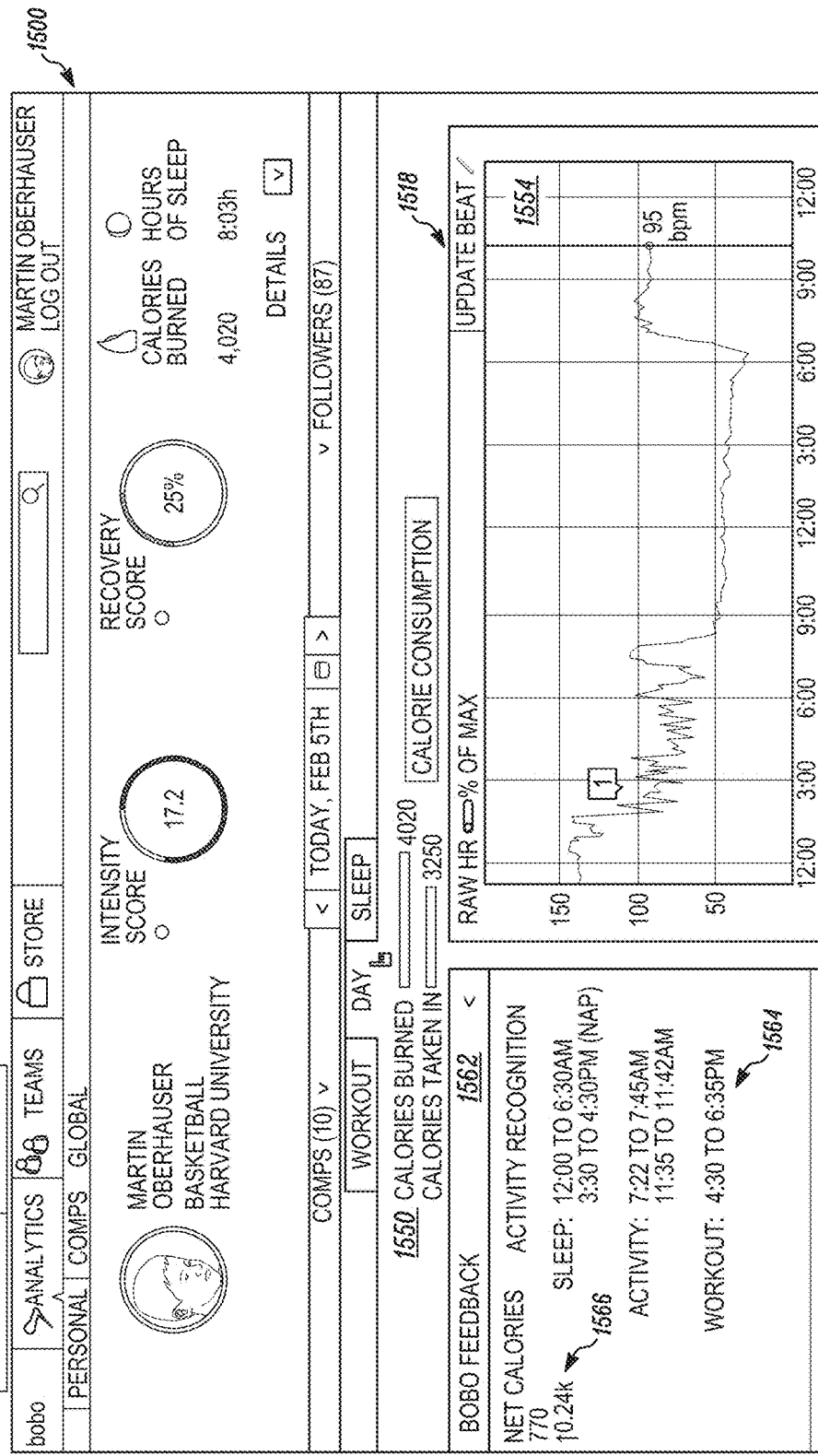

FIG. 11 is a flowchart illustrating an exemplary method by which a user may use intensity and recovery scores. In step 1102, the wearable physiological measurement system begins determining heart rate variability (HRV) measurements based on continuous heart rate data collected by an exemplary physiological measurement system. In some cases, it may take the collection of several days of heart rate data to obtain an accurate baseline for the HRV. In step 1104, the analytics system may generate and display intensity score for an entire day or an exercise routine. In some cases, the analytics system may display quantitative and/or qualitative information corresponding to the intensity score. FIG. 12 illustrates an exemplary display of an intensity score index indicated in a circular graphic component with an exemplary current score of 19.0 indicated. The graphic component may indicate a degree of difficulty of the exercise corresponding to the current score selected from, for example, maximum all out, near maximal, very hard, hard, moderate, light, active, light active, no activity, asleep, and the like. The display may indicate, for example, that the intensity score corresponds to a good and tapering exercise routine, that the user did not overcome his anaerobic threshold and that the user will have little to no soreness the next day.

In step 1106, in an exemplary embodiment, the analytics system may automatically generate or adjust an exercise routine or regimen based on the user's actual intensity scores or desired intensity scores. For example, based on inputs of the user's actual intensity scores, a desired intensity score (that is higher than the actual intensity scores) and a first exercise routine currently performed by the user (e.g., walking), the analytics system may recommend a second different exercise routine that is typically associated with higher intensity scores than the first exercise routine (e.g., running). The exercise routine may be displayed on a display device.

In step 1108, at any given time during the day (e.g., every morning), the analytics system may generate and display a recovery score. In some cases, the analytics system may display quantitative and/or qualitative information corresponding to the intensity score. For example, in step 1110, in an exemplary embodiment, the analytics system may determine if the recovery is greater than (or equal to or greater than) a first predetermined threshold (e.g., about 60% to about 80% in some examples) that indicates that the user is recovered and is ready for exercise. If this is the case, in step 1112, the analytics system may indicate that the user is ready to perform an exercise routine at a desired intensity or that the user is ready to perform an exercise routine more challenging than the past day's routine. Otherwise, in step 1114, the analytics system may determine if the recovery is lower than (or equal to or lower than) a second predetermined threshold (e.g., about 10% to about 40% in some examples) that indicates that the user has not recovered. If this is the case, in step 1116, the analytics system may indicate that the user should not exercise and should rest for an extended period. The analytics system may, in some cases, the duration of recommended rest. Otherwise, in step 1118, the analytics system may indicate that the user may exercise according to his/her exercise regimen while being careful not to overexert him/herself. The thresholds may, in some cases, be adjusted based on a desired intensity at which the user desires to exercise. For example, the thresholds may be increased for higher planned intensity scores.

FIG. 13 illustrates an exemplary display of a recovery score index indicated in a circular graphic component with a first threshold of 66% and a second threshold of 33% indicated. FIGS. 14A-14C illustrate the recovery score graphic component with exemplary recovery scores and qualitative information corresponding to the recovery scores.

Optionally, in an exemplary embodiment, the analytics system may automatically generate or adjust an exercise routine or regimen based on the user's actual recovery scores (e.g., to recommend lighter exercise for days during which the user has not recovered sufficiently). This process may also use a combination of the intensity and recovery scores.

The analytics system may, in some embodiments, determine and display the intensity and/or recovery scores of a plurality of users in a comparative manner. This enables users to match exercise routines with others based on comparisons among their intensity scores.

IV. EXEMPLARY DISPLAYS AND USER INTERFACES

An aspect of the present invention is directed to providing an online website for health and fitness monitoring. Exemplary embodiments also provide a vibrant and interactive online community for displaying and sharing physiological data among users. The website allows users to monitor their own fitness results, share information with their teammates and coaches, compete with other users, and win status. The website may be configured to provide an interactive user interface. The website may be configured to display results based on analysis on physiological data associated with one or more users. The website may be configured to provide competitive ways to compare one user to another, and ultimately a more interactive experience for the user. For example, in some embodiments, instead of merely comparing a user's physiological data and performance relative to that user's past performances, the user may be allowed to compete with other users and the user's performance may be compared to that of other users.

A user of the website may include an individual whose health or fitness is being monitored, such as an individual wearing a bracelet disclosed herein, an athlete, a sports team member, a personal trainer or a coach. In some embodiments, a user may pick their own trainer from a list to comment on their performance.

In certain embodiments, the physiological data may be obtained, directly or indirectly, from a wearable physiological measurement system as disclosed herein. In other embodiments, the physiological data may be obtained from any other suitable system (e.g., an ECG system) or storage device (e.g., a physiological database). Exemplary wearable physiological measurement systems have the ability to stream physiological information wirelessly, directly or through a mobile device application and/or through a cloud-based storage system, to an online website. Both the wearable system and the website allow a user to provide feedback regarding his day, which enables recovery and performance ratings.

In some embodiments, the website may be a mobile website or a mobile application. In some embodiments, the website may be configured to communicate data to other websites, devices or applications.

The exemplary website may require a brief and free sign-up process during which a user may create an account with his/her name, account name, email, home address, height, weight, age, and a unique code provided in his/her wearable physiological measurement system. The unique code may be provided, for example, on the wearable system itself or in the packaged kit. Once subscribed, continuous physiological data received from the user's system may be retrieved in a real-time continuous basis and presented automatically on a webpage associated with the user. Alternatively, updated data may be displayed upon a user prompt or periodically. Additionally, the user can add information to his profile, such as, a picture, favorite activities, sports team(s), and the user may search for teammates/friends on the website for sharing information.

FIGS. 15A-18B illustrate an exemplary user interface 1500 for displaying physiological data specific to a user as rendered on visual display device. The user interface 1500 may take the form of a webpage in some embodiments. One of ordinary skill in the art will recognize that the information in FIGS. 15-18 represent non-limiting illustrative examples. One of ordinary skill in the art will recognize that the particular types of information disclosed with respect to FIGS. 15A-18B are exemplary and non-limiting. The user interface 1500 may include a summary panel 1502 including an identification 1504 of the user (e.g., a real or account name) with, optionally, a picture or photo corresponding to the user. The summary panel 1502 may also display the current intensity score 1506 and the current recovery score 1508 of the user. In some embodiments, the summary panel 1502 may display the number of calories burned by the user 1510 that day and the number of hours of sleep 1512 obtained by the user the previous night.

The user interface 1500 may also include panels for presenting information on the user's workouts—a workout panel 1514 accessible using tab 1516, day—a day panel 1518 accessible using tab 1520, and sleep—a sleep panel 1522 accessible using tab 1524. The same or different feedback panels may be associated with the workout, day and sleep panels. The panels may enable the user to select and customize one or more informative panels that appear in his/her user interface display.

The workout panel 1514 may present quantitative information on the user's health and exercise routines, for example, a graph 1530 of the user's continuous heart rate during the exercise, statistics 1532 on the maximum heart rate, average heart rate, duration of exercise, number of steps taken and calories expended, zones 1534 in which the maximum heart rate fell during the exercise, and a graph 1536 of the intensity scores over a period of time (e.g., seven days).

A feedback panel 1538 associated with the workout panel 1514 may present information on the intensity score and the exercise routines performed by the user during a selected period of time including, but not limited to, quantitative information, qualitative information, feedback, recommendations on future exercise routines, and the like. The feedback panel 1538 may present the intensity score along with a qualitative summary 1540 of the score indicating, for example, whether the user pushed past his anaerobic threshold for a considerable period of the exercise, whether the exercise is likely to cause muscle pain and soreness, and the like. Based on analysis of the quantitative health parameters monitored during the exercise routine, the feedback panel 1538 may present one or more tips 1542 on adjusting the exercise routine, for example, that the exercise routine started too rapidly and that the user should warm up for longer. In some cases, upon selection of the tips sub-panel 1542, a corresponding indicator 1544 may be provided in the heart rate graph 1530.

Based on analysis of the quantitative health parameters monitored during the exercise routine, the feedback panel 1538 may also present qualitative information 1545 on the user's exercise routine, for example, comparison of the present day's exercise routine to the user's historical exercise data. Such information may indicate, for example, that the user's maximum heart rate for the day's exercise was the highest ever recorded, that the steps taken by the user that day was the fewest ever recorded, that the user burned a lot of calories and that more calories may be burned by lowering the intensity of the exercise, and the like. The feedback panel 1538 may also present cautionary indicators 1546 to warn the user of future anticipated health events, for example, the likelihood of soreness (e.g., if the intensity score is higher than a predefined threshold), and the like.

An exemplary analytics system may analyze the information presented in the workout panel 1514 and automatically determine whether the user performed a specific exercise routine or activity. As one example, given a small number of steps taken and a high calorie burn and heart rate, the system may determine that it is possible the user rode a bicycle that day. In some cases, the feedback panel 1538 may prompt the user to confirm whether he/she indeed performed that activity in a user input field 1548. This user input may be displayed and/or used to improve an understanding of the user's health and exercise routines.

The day panel 1518 may include information on health parameters of the user during the current day including, but not limited to, the number of calories burned and the number of calories taken in 1550 (which may be based on user input on the foods eaten), a graph 1554 of the day's continuous heart rate, statistics 1556 on the resting heart rate and steps taken by the user that day, a graph 1558 of the calories burned that and other days, and the like.

In some cases, an analytics system may analyze the physiological data (e.g., heart rate data) and estimate the durations of sleep, activity and workout during the day. A feedback panel 1562 associated with the day panel 1518 may present these durations 1564. In some cases, the feedback panel 1562 may display a net number of calories consumed by the user that day 1566. Based on analysis of the quantitative health parameters monitored during the exercise routine, the feedback panel 1562 may also present qualitative information 1568 on the user's exercise routine. Such information may indicate, for example, that the user was stressed at a certain point in the day (e.g., if there was a high level of sweat with little activity), that the user's maximum heart rate for the day's exercise was the highest ever recorded, that the steps taken by the user that day was the fewest ever recorded, that the user burned a lot of calories and that more calories may be burned by lowering the intensity of the exercise, and the like. The feedback panel 1562 may also present cautionary indicators 1570 to warn the user of future anticipated health events, for example, tachycardia, susceptibility to illness or overtraining (e.g., if the resting heart rate is elevated for a few days), and the like.

An exemplary analytics system may analyze the information presented in the day panel 1518 and automatically determine whether the user performed a specific exercise routine or activity. As one example, given an elevated heart rate with little activity, the system may determine that it is possible the user drank coffee at that point. In some cases, the feedback panel 1562 may prompt the user to confirm whether he/she indeed performed that activity in a user input field 1572. This user input may be displayed and/or used to improve an understanding of the user's health and exercise routines.

The sleep panel 1522 may include information on health parameters of the user during sleep including, but not limited to, an overlaid graph 1573 of heart rate and movement during sleep, statistics 1574 on the maximum heart rate, minimum heart rate, number of times the user awoke during sleep, average movement during sleep, a sleep cycle indicator 1576 showing durations spent awake, in light sleep, in deep sleep and in REM sleep, and a sleep duration graph 1578 showing the number of hours slept over a period of time.

A feedback panel 1580 associated with the sleep panel 1522 may present information on the user's sleep including, but not limited to, quantitative information, qualitative information, feedback, recommendations on future exercise routines, and the like. The feedback panel 1580 may present a sleep score and/or a number of hours of sleep along with a qualitative summary of the score 1582 indicating, for example, whether the user slept enough, whether the sleep was efficient or inefficient, whether the user moved around and how much during sleep, and the like. Based on analysis of the quantitative health parameters monitored during sleep, the feedback panel 1580 may present one or more tips 1584 on adjusting sleep, for example, that the woke up a number of times during sleep and that user can try to sleep on his side rather than on his back.

Based on analysis of the quantitative health parameters monitored during the exercise routine, the feedback panel 1580 may also present qualitative information 1586 on the user's sleep. Such information may indicate, for example, that the user's maximum heart rate for the day's exercise was the highest ever recorded during sleep. The feedback panel 1580 may also present cautionary indicators 1588 to warn the user of future anticipated health events, for example, a sign of overtraining and a recommendation to get more sleep (e.g., if the user awoke many times during sleep and/or if the user moved around during sleep).

The user interface 1500 may provide a user input field 1590 for enabling the user to indicate his/her feelings on, for example, the activities performed, perceived exertion, energy level, performance. The user interface 1500 may also provide a user input field 1592 for enabling the user to indicate other facts about his exercise routine, e.g., comments on what the user was doing at a specific point in the exercise routine with a link 1594 to a corresponding point in the heart rate graph 1530. In some embodiments, the user may specify a route and/or location on a map at which the exercise routine was performed.

Exemplary embodiments also enable a user to compare his/her quantitative and/or qualitative physiological data with those of one or more additional users. A user may be presented with user selection components representing other users whose data is available for display, as shown in exemplary user interface 2100 in FIG. 21. When a pointer is hovered over a user selection component (e.g., an icon representing a user), a snapshot of the user's information is presented in a popup component, and clicking on the user selection component opens up the full user interface displaying the user's information. In some cases, the user selection components include certain user-specific data surrounding an image representing the user, for example, a graphic element indicating the user's intensity score. The user selection components may be provided in a grid as shown or in a linear listing for easier sorting. The users appearing in the user selection components may be sorted and/or ranked based on any desired criteria, e.g., intensity scores, who is experiencing soreness, and the like. A user may leave comments on other users' pages. Similarly, a user may select privacy settings to indicate which aspects of his/her own data may be viewed by other users.

Figure 19B:
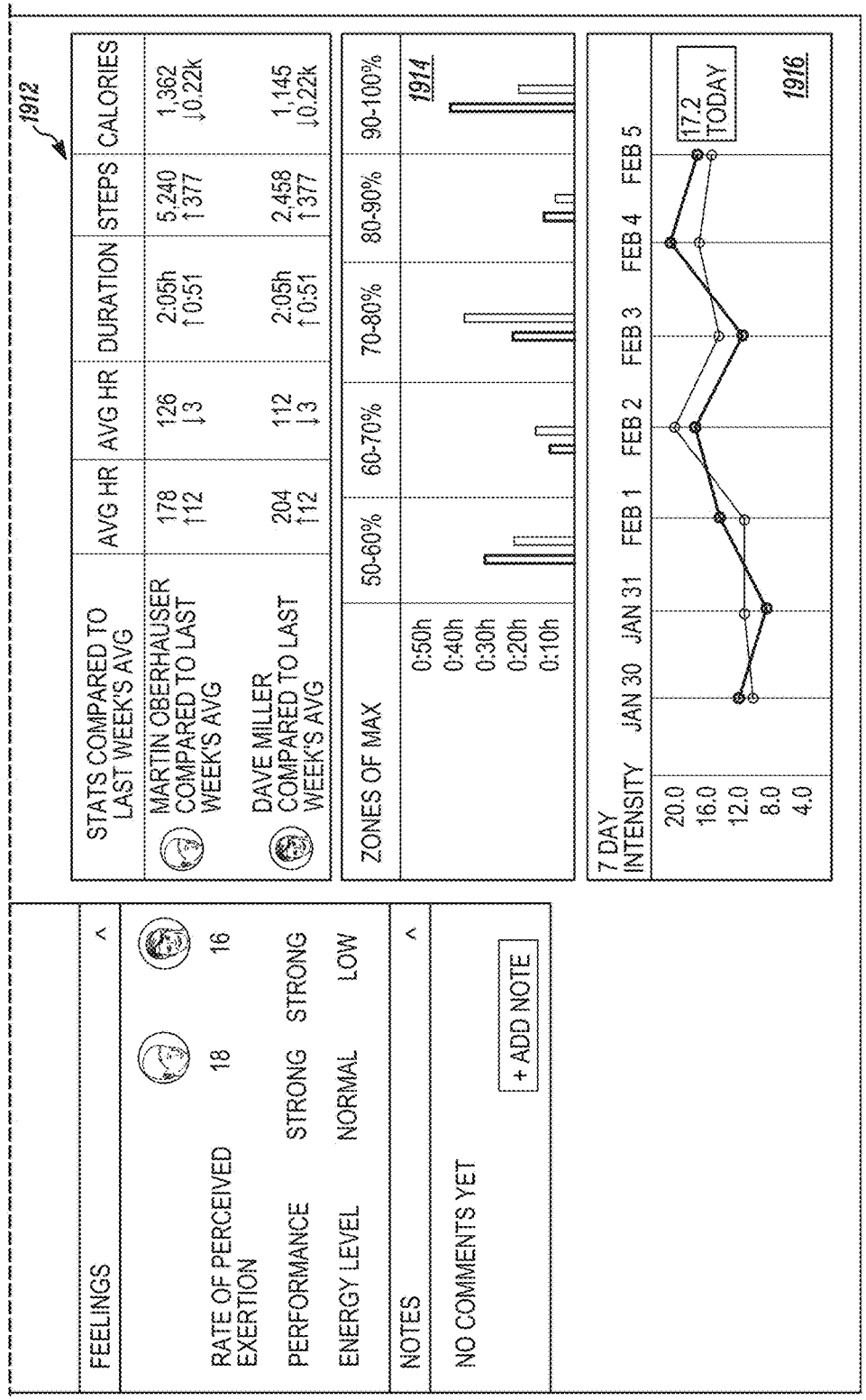

FIGS. 19A and 19B illustrate an exemplary user interface 1900 rendered on a visual display device for displaying physiological data on a plurality of users. In some cases, a user may freely compare the data of any users whose data is available and accessible, i.e., set to an appropriate privacy level. In some cases, comparative data may correspond to a plurality of users who may be grouped together based on any suitable criteria, e.g., members of a gym, military team, and the like. In some cases, the user may be able to discover other users or comparable data by searching or performing queries on any desired parameters, for example, workouts, activities, age groups, locations, intensities, recoveries and the like. For example, a user may perform a query for "Workouts above a 17 Intensity in Boston for runners my age." The exemplary user interface may also identify or suggest users with whom to exchange data based on similar parameters. Data on any number of users may be presented and compared including, but not limited to, 2, 3, 4, 5, 6, 7, 8, 9, 10, and the like.

Figure 20:
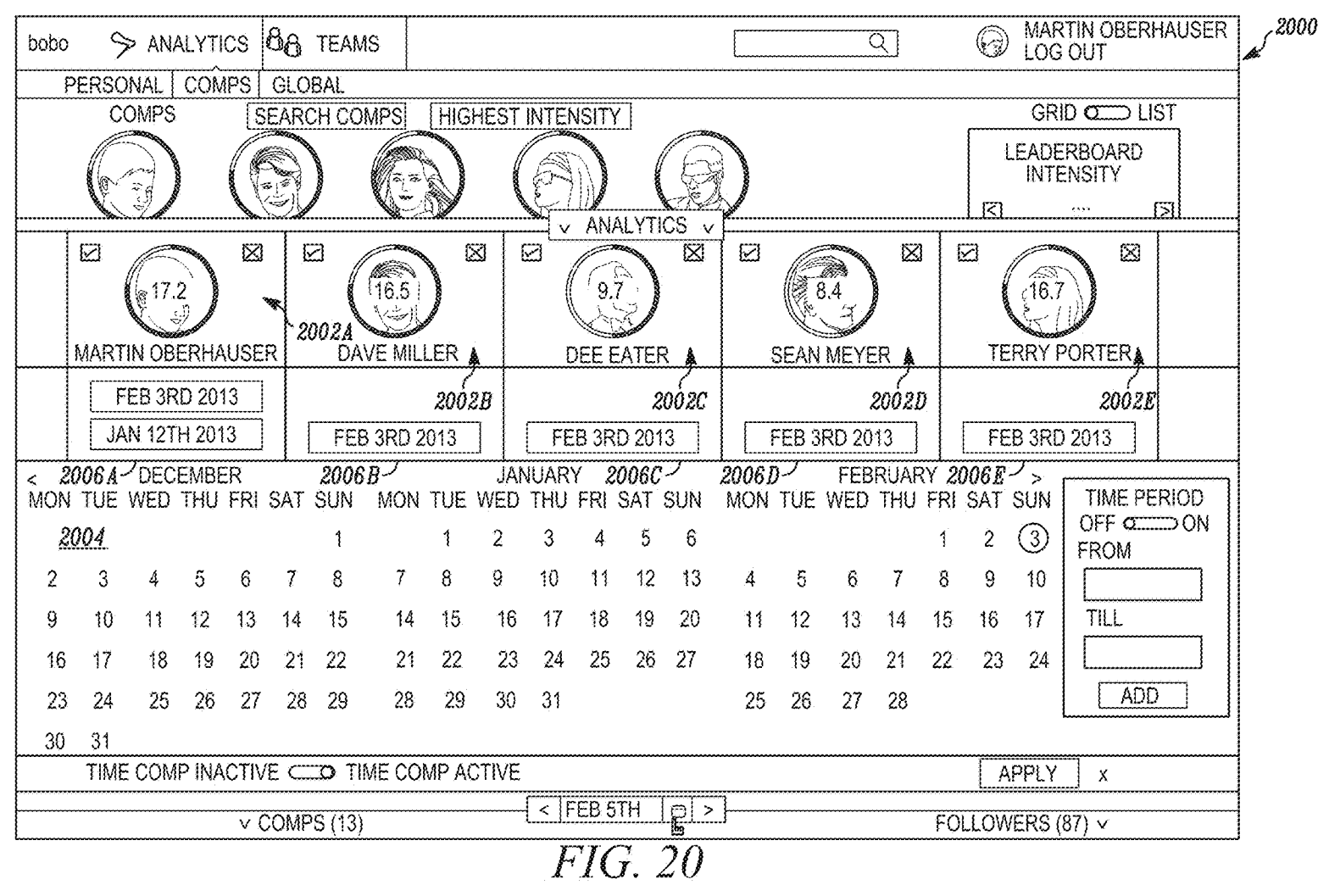

In a default option, data from the same time period(s) may be presented for all of the users. In some embodiments, time periods for each user may be selected independently and data from the selected time periods may be displayed in a comparative manner on the same user interface, e.g., in one or more overlaid graphs. FIG. 20 illustrates a user interface 2000 that may be used to independently select time periods of data for each of five users so that the data from the selected periods may be displayed together. The user interface 2000 includes a representation of each user 2002a-2002e, optionally an indication of each user's intensity score, a calendar component 2004 for selecting the time periods, and a component 2006a-2006e indicating the time periods selected for each user. In some cases, data from different time periods (but, for example, for the same time duration) for the same user may be presented on the same user interface for comparative purpose, for example, to determine training progress.

In FIGS. 19A and 19B, the user interface 1900 may include a summary panel 1902 including an identification 1904a-1904b of the users (e.g., a real or account name) with, optionally, a picture or photo corresponding to the user. In some cases, the summary panel 1902 may also display certain information associated with the users, for example, their intensity scores.

A workout panel 1908 may present quantitative information on the users' health and exercise routines, for example, an overlaid graph 1910 of the users' continuous heart rate during the exercise, statistics 1912 on the users' maximum heart rate, average heart rate, duration of exercise, number of steps taken and calories expended, zones 1914 in which the users' maximum heart rate fell during the exercise, and an overlaid graph 1916 of the users' intensity scores over a period of time (e.g., seven days).

A feedback panel 1918 associated with the workout panel 1908 may present comparative qualitative information on the users' exercise routines including, but not limited to, whether the users were working out at the same time, which user had a more difficult workout, the comparative efficiencies of the users, and the like. Similarly, a day panel and a sleep panel may present comparative information for the selected users.

The analytics system may analyze comparative data among a plurality of users and provide rankings of individuals, teams and groups of individuals (e.g., employees of a company, members of a gym) based on, for example, average intensity scores. For each user, the analytics system may calculate and display percentile rankings of the user with respect to all of the users in a community in terms of, for example, intensity scores, quality of sleep, and the like.

Exemplary embodiments also provide user interfaces to enable intuitive and efficient monitoring of a plurality of users by an individual with administrative powers to view the users' health data. Such an administrative user may be a physical instructor, trainer or coach who may use the interface to manage his/her clients' workout regimen.

Figure 21A:
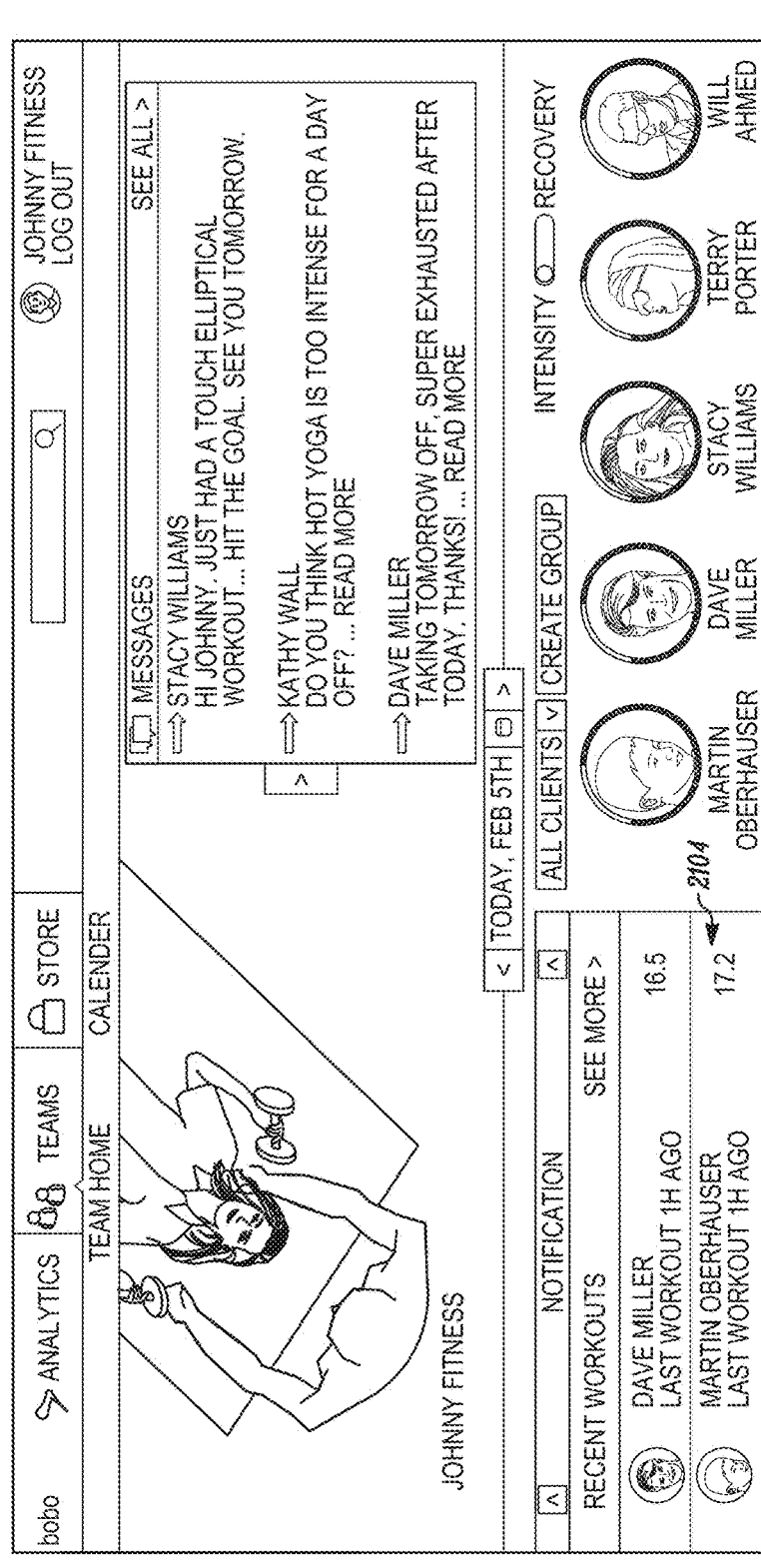
FIGS. 21A and 21B illustrate an exemplary user interface viewable by an administrative user, including a selectable and editable listing of users (e.g., a trainer's clients) whose health information is available for display.
Figure 21B:

FIGS. 21A and 21B illustrate an exemplary user interface 2100 viewable by an administrative user, including a selectable and editable representation or listing 2102 of the users (e.g., a trainer's clients) whose health information is available for display. When a pointer is hovered over a user selection component (e.g., an icon representing a user), a snapshot of the user's information is presented in a popup component, and clicking on the user selection component opens up the full user interface displaying the user's information. In some cases, the user selection components include certain user-specific data surrounding an image representing the user, for example, a graphic element indicating the user's intensity score. The user selection components in the listing 2102 may be provided in a grid as shown or in a linear listing for easier sorting. The users appearing in the listing 2102 may be sorted and/or ranked based on any desired criteria, e.g., intensity scores, who is experiencing soreness, and the like. Selection of any one user causes the user interface specific to that user to be opened, for example, as shown in FIGS. 15A-18B. The administrative user may leave messages on the user interfaces of the different users. Selection of more than one user causes a user interface comparing the selected users to be opened, for example, as shown in FIGS. 19A and 19B.

The administrative user interface 2100 may include a listing of users 2104 who recently performed exercise routines including the time of their last workout and their intensity scores, a listing of users 2106 who are off-schedule in their exercise regimen and how many days they have not been exercising, a listing of users 2108 who are experiencing soreness (that may be determined automatically based on intensity scores), a listing of users who are sleep-deprived (that may be determined automatically based on sleep data), and the like. The lists may be ordered in some cases. The user interface 2100 may also display a calendar or portion of a calendar 2110 indicating training times for different users. The calendar feature enables the administrative user to review exercise schedules over time and understand how well individuals or teams are meeting goals. For example, the administrative user may determine that an individual is undertraining if his intensity for the day was 18 whereas the team average was 14.

In any of the exemplary user interfaces disclosed herein, color coding may be used to indicate categories of any parameter. For example, in a day panel of a user interface, color coding may be used to indicate whether a user's day was difficult (e.g., with the color red), tapering (e.g., with the color yellow), or a day off from training (e.g., with the color blue).

Exemplary embodiments enable selected qualitative and/or quantitative data from any of the user interfaces disclosed herein to be selected, packaged and exported to an external application, computational device or webpage (e.g., a blog) for display, storage and analysis. The data may be selected based on any desired characteristic including, but not limited to, gender, age, location, activity, intensity level, and any combinations thereof. An online blog may be presented to display the data and allow users to comment on the data.

V. EXEMPLARY COMPUTING DEVICES

Various aspects and functions described herein in accord with the present invention may be implemented as hardware, software or a combination of hardware and software on one or more computer systems. Exemplary computer systems that may be used include, but are not limited to, personal computers, embedded computing systems, network appliances, workstations, mainframes, networked clients, servers, media servers, application servers, database servers, web servers, virtual servers, and the like. Other examples of computer systems that may be used include, but are not limited to, mobile computing devices, such as wearable devices, cellular phones and personal digital assistants, and network equipment, such as load balancers, routers and switches.

Figure 22:
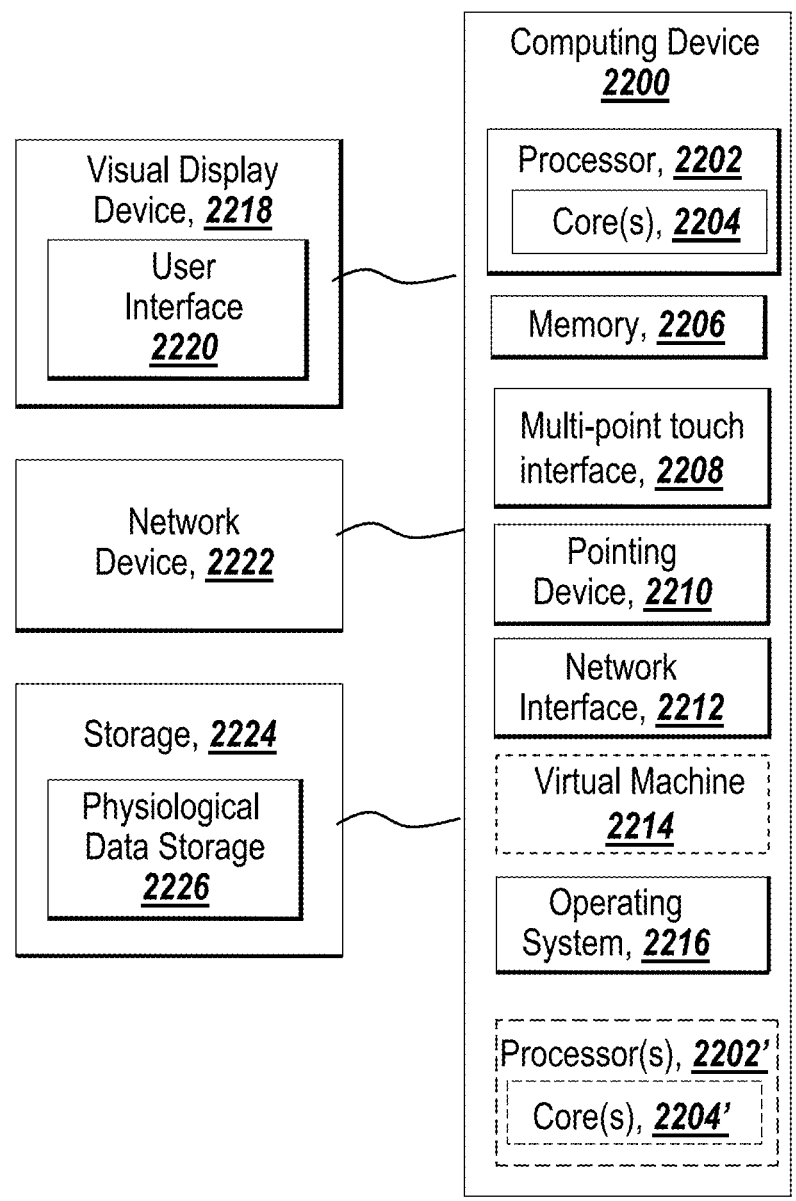
FIG. 22 is a block diagram of an exemplary computing device that may be used to perform any of the methods provided by exemplary embodiments.

FIG. 22 is a block diagram of an exemplary computing device 2200 that may be used to perform any of the methods provided by exemplary embodiments. The computing device may be configured as an embedded system in the integrated circuit board(s) of a wearable physiological measurements system and/or as an external computing device that may receive data from a wearable physiological measurement system.

The computing device 2200 includes one or more non-transitory computer-readable media for storing one or more computer-executable instructions or software for implementing exemplary embodiments. The non-transitory computer-readable media may include, but are not limited to, one or more types of hardware memory, non-transitory tangible media (for example, one or more magnetic storage disks, one or more optical disks, one or more USB flashdrives), and the like. For example, memory 2206 included in the computing device 2200 may store computer-readable and computer-executable instructions or software for implementing exemplary embodiments. The computing device 2200 also includes processor 2202 and associated core 2204, and optionally, one or more additional processor(s) 2202' and associated core(s) 2204' (for example, in the case of computer systems having multiple processors/cores), for executing computer-readable and computer-executable instructions or software stored in the memory 2206 and other programs for controlling system hardware. Processor 2202 and processor(s) 2202' may each be a single core processor or multiple core (2204 and 2204') processor.

Virtualization may be employed in the computing device 2200 so that infrastructure and resources in the computing device may be shared dynamically. A virtual machine 2214 may be provided to handle a process running on multiple processors so that the process appears to be using only one computing resource rather than multiple computing resources. Multiple virtual machines may also be used with one processor.

Memory 2206 may include a computer system memory or random access memory, such as dynamic random-access memory (DRAM), static random-access memory (SRAM), extended data output random-access memory (EDO RAM), and the like. Memory 2206 may include other types of memory as well, or combinations thereof.

A user may interact with the computing device 2200 through a visual display device 2218, such as a computer monitor, which may display one or more user interfaces 2220 that may be provided in accordance with exemplary embodiments. The visual display device 2218 may also display other aspects, elements and/or information or data associated with exemplary embodiments, for example, views of databases, photos, and the like. The computing device 2200 may include other input/output (I/O) devices for receiving input from a user, for example, a keyboard or any suitable multi-point touch interface 2208, a pointing device 2210 (e.g., a mouse). The keyboard 2208 and the pointing device 2210 may be coupled to the visual display device 2218. The computing device 2200 may include other suitable conventional I/O peripherals.

The computing device 2200 may also include one or more storage devices 2224, such as a hard-drive, CD-ROM, or other computer readable media, for storing data and computer-readable instructions and/or software that implement exemplary methods as taught herein. Exemplary storage device 2224 may also store one or more databases 2226 for storing any suitable information required to implement exemplary embodiments (e.g., physiological data, computer-executable instructions for analyzing the data, and the like). The databases may be updated by a user or automatically at any suitable time to add, delete or update one or more items in the databases.

The computing device 2200 may include a network interface 2212 configured to interface via one or more network devices 2222 with one or more networks, for example, Local Area Network (LAN), Wide Area Network (WAN) or the Internet through a variety of connections including, but not limited to, standard telephone lines, LAN or WAN links (for example, 802.11, T1, T3, 56 kb, X.25), broadband connections (for example, ISDN, Frame Relay, ATM), wireless connections, controller area network (CAN), or some combination of any or all of the above. The network interface 2212 may include a built-in network adapter, network interface card, personal computer memory card international associate (PCMCIA) network card, card bus network adapter, wireless network adapter, universal serial bus (USB) network adapter, modem or any other device suitable for interfacing the computing device 2200 to any type of network capable of communication and performing the operations described herein. Moreover, the computing device 2200 may be any computer system, such as a workstation, desktop computer, server, laptop, handheld computer, tablet computer (e.g., the iPad™ tablet computer), mobile computing or communication device (e.g., the iPhone™ communication device), or other form of computing or telecommunications device that is capable of communication and that has sufficient processor power and memory capacity to perform the operations described herein.

The wearable physiological measurement system may record and transmit at least the following types of data to an external computing system, mobile communication system, a cloud or non-cloud storage system, and/or the Internet: raw physiological data (e.g., heart rate data, movement data, galvanic skin response data) and processed data derived from the raw data (e.g., RR intervals determined from the heart rate data). Transmission modes may be wired (e.g., using USB stick inserted into a USB port on the system) or wireless (e.g., using a wireless transmitter). The raw and processed data may be transmitted together or separately using the same or different transmission modes. Since a raw data file is typically substantially larger than a processed data file, in one non-limiting example, the raw data file may be transmitted using WiFi or a USB stick, while the processed data file may be transmitted using Bluetooth.

An exemplary wearable system may include a 2G, 3G or 4G chip that wirelessly uploads all data to the website disclosed herein without requiring any other external device. A 3G or 4G chip may be used preferably as a 2G connection on a Nokia 5800 was found to transfer data at a rate of 520 kbps using 1.69 W of power, while a 3G connection transferred at 960 kbps using 1.73 W of power. That is, the 3G chip was found to use negligibly more power for almost twice the transfer speed, thereby halving half the transfer time and using much less energy from the battery.

In some cases, the wearable system may opportunistically transfer data when in close proximity to a streaming outlet. For example, the system may avoid data transmission when it is not within close proximity of a streaming outlet, and, when nearby a streaming outlet (e.g., a linked phone), may send the data to the external device via Bluetooth and to the Internet via the external device. This is both convenient and "free" in the sense that the system utilizes existing cellular data plans.

Limiting the frequency at which data is streamed increases the wearable system's battery life. In one non-limiting example, the system may be set to stream automatically at a certain time of the day (e.g., in the morning) and following a time-stamp. Regardless of the data transmission scheme, the system stores all the data it collects. Data may also be streamed on demand by a user, for example, by turning a physical component on the system and holding it or by initiating a process on a mobile application or receiving device. In some embodiments, the data transmission frequency may be automatically adjusted based on one or more physiological parameters, e.g., heart rate. For example, higher heart rates may prompt more frequent and real-time streaming transmission of data.

The computing device 2200 may run any operating system 2216, such as any of the versions of the Microsoft® Windows® operating systems, the different releases of the Unix and Linux operating systems, any version of the MacOS® for Macintosh computers, any embedded operating system, any real-time operating system, any open source operating system, any proprietary operating system, any operating systems for mobile computing devices, or any other operating system capable of running on the computing device and performing the operations described herein. In exemplary embodiments, the operating system 2216 may be run in native mode or emulated mode. In an exemplary embodiment, the operating system 2216 may be run on one or more cloud machine instances.

VI. EXEMPLARY NETWORK ENVIRONMENTS

Various aspects and functions of the present invention may be distributed among one or more computer systems configured to provide a service to one or more client computers, or to perform an overall task as part of a distributed system. Additionally, aspects may be performed on a client-server or multi-tier system that includes components distributed among one or more server systems that perform various functions. Thus, the present invention is not limited to executing on any particular system or group of systems. Further, aspects may be implemented in software, hardware or firmware, or any combination thereof. Thus, aspects in accord with the present invention may be implemented within methods, acts, systems, system placements and components using a variety of hardware and software configurations, and the invention is not limited to any particular distributed architecture, network or communication protocol. Furthermore, aspects in accord with the present invention may be implemented as specially-programmed hardware and/or software.

Figure 23:
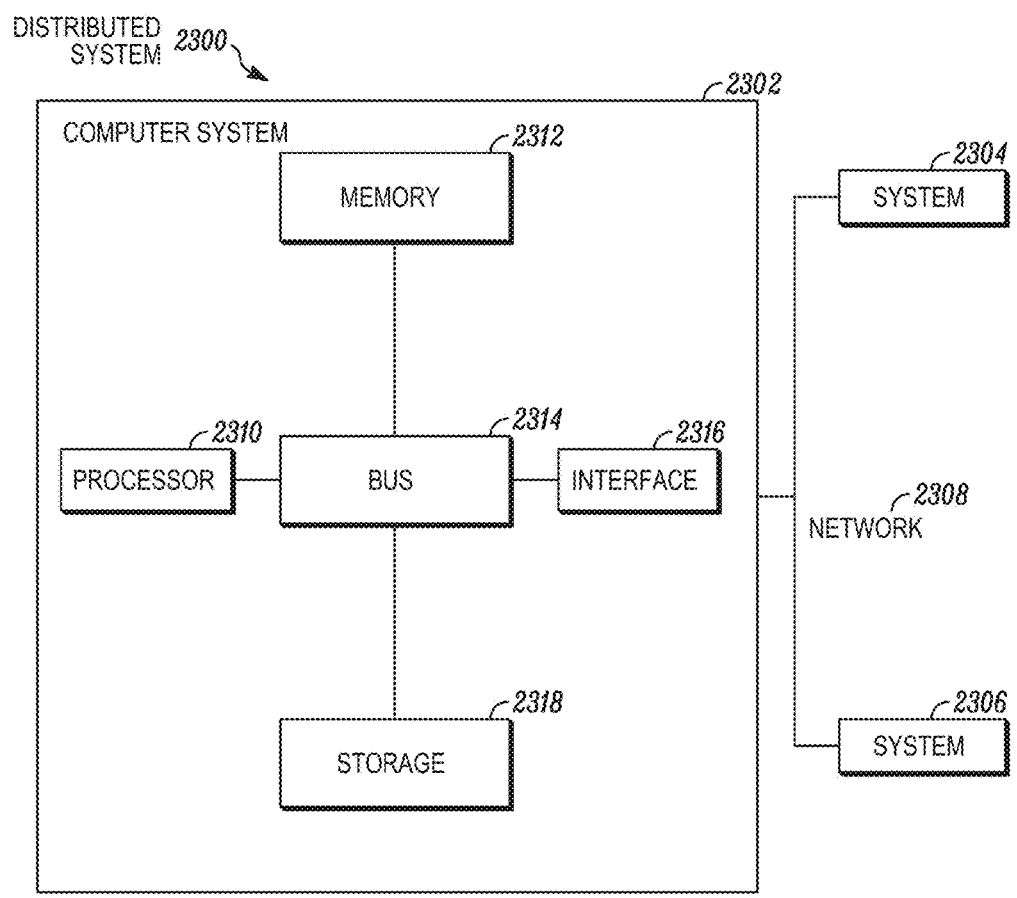
FIG. 23 is a block diagram of an exemplary distributed computer system in which various aspects and functions in accord with the present invention may be practiced.

FIG. 23 is a block diagram of an exemplary distributed computer system 2300 in which various aspects and functions in accord with the present invention may be practiced. The distributed computer system 2300 may include one or more computer systems. For example, as illustrated, the distributed computer system 2300 includes three computer systems 2302, 2304 and 2306. As shown, the computer systems 2302, 2304, 2306 are interconnected by, and may exchange data through, a communication network 2308. The network 2308 may include any communication network through which computer systems may exchange data. To exchange data via the network 2308, the computer systems and the network may use various methods, protocols and standards including, but not limited to, token ring, Ethernet, wireless Ethernet, Bluetooth, transmission control protocol/internet protocol (TCP/IP), user datagram protocol (UDP), hypertext transfer protocol (HTTP), file transfer protocol (FTP), simple network management protocol (SNMP), short message service (SMS), multimedia messaging service (MMS), signaling system no. 7 (SS7), JavaScript Object Notation (JSON), extensible markup language (XML), representational state transfer (REST), simple object access protocol (SOAP), common object request broker architecture (CORBA), internet inter-ORB protocol (IIOP), remote method invocation (RMI), distributed component object model (DCOM), and Web Services. To ensure data transfer is secure, the computer systems may transmit data via the network using a variety of security measures including, but not limited to, transport layer security (TSL), secure sockets layer (SSL) and virtual private network (VPN). While the distributed computer system 2300 illustrates three networked computer systems, the distributed computer system may include any number of computer systems, networked using any medium and communication protocol.

Various aspects and functions in accord with the present invention may be implemented as specialized hardware or software executing in one or more computer systems. As depicted, the computer system 2300 includes a processor 2310, a memory 2312, a bus 2314, an interface 2316 and a storage system 2318. The processor 2310, which may include one or more microprocessors or other types of controllers, can perform a series of instructions that manipulate data. The processor 2310 may be a well-known commercially-available processor such as an Intel Pentium, Intel Atom, ARM Processor, Motorola PowerPC, SGI MIPS, Sun UltraSPARC or Hewlett-Packard PA-RISC processor, or may be any other type of processor or controller as many other processors and controllers are available. The processor 2310 may be a mobile device or smart phone processor, such as an ARM Cortex processor, a Qualcomm Snapdragon processor or an Apple processor. As shown, the processor 2310 is connected to other system placements, including a memory 2312, by the bus 2314.

The memory 2312 may be used for storing programs and data during operation of the computer system 2300. Thus, the memory 2312 may be a relatively high performance, volatile, random access memory such as a dynamic random access memory (DRAM) or static memory (SRAM). However, the memory 2312 may include any device for storing data, such a disk drive or other non-volatile storage device, such as flash memory or phase-change memory (PCM). Various embodiments in accord with the present invention can organize the memory 2312 into particularized and, in some cases, unique structures to perform the aspects and functions disclosed herein.

Components of the computer system 2300 may be coupled by an interconnection element such as the bus 2314. The bus 2314 may include one or more physical busses (for example, buses between components that are integrated within the same machine) and may include any communication coupling between system placements including specialized or standard computing bus technologies such as integrated development environment (IDE), small computer system interface (SCSI), peripheral component interconnect (PCI) and InfiniBand. Thus, the bus 2314 enables communications (for example, data and instructions) to be exchanged between system components of the computer system 2300.

Computer system 2300 also includes one or more interface devices 2316, such as input devices, output devices and combination input/output devices. The interface devices 2316 may receive input, provide output, or both. For example, output devices may render information for external presentation. Input devices may accept information from external sources. Examples of interface devices include, but are not limited to, keyboards, mouse devices, trackballs, microphones, touch screens, printing devices, display screens, speakers, network interface cards, and the like. The interface devices 2316 allow the computer system 2300 to exchange information and communicate with external entities, such as users and other systems.

Storage system 2318 may include one or more computer-readable and computer-writeable non-volatile and non-transitory storage media on which computer-executable instructions are encoded that define a program to be executed by the processor. The storage system 2318 also may include information that is recorded on or in the media, and this information may be processed by the program. More specifically, the information may be stored in one or more data structures specifically configured to conserve storage space or increase data exchange performance. The instructions may be persistently stored as encoded signals, and the instructions may cause a processor to perform any of the functions described herein. A medium that can be used with various embodiments may include, for example, optical disk, magnetic disk or flash memory, among others. In operation, the processor 2310 or some other controller may cause data to be read from the non-transitory recording media into another memory, such as the memory 2312, that allows for faster access to the information by the processor than does the storage medium included in the storage system 2318. The memory may be located in the storage system 2318 and/or in the memory 2312. The processor 2310 may manipulate the data within the memory 2312, and then copy the data to the medium associated with the storage system 2318 after processing is completed. A variety of components may manage data movement between the media and the memory 2312, and the present invention is not limited thereto.

Further, the invention is not limited to a particular memory system or storage system. Although the computer system 2300 is shown by way of example as one type of computer system upon which various aspects and functions in accord with the present invention may be practiced, aspects of the invention are not limited to being implemented on the computer system. Various aspects and functions in accord with the present invention may be practiced on one or more computers having different architectures or components than that shown in the illustrative figures. For instance, the computer system 2300 may include specially-programmed, special-purpose hardware, such as for example, an application-specific integrated circuit (ASIC) tailored to perform a particular operation disclosed herein. Another embodiment may perform the same function using several general-purpose computing devices running MAC OS System X with Motorola PowerPC processors and several specialized computing devices running proprietary hardware and operating systems.

The computer system 2300 may include an operating system that manages at least a portion of the hardware placements included in computer system 2300. A processor or controller, such as processor 2310, may execute an operating system which may be, among others, a Windows-based operating system (for example, Windows NT, Windows 2000/ME, Windows XP, Windows 7, or Windows Vista) available from the Microsoft Corporation, a MAC OS System X operating system available from Apple Computer, one of many Linux-based operating system distributions (for example, the Enterprise Linux operating system available from Red Hat Inc.), a Solaris operating system available from Sun Microsystems, or a UNIX operating systems available from various sources. The operating system may be a mobile device or smart phone operating system, such as Windows Mobile, Android or iOS. Many other operating systems may be used, and embodiments are not limited to any particular operating system.

The processor and operating system together define a computing platform for which application programs in high-level programming languages may be written. These component applications may be executable, intermediate (for example, C# or JAVA bytecode) or interpreted code which communicate over a communication network (for example, the Internet) using a communication protocol (for example, TCP/IP). Similarly, functions in accord with aspects of the present invention may be implemented using an object-oriented programming language, such as SmallTalk, JAVA, C++, Ada, or C# (C-Sharp). Other object-oriented programming languages may also be used. Alternatively, procedural, scripting, or logical programming languages may be used.

Additionally, various functions in accord with aspects of the present invention may be implemented in a non-programmed environment (for example, documents created in HTML, XML or other format that, when viewed in a window of a browser program, render aspects of a graphical-user interface or perform other functions). Further, various embodiments in accord with aspects of the present invention may be implemented as programmed or non-programmed placements, or any combination thereof. For example, a web page may be implemented using HTML while a data object called from within the web page may be written in C++. Thus, the invention is not limited to a specific programming language and any suitable programming language could also be used.

A computer system included within an embodiment may perform functions outside the scope of the invention. For instance, aspects of the system may be implemented using an existing product. Aspects of the system may be implemented on database management systems such as SQL Server available from Microsoft of Seattle, Wash.; Oracle Database from Oracle of Redwood Shores, Calif.; and MySQL from Sun Microsystems of Santa Clara, Calif.; or integration software such as WebSphere middleware from IBM of Armonk, N.Y. However, a computer system running, for example, SQL Server may be able to support both aspects in accord with the present invention and databases for sundry applications not within the scope of the invention.

Figure 24:
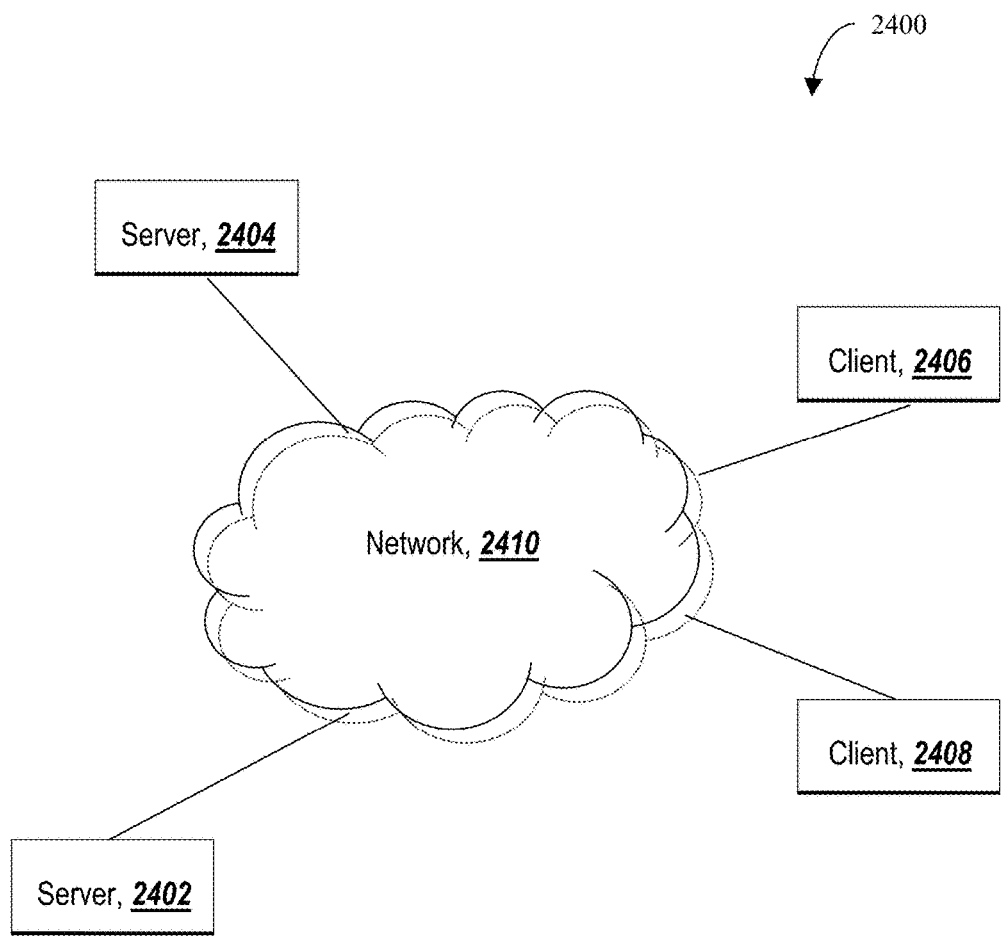
FIG. 24 is a diagram of an exemplary network environment suitable for a distributed implementation of exemplary embodiments.

FIG. 24 is a diagram of an exemplary network environment 2400 suitable for a distributed implementation of exemplary embodiments. The network environment 2400 may include one or more servers 2402 and 2404 coupled to one or more clients 2406 and 2408 via a communication network 2410. The network interface 2212 and the network device 2222 of the computing device 2200 enable the servers 2402 and 2404 to communicate with the clients 2406 and 2408 via the communication network 2410. The communication network 2410 may include, but is not limited to, the Internet, an intranet, a Local Area Network (LAN), a Wide Area Network (WAN), a Metropolitan Area Network (MAN), a wireless network, an optical network, and the like. The communication facilities provided by the communication network 2410 are capable of supporting distributed implementations of exemplary embodiments.

In an exemplary embodiment, the servers 2402 and 2404 may provide the clients 2406 and 2408 with computer-readable and/or computer-executable components or products under a particular condition, such as a license agreement. For example, the computer-readable and/or computer-executable components or products may include those for providing and rendering any of the user interfaces disclosed herein. The clients 2406 and 2408 may provide and render an exemplary graphical user interface using the computer-readable and/or computer-executable components and products provided by the servers 2402 and 2404.

Alternatively, in another exemplary embodiment, the clients 2406 and 2408 may provide the servers 2402 and 2404 with computer-readable and computer-executable components or products under a particular condition, such as a license agreement. For example, in an exemplary embodiment, the servers 2402 and 2404 may provide and render an exemplary graphical user interface using the computer-readable and/or computer-executable components and products provided by the clients 2406 and 2408.

VII. EQUIVALENTS

It is to be appreciated that embodiments of the systems, apparatuses and methods discussed herein are not limited in application to the details of construction and the arrangement of components set forth in the following description or illustrated in the accompanying drawings. Exemplary systems, apparatuses and methods are capable of implementation in other embodiments and of being practiced or of being carried out in various ways. Examples of specific implementations are provided herein for illustrative purposes only and are not intended to be limiting. In particular, acts, elements and features discussed in connection with any one or more embodiments are not intended to be excluded from a similar role in any other embodiments. One or more aspects and embodiments disclosed herein may be implemented on one or more computer systems coupled by a network (e.g., the Internet).

The phraseology and terminology used herein are for the purpose of description and should not be regarded as limiting. Any references to embodiments or elements or acts of the systems and methods herein referred to in the singular may also embrace embodiments including a plurality of these elements, and any references in plural to any embodiment or element or act herein may also embrace embodiments including only a single element. The use herein of terms like "including," "comprising," "having," "containing," "involving," and variations thereof, is meant to encompass the items listed thereafter and equivalents thereof as well as additional items. References to "or" may be construed as inclusive so that any terms described using "or" may indicate any of a single, more than one, and all of the described terms. Any references front and back, left and right, top and bottom, upper and lower, and vertical and horizontal, are intended for convenience of description, not to limit the present systems and methods or their components to any one positional or spatial orientation.

In describing exemplary embodiments, specific terminology is used for the sake of clarity. For purposes of description, each specific term is intended to, at least, include all technical and functional equivalents that operate in a similar manner to accomplish a similar purpose. Additionally, in some instances where a particular exemplary embodiment includes a plurality of system elements or method steps, those elements or steps may be replaced with a single element or step. Likewise, a single element or step may be replaced with a plurality of elements or steps that serve the same purpose. Further, where parameters for various properties are specified herein for exemplary embodiments, those parameters may be adjusted up or down by 1/20th, 1/10th, 1/5th, 1/3rd, 1/2nd, and the like, or by rounded-off approximations thereof, unless otherwise specified. Moreover, while exemplary embodiments have been shown and described with references to particular embodiments thereof, those of ordinary skill in the art will understand that various substitutions and alterations in form and details may be made therein without departing from the scope of the invention. Further still, other aspects, functions and advantages are also within the scope of the invention.

Embodiments disclosed herein may be combined with other embodiments disclosed herein in any manner consistent with at least one of the principles disclosed herein, and references to "an embodiment," "one embodiment," "an exemplary embodiment," "some embodiments," "some exemplary embodiments," "an alternate embodiment," "various embodiments," "exemplary embodiments," and the like, are not necessarily mutually exclusive and are intended to indicate that a particular feature, structure, characteristic or functionality described may be included in at least one embodiment. The appearances of such terms herein are not necessarily all referring to the same embodiment.

Exemplary flowcharts are provided herein for illustrative purposes and are non-limiting examples of methods. One of ordinary skill in the art will recognize that exemplary methods may include more or fewer steps than those illustrated in the exemplary flowcharts, and that the steps in the exemplary flowcharts may be performed in a different order than the order shown in the illustrative flowcharts.

What is claimed is:

1. A device for physiological monitoring and measurement comprising:
    a continuously wearable physiological measurement device including one or more sensors configured to continuously monitor and determine a heart rate of a user;
    a display device coupled to the continuously wearable physiological measurement device;
    a strap attached to the continuously wearable physiological measurement device and couplable to an appendage of the user; and
    a processor in the continuously wearable physiological measurement device, the processor coupled to the one or more sensors and the processor configured to:
        programmatically receive heart rate data for the user from the continuously wearable physiological measurement device, the heart rate data including a time series of heart rate data for the user, a maximum heart rate of the user, and a resting heart rate of the user;
        transform the heart rate data including the time series of heart rate data, the maximum heart rate and the resting heart rate to a time series of heart rate reserve data;
        weight the heart rate reserve data according to a dynamic weighting scheme to provide a dynamically weighted time series of heart rate reserve values, the dynamic weighting scheme based on historical heart rate reserve data;
        sum and normalize the dynamically weighted time series of heart rate reserve values for a predetermined unit interval to provide a summed and normalized value;
        programmatically generate an intensity score providing an indicator of cardiovascular intensity based on the dynamically weighted time series of heart rate reserve values, wherein generating the intensity score includes scaling the summed and normalized value to a predetermined distribution in a scale, and further wherein a path of the intensity score over time is used to dynamically determine and adjust the dynamic weighting scheme applied to the heart rate reserve data; and
        display the intensity score on a user interface rendered on the display device.

2. The device of claim 1, wherein the dynamic weighting scheme is created for the user by a machine learning algorithm trained to correlate heart rate data to cardiovascular intensities.

3. The device of claim 2, wherein the machine learning algorithm is retrained to adjust perceived difficulties of exercise routines as a fitness of the user improves.

4. The device of claim 1, wherein the dynamic weighting scheme accounts for cardiovascular efficiencies at different intensity levels.

5. The device of claim 1, wherein the processor is further configured to display qualitative information associated with the intensity score.

6. The device of claim 5, wherein the qualitative information includes an indication of whether the user exceeded an anaerobic threshold of the user during an exercise routine.

7. The device of claim 5, wherein the qualitative information includes an indication of whether the user is likely to experience muscle soreness.

8. The device of claim 5, wherein the qualitative information includes an indication of a level of recovery required after an exercise routine.

9. The device of claim 5, wherein the qualitative information includes an indication of one or more future alterations to an exercise routine that is required based on one or more health-related goals of the user.

10. The device of claim 1, wherein the indicator corresponds to a perceived difficulty of an exercise routine by the user, and wherein the processor is further configured to:
    display, on the user interface, the perceived difficulty of the exercise routine.

11. The device of claim 1, wherein the processor is further configured to:
    automatically alter an exercise plan according to one or more health goals of the user based on the intensity score; and
    display, on the user interface, an altered exercise plan.

12. The device of claim 1, wherein the predetermined distribution is a linear distribution.

13. The device of claim 1, wherein the predetermined distribution is one or more of an arctangent distribution, a sigmoid distribution, and a sinusoidal distribution.

14. The device of claim 1, wherein the predetermined distribution is obtained by fitting a curve to a predetermined group of canonical exercise routines have predefined intensity scores.

15. The device of claim 1, wherein the processor is further configured to programmatically receive heart rate variability data from the continuously wearable physiological measurement device.

16. The device of claim 15, wherein the processor is further configured to calculate a recovery score for the user based on the heart rate variability data.

* * * * *